US010508282B2

(12) United States Patent
Mockler

(10) Patent No.: US 10,508,282 B2
(45) Date of Patent: Dec. 17, 2019

(54) INCREASING PLANT GROWTH AND YIELD BY USING AN ERF TRANSCRIPTION FACTOR SEQUENCE

(71) Applicant: BENSON HILL, INC., St. Louis, MO (US)

(72) Inventor: Todd Christopher Mockler, St Louis, MO (US)

(73) Assignee: Benson Hill, Inc., St. Louis, MO (US)

( * ) Notice: Subject to any disclaimer, the term of this patent is extended or adjusted under 35 U.S.C. 154(b) by 0 days.

(21) Appl. No.: 16/380,199

(22) Filed: Apr. 10, 2019

(65) Prior Publication Data

US 2019/0233840 A1 Aug. 1, 2019

Related U.S. Application Data

(62) Division of application No. 15/797,494, filed on Oct. 30, 2017, now Pat. No. 10,301,640.

(60) Provisional application No. 62/484,118, filed on Apr. 11, 2017, provisional application No. 62/414,936, filed on Oct. 31, 2016.

(51) Int. Cl.
*C12N 15/82* (2006.01)
*C07K 14/415* (2006.01)

(52) U.S. Cl.
CPC ........ *C12N 15/8261* (2013.01); *C07K 14/415* (2013.01); *C12N 15/8216* (2013.01); *Y02A 40/146* (2018.01)

(58) Field of Classification Search
None
See application file for complete search history.

(56) References Cited

U.S. PATENT DOCUMENTS

| 7,825,296 | B2 | 11/2010 | Jiang et al. |
| 7,858,848 | B2 | 12/2010 | Reuber et al. |
| 2010/0281578 | A1 | 11/2010 | Bate et al. |

FOREIGN PATENT DOCUMENTS

| WO | WO 2011/161620 A1 | 12/2011 |
| WO | WO 2012/158594 A2 | 11/2012 |
| WO | WO 2014/100289 A1 | 6/2014 |

OTHER PUBLICATIONS

NCBI, GenBank Sequence Accession No. XM_010238337.1, Published Nov. 14, 2014; pp. 1-2.*
Ambavaram, M., et al., "Coordinated regulation of photosynthesis in rice increases yield and tolerance to environmental stress," *Nature Communications*, 2014, vol. 5(5302), pp. 1-14.
Joshi, R., et a., "Transcription Factors and Plants Response to Drought Stress: Current Understanding and Future Directions," *Frontiers in Plant Science*, 2016, vol. 7, pp. 1-15, https://www.ncbi.nim.nih.gov/pmc/articles/PMC4943945.
Hu, Y., et al., "Overexpression of OsERF1, a novel rice ERF gene, up-regulates ethylene-responsive genes expression besides affects growth and development in *Arabidopsis*," *Journal of Plant Physiology*, 2008, vol. 165, pp. 1717-1725.
Karaba, A., et al., "Improvement of water use efficiency in rice by expression of HARDY, an *Arabidopsis* drought and salt tolerance gene," *PNAS*, 2007, vol. 104(39, pp. 15270-15275.
Licausi, F., et al., "APETALA2/Ethylene Responsive Factor (AP2/ERF) transcription factors: mediators of stress responses and developmental programs," *New Phytologist*, 2013, vol. 199(3), pp. 639-649.
NCBI GenBank Sequence Accession No. XM_010238337.1, 2014, pp. 1-2.
Wuddineh, W., et al., "Identification and molecular characterization of the switchgrass AP2/ERF transcription factor superfamily, and overexpression of PvERF001 for improvement of biomass characteristics for biofuel," *Frontiers in Bioengineering and Biotechnology*, 2015, vol. 3, pp. 1-21.
Yang, Z., et al., "*Arabidopsis* ERF4 is a transcriptional repressor capable of modulating ethylene and abscisic acid responses," *Plant Molecular Biology*, 2005, vol. 58, pp. 585-596.
Zhao, L., et al., "A RAV-like transcription factor controls photosynthesis and senescence in soybean," *Planta*, 2008, vol. 227, pp. 1389-1399.

* cited by examiner

*Primary Examiner* — Vinod Kumar
(74) *Attorney, Agent, or Firm* — Womble Bond Dickinson (US) LLP

(57) ABSTRACT

Compositions and methods for improving plant growth are provided herein. Polynucleotides encoding ERF transcription factor proteins, polypeptides encompassing ERF transcription factor proteins, and expression constructs for expressing genes of interest whose expression may improve agronomic properties including but not limited to crop yield, biotic and abiotic stress tolerance, and early vigor, plants comprising the polynucleotides, polypeptides, and expression constructs, and methods of producing transgenic plants are also provided.

20 Claims, No Drawings

Specification includes a Sequence Listing.

INCREASING PLANT GROWTH AND YIELD BY USING AN ERF TRANSCRIPTION FACTOR SEQUENCE

FIELD OF THE INVENTION

The invention is drawn to compositions and methods for increasing plant growth and yield through expression of an ERF transcription factor gene in a plant.

BACKGROUND OF THE INVENTION

The ever-increasing world population and the dwindling supply of arable land available for agriculture fuels research towards developing plants with increased biomass and yield. Conventional means for crop and horticultural improvements utilize selective breeding techniques to identify plants having desirable characteristics. However, such selective breeding techniques have several drawbacks, namely that these techniques are typically labor intensive and result in plants that often contain heterogeneous genetic components that may not always result in the desirable trait being passed on from parent plants. Advances in molecular biology provide means to precisely modify the germplasm of plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits.

Traits of interest include plant biomass and yield. Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. Root development, nutrient uptake, stress tolerance, photosynthetic carbon assimilation rates, and early vigor may also be important factors in determining yield. Optimizing the abovementioned factors may therefore contribute to increasing crop yield.

An increase in seed yield is a particularly important trait since the seeds of many plants are important for human and animal consumption. Crops such as corn, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. An increase in plant biomass is important for forage crops like alfalfa, silage corn and hay. Many genes are involved in the metabolic pathways that contribute to plant growth and development. Modulating the expression of one or more such genes in a plant can produce a plant with improved growth and development relative to a control plant, but often can produce a plant with impaired growth and development relative to a control plant. Therefore, methods to improve plant growth and development are needed.

Transcription factors are genes whose expression modulates the expression of other genes. This is often accomplished by the transcription factor protein binding to genomic DNA at a particular location or locations. This binding may recruit additional proteins that up- or down-regulate the expression of gene(s) nearby the transcription factor binding site. Alternatively, the binding of the transcription factor to DNA may physically slow or prevent transcription of nearby gene(s) by interfering with proteins such as RNA polymerase that are involved with transcription. Because individual transcription factors may affect the expression of multiple genes of interest, modulating transcription factor expression has the potential to simultaneously modulate the expression of multiple genes in the organism of interest, such as genes that are involved in the metabolic pathways that contribute to plant growth and development. Modulating the expression of one or more transcription factors that participates in regulating the expression of genes whose expression affects plant growth and development may improve plant growth and development, but often can produce a plant with impaired growth and development relative to a control plant. Therefore, methods to modulate transcription factor expression that can result in improved plant growth and development are needed.

SUMMARY OF THE INVENTION

Compositions and methods for modifying the expression of at least one ERF transcription factor gene in a plant are provided. The methods increase plant growth resulting in higher crop yield. Such methods include increasing the expression of at least one ERF transcription factor gene in a plant of interest. The invention also encompasses constructs comprising a promoter that drives expression in a plant cell operably linked to an ERF transcription factor coding sequence. Compositions further comprise plants, plant seeds, plant organs, plant cells, and other plant parts that have increased expression of an ERF transcription factor sequence. The invention includes methods that can be utilized to increase expression of an ERF transcription factor gene in a plant. Such ERF transcription factor gene may be a native sequence or alternatively, may be a sequence that is heterologous to the plant of interest.

Embodiments of the invention include:
1. A method for increasing crop yield comprising transforming a plant with at least one ERF transcription factor protein-encoding sequence.
2. The method of embodiment 1, wherein said ERF transcription factor protein-encoding sequence comprises a sequence selected from the group of SEQ ID NOs:1, 56, 58, 60, 62, and 64, or encodes a protein selected from the group consisting of SEQ ID NOs:2, 22-53, 57, 59, 61, 63, and 65.
3. The method of embodiment 1, wherein said ERF transcription factor protein-encoding sequence encodes a protein with at least 80%, 90%, 95%, 96%, 97%, 98%, or 99% sequence identity to a sequence selected from the group consisting of SEQ ID NOs: 2, 22-53, 57, 59, 61, 63, and 65, and that has transcription factor function.
4. The method of embodiment 1, wherein said ERF transcription factor protein-encoding sequence encodes a protein with at least 80%, 85%, 90%, 95%, 96%, 97%, 98%, or 99% sequence positives relative to a sequence selected from the group consisting of SEQ ID NOs: 2, 22-53, 57, 59, 61, 63, and 65, and that has transcription factor function.

5. A plant having stably incorporated into its genome a promoter that drives expression in a plant cell operably linked to a ERF transcription factor protein-encoding sequence, wherein said promoter is heterologous to said ERF transcription factor protein-encoding sequence.

6. The plant of embodiment 5, wherein said ERF transcription factor protein-encoding sequence comprises a sequence selected from the group of SEQ ID NOs:1, 56, 58, 60, 62, and 64, or encodes a protein selected from the group consisting of SEQ ID NOs: 2, 22-53, 57, 59, 61, 63, and 65.

7. The plant of embodiment 5, wherein said ERF transcription factor protein-encoding sequence encodes a protein with at least 80%, 85%, 90%, 95%, 96%, 97%, 98%, or 99% sequence identity to a sequence selected from the group consisting of SEQ ID NOs: 2, 22-53, 57, 59, 61, 63, and 65, and that has transcription factor function.

8. The plant of embodiment 5, wherein said ERF transcription factor protein-encoding sequence encodes a protein with at least 80%, 85%, 90%, 95%, 96%, 97%, 98%, or 99% sequence positives relative to a sequence selected from the group consisting of SEQ ID NOs: 2, 22-53, 57, 59, 61, 63, and 65, and that has transcription factor function.

9. The plant of any one of embodiments 5-8, wherein said plant also has stably incorporated into its genome at least one additional coding sequence, and wherein said at least one additional coding sequence is selected from the group of SEQ ID NOs:14, 16, 18, 20, and 54 or encodes a protein selected from the group of SEQ ID NOs:15, 17, 19, 21, and 55.

10. Transformed seed of any one of the plants of embodiments 5-9.

11. The plant of any one of embodiments 5-9 wherein said plant is a monocot.

12. The plant of embodiment 11 wherein said plant is from the genus *Zea, Oryza, Triticum, Sorghum, Secale, Eleusine, Setaria, Saccharum, Miscanthus, Panicum, Pennisetum, Megathyrsus, Cocos, Ananas, Musa, Elaeis, Avena*, or *Hordeum*.

13. The plant of any one of embodiments 5-9 wherein said plant is a dicot.

14. The plant of embodiment 13 wherein said plant is from the genus *Glycine, Brassica, Medicago, Helianthus, Carthamus, Nicotiana, Solanum, Gossypium, Ipomoea, Manihot, Coffea, Citrus, Theobroma, Camellia, Persea, Ficus, Psidium, Mangifera, Olea, Carica, Anacardium, Macadamia, Prunus, Beta, Populus*, or *Eucalyptus*.

15. The plant of any one of embodiments 5-9 wherein said plant exhibits increased growth relative to a control plant.

16. The plant of any one of embodiments 5-9 wherein said plant exhibits increased biomass yield relative to a control plant.

17. The plant of any one of embodiments 5-9 wherein said plant exhibits increased seed yield relative to a control plant.

18. The method of any one of embodiments 1-4, wherein said ERF transcription factor protein-encoding sequence is expressed from a constitutive promoter.

19. The method of embodiment 18, wherein said constitutive promoter comprises SEQ ID NO:8.

20. The method of any one of embodiments 1-4, wherein said ERF transcription factor protein-encoding sequence is expressed from a stress-responsive promoter.

21. The method of embodiment 20, wherein said stress-responsive promoter comprises SEQ ID NO:5.

22. The method of any one of embodiments 1-4 further comprising transforming a plant with at least one additional coding sequence.

23. The method of embodiment 22 wherein said at least one additional coding sequence is selected from the group of SEQ ID NOs:14, 16, 18, 20, and 54 or encodes a protein selected from the group of SEQ ID NOs:15, 17, 19, 21, and 55.

24. The plant of any one of embodiments 5-9, wherein said promoter that drives expression in a plant cell is a constitutive promoter.

25. The plant of embodiment 24, wherein said constitutive promoter comprises SEQ ID NO:8.

26. The plant of any one of embodiments 5-9, wherein said promoter that drives expression in a plant cell is a stress-responsive promoter.

27. The plant of embodiment 26, wherein said stress-responsive promoter comprises SEQ ID NO:5.

28. A DNA construct comprising, in operable linkage,
  a. A promoter that is functional in a plant cell and,
  b. A nucleic acid sequence encoding an ERF transcription factor protein.

29. The DNA construct of embodiment 28, wherein said nucleic acid sequence encoding a ERF transcription factor protein comprises a sequence selected from the group of SEQ ID NOs:1, 56, 58, 60, 62, and 64, or encodes a protein selected from the group consisting of SEQ ID NOs: 2, 22-53, 57, 59, 61, 63, and 65.

30. The DNA construct of embodiment 28, wherein said nucleic acid sequence encoding an ERF transcription factor protein encodes a protein with at least 80%, 85%, 90%, 95%, 96%, 97%, 98%, or 99% sequence identity to a sequence selected from the group consisting of SEQ ID NOs: 2, 22-53, 57, 59, 61, 63, and 65, and that has transcription factor function.

31. The DNA construct of embodiment 28, wherein said nucleic acid sequence encoding an ERF transcription factor protein encodes a protein with at least 80%, 85%, 90%, 95%, 96%, 97%, 98%, or 99% sequence positives relative to a sequence selected from the group consisting of SEQ ID NOs: 2, 22-53, 57, 59, 61, 63, and 65, and that has transcription factor function.

32. The DNA construct of any one of embodiments 28-31, wherein said promoter that is functional in a plant cell is selected from the group of SEQ ID NOs:3, 5, 7, and 8.

33. The DNA construct of any one of embodiments 28-31, wherein said promoter that is functional in a plant cell is heterologous to said nucleic acid sequence encoding an ERF transcription factor protein.

34. A method for increasing crop yield comprising modulating the expression of at least one ERF transcription factor protein-encoding sequence in a plant.

35. The method of embodiment 34 wherein said modulating the expression comprises increasing the expression of at least one ERF transcription factor protein-encoding sequence in a plant.

36. The method of embodiment 35, wherein said increasing the expression comprises increasing the activity of a native ERF transcription factor sequence in said plant or increasing activity of a native ERF transcription factor protein-encoding sequence in said plant.
37. The DNA construct of any one of embodiments 28-33, further comprising at least one additional promoter that is functional in a plant cell, operably linked to at least one additional protein-encoding nucleic acid sequence.
38. The DNA construct of embodiment 37 wherein said additional protein-encoding nucleic acid sequence is selected from the group of SEQ ID NOs:14, 16, 18, 20, and 54, or encodes a protein selected from the group of SEQ ID NOs:15, 17, 19, 21, and 55.
39. The DNA construct of embodiment 37 wherein said additional protein-encoding nucleic acid sequence has at least 70% identity to a nucleic acid sequence selected from the group of SEQ ID NOs:14, 16, 18, 20, and 54, or encodes a protein with at least 80% identity to a protein selected from the group of SEQ ID NOs:15, 17, 19, 21, and 55.

DETAILED DESCRIPTION OF THE INVENTION

Compositions and methods for increasing crop biomass and yield are provided. The methods include increasing the expression of at least one ERF transcription factor gene in a plant of interest. Crop yield is an extremely complex trait that results from the growth of a crop plant through all stages of its development and allocation of plant resources to the harvestable portions of the plant. In some crops including but not limited to maize and soybean, the primary harvestable portions may include seeds, with secondary applications from the remainder of the biomass (e.g., leaves and stems). In other crops including but not limited to sugarcane and alfalfa, the primary harvestable portions of the plant consist of the stems or entire above-ground portion of the plant. In other crops including but not limited to potato and carrot, the primary harvestable portions of the plant are found below-ground. Regardless of the harvested portion(s) of the crop plant, the accumulation of harvestable biomass results from plant growth and allocation of photosynthetically fixed carbon to the harvested portion(s) of the plant. Plant growth may be manipulated by modulating the expression of one or more plant genes. This modulation can alter the function of one or more metabolic pathways that contributes to plant growth and accumulation of harvestable biomass.

Methods of the invention include the manipulation of plant growth for increased yield through modulation of the expression of one or more genes encoding an ERF transcription factor protein. In a preferred embodiment, the expression of an ERF transcription factor-encoding gene is upregulated relative to ERF transcription factor expression levels in a control plant, resulting in increased harvestable biomass in plants with increased ERF transcription factor expression relative to control plants. Any methods for increasing the activity or expression of an ERF transcription factor protein-encoding sequence in a plant are encompassed by the present invention.

The compositions of the invention include constructs comprising the coding sequences set forth in SEQ ID NOs: 1, 56, 58, 60, 62, and 64, or encoding a protein selected from the group of SEQ ID NOs: 2, 22-53, 57, 59, 61, 63, and 65 or variants thereof, operably linked to a promoter that is functional in a plant cell. By "promoter" is intended to mean a regulatory region of DNA that is capable of driving expression of a sequence in a plant or plant cell. It is recognized that having identified the ERF transcription factor protein sequences disclosed herein, it is within the state of the art to isolate and identify additional ERF transcription factor protein sequences and nucleotide sequences encoding ERF transcription factor protein sequences, for instance through BLAST searches, PCR assays, and the like.

The coding sequences of the present invention, when assembled within a DNA construct such that a promoter is operably linked to the coding sequence of interest, enable expression and accumulation of ERF transcription factor protein in the cells of a plant stably transformed with this DNA construct. "Operably linked" is intended to mean a functional linkage between two or more elements. For example, an operable linkage between a promoter of the present invention and a heterologous nucleotide of interest is a functional link that allows for expression of the heterologous nucleotide sequence of interest. Operably linked elements may be contiguous or non-contiguous. When used to refer to the joining of two protein coding regions, by operably linked is intended that the coding regions are in the same reading frame. The cassette may additionally contain at least one additional gene to be co-transformed into the plant. Alternatively, the additional gene(s) can be provided on multiple expression cassettes or DNA constructs. The expression cassette may additionally contain selectable marker genes.

In this manner, the nucleotide sequences encoding the ERF transcription factor proteins of the invention are provided in expression cassettes or expression constructs along with a promoter sequence of interest, typically a heterologous promoter sequence, for expression in the plant of interest. By "heterologous promoter sequence" is intended to mean a sequence that is not naturally operably linked with the ERF transcription factor protein-encoding nucleotide sequence. While the ERF transcription factor protein-encoding nucleotide sequence and the promoter sequence are heterologous to each other, either the ERF transcription factor protein-encoding nucleotide sequence or the heterologous promoter sequence may be homologous, or native, or heterologous, or foreign, to the plant host. It is recognized that the promoter may also drive expression of its homologous or native nucleotide sequence. In this case, the transformed plant will have a change in phenotype.

Fragments and variants of the polynucleotides and amino acid sequences of the present invention may also be expressed by promoters that are operable in plant cells. By "fragment" is intended a portion of the polynucleotide or a portion of the amino acid sequence. "Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. Generally, variants of a particular polynucleotide of the invention will have at least about 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein. Fragments and variants of the polynucleotides disclosed herein can encode proteins that retain transcription factor function.

"Variant" amino acid or protein is intended to mean an amino acid or protein derived from the native amino acid or protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active, that is they continue to possess the desired biological activity of the native protein, such as the ability to bind to genomic DNA and to modulate the expression of gene(s) near the DNA binding site. Biologically active variants of a native polypeptide will have at least about 80%, 85%, 90%, 91%, 92%, 93%, 94%, 95%, 96%, 97%, 98%, 99% or more sequence identity to the amino acid sequence for the native sequence as determined by sequence alignment programs and parameters described herein. In some embodiments, the variant polypeptide sequences will comprise conservative amino acid substitutions. The number of such conservative amino acid substitutions, summed with the number of amino acid identities, can be used to calculate the sequence positives when this sum is divided by the total number of amino acids in the sequence of interest. Sequence positive calculations are performed on the NCBI BLAST server that can be accessed on the world wide web at blast.ncbi.nlm.nih.gov/Blast.cgi. A biologically active variant of a protein of the invention may differ from that protein by as few as 1-15 amino acid residues, as few as 1-10, such as 6-10, as few as 5, as few as 4, 3, 2, or even 1 amino acid residue.

Amino acids can be generally categorized as aliphatic, hydroxyl or sulfur/selenium-containing, cyclic, aromatic, basic, or acidic and their amide. Without being limited by theory, conservative amino acid substitutions may be preferable in some cases to non-conservative amino acid substitutions for the generation of variant protein sequences, as conservative substitutions may be more likely than non-conservative substitutions to allow the variant protein to retain its biological activity. Polynucleotides encoding a polypeptide having one or more amino acid substitutions in the sequence are contemplated within the scope of the present invention. Table 1 below provides a listing of examples of amino acids belong to each class.

TABLE 1

Classes of Amino Acids

| Amino Acid Class | Example Amino Acids |
| --- | --- |
| Aliphatic | Gly, Ala, Val, Leu, Ile |
| Hydroxyl or sulfur/selenium-containing | Ser, Cys, Thr, Met, Sec |
| Cyclic | Pro |
| Aromatic | Phe, Tyr, Trp |
| Basic | His, Lys, Arg |
| Acidic and their Amide | Asp, Glu, Asn, Gln |

Variant sequences may also be identified by analysis of existing databases of sequenced genomes. In this manner, corresponding sequences can be identified and used in the methods of the invention.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Such genes and coding regions can be codon optimized for expression in a plant of interest. A "codon-optimized gene" is a gene having its frequency of codon usage designed to mimic the frequency of preferred codon usage of the host cell. Nucleic acid molecules can be codon optimized, either wholly or in part. Because any one amino acid (except for methionine and tryptophan) is encoded by a number of codons, the sequence of the nucleic acid molecule may be changed without changing the encoded amino acid. Codon optimization is when one or more codons are altered at the nucleic acid level such that the amino acids are not changed but expression in a particular host organism is increased. Those having ordinary skill in the art will recognize that codon tables and other references providing preference information for a wide range of organisms are available in the art (see, e.g., Zhang et al. (1991) *Gene* 105:61-72; Murray et al. (1989) *Nucl. Acids Res.* 17:477-508). Methodology for optimizing a nucleotide sequence for expression in a plant is provided, for example, in U.S. Pat.

No. 6,015,891, and the references cited therein, as well as in WO 2012/142,371, and the references cited therein.

The nucleotide sequences of the invention may be used in recombinant polynucleotides. A "recombinant polynucleotide" comprises a combination of two or more chemically linked nucleic acid segments which are not found directly joined in nature. By "directly joined" is intended the two nucleic acid segments are immediately adjacent and joined to one another by a chemical linkage. In specific embodiments, the recombinant polynucleotide comprises a polynucleotide of interest or active variant or fragment thereof such that an additional chemically linked nucleic acid segment is located either 5', 3' or internal to the polynucleotide of interest. Alternatively, the chemically-linked nucleic acid segment of the recombinant polynucleotide can be formed by deletion of a sequence. The additional chemically linked nucleic acid segment or the sequence deleted to join the linked nucleic acid segments can be of any length, including for example, 1, 2, 3, 4, 5, 6, 7, 8, 9, 10, 15, 20 or greater nucleotides. Various methods for making such recombinant polynucleotides are disclosed herein, including, for example, by chemical synthesis or by the manipulation of isolated segments of polynucleotides by genetic engineering techniques. In specific embodiments, the recombinant polynucleotide can comprise a recombinant DNA sequence or a recombinant RNA sequence. A "fragment of a recombinant polynucleotide" comprises at least one of a combination of two or more chemically linked amino acid segments which are not found directly joined in nature.

By "altering" or "modulating" the expression level of a gene is intended that the expression of the gene is upregulated or downregulated. It is recognized that in some instances, plant growth and yield are increased by increasing the expression levels of one or more genes encoding ERF transcription factor proteins, i.e. upregulating expression. Likewise, in some instances, plant growth and yield may be increased by decreasing the expression levels of one or more genes encoding ERF transcription factor proteins, i.e. downregulating expression. Thus, the invention encompasses the upregulation or downregulation of one or more genes encoding ERF transcription factor proteins. Further, the methods include the upregulation of at least one gene encoding a ERF transcription factor protein and the downregulation of at least one gene encoding a second ERF transcription factor protein in a plant of interest. By modulating the concentration and/or activity of at least one of the genes encoding an ERF transcription factor protein in a transgenic plant is intended that the concentration and/or activity is increased or decreased by at least about 1%, about 5%, about 10%, about 20%, about 30%, about 40%, about 50%, about 60%, about 70%, about 80%, or about 90% or greater relative to a native control plant, plant part, or cell which did not have the sequence of the invention introduced.

It is recognized that the expression levels of the genes encoding ERF transcription factor proteins of the present invention can be controlled by the use of one or more promoters that are functional in a plant cell. The expression level of the ERF transcription factor protein-encoding gene of interest may be measured directly, for example, by assaying for the level of the ERF transcription factor gene transcript or of the encoded protein in the plant. Methods for such assays are well-known in the art. For example, Northern blotting or quantitative reverse transcriptase-PCR (qRT-PCR) may be used to assess transcript levels, while western blotting, ELISA assays, or enzyme assays may be used to assess protein levels. ERF transcription factor function can be assessed by measuring the expression levels of gene(s) regulated by said ERF transcription factor.

A "subject plant or plant cell" is one in which genetic alteration, such as transformation, has been effected as to an ERF transcription factor protein-encoding gene of interest, or is a plant or plant cell which is descended from a plant or cell so altered and which comprises the alteration. A "control" or "control plant" or "control plant cell" provides a reference point for measuring changes in phenotype of the subject plant or plant cell. Thus, the expression levels of an ERF transcription factor protein-encoding gene of interest are higher or lower than those in the control plant depending on the methods of the invention.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

While the invention is described in terms of transformed plants, it is recognized that transformed organisms of the invention also include plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

To downregulate expression of an ERF transcription factor protein-encoding gene of interest, antisense constructions, complementary to at least a portion of the messenger RNA (mRNA) for the sequences of a gene of interest, particularly a gene encoding an ERF transcription factor protein of interest can be constructed. Antisense nucleotides are designed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85%, 90%, 95% or greater sequence identity to the corresponding sequences to be silenced may be used. Furthermore, portions of the antisense nucleotides may be used to disrupt the expression of the target gene.

The polynucleotides of the invention can be used to isolate corresponding sequences from other plants. In this manner, methods such as PCR, hybridization, and the like can be used to identify such sequences based on their sequence homology or identity to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have transcription factor activities and which share at least 75% sequence identity to the sequences disclosed herein, or to variants or fragments thereof, are encompassed by the present invention.

Variant sequences can be isolated by PCR. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York).

Variant sequences may also be identified by analysis of existing databases of sequenced genomes. In this manner, corresponding sequences encoding ERF transcription factor proteins can be identified and used in the methods of the invention. The variant sequences will retain the biological activity of an ERF transcription factor protein (i.e., an ability to bind to DNA and thereby to modulate the expression of gene(s) near the DNA binding site). The present invention shows that, unexpectedly, certain novel expression strategies for ERF transcription factor overexpression can lead to increased biomass and seed yield.

The expression cassette will include in the 5'-3' direction of transcription, a transcriptional and translational initiation region, a polynucleotide encoding an ERF transcription factor protein of the present invention, and a transcriptional and translational termination region (i.e., termination region) functional in plants.

A number of promoters may be used in the practice of the invention. The polynucleotides encoding an ERF transcription factor protein of the invention may be expressed from a promoter with a constitutive expression profile. Constitutive promoters include the CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like.

Polynucleotides of the invention encoding ERF transcription factor proteins of the invention may be expressed from tissue-preferred promoters. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Leaf-preferred promoters are also known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Developmentally-regulated promoters may be desirable for the expression of a polynucleotide encoding an ERF transcription factor protein. Such promoters may show a peak in expression at a particular developmental stage. Such promoters have been described in the art, e.g., U.S. 62/029,068; Gan and Amasino (1995) *Science* 270: 1986-1988; Rinehart et al. (1996) *Plant Physiol* 112: 1331-1341; Gray-Mitsumune et al. (1999) *Plant Mol Biol* 39: 657-669; Beaudoin and Rothstein (1997) *Plant Mol Biol* 33: 835-846; Genschik et al. (1994) *Gene* 148: 195-202, and the like.

Promoters that are induced following the application of a particular biotic and/or abiotic stress may be desirable for the expression of a polynucleotide encoding an ERF transcription factor protein. Such promoters have been described in the art, e.g., Yi et al. (2010) *Planta* 232: 743-754; Yamaguchi-Shinozaki and Shinozaki (1993) *Mol Gen Genet* 236: 331-340; U.S. Pat. No. 7,674,952; Rerksiri et al. (2013) *Sci World J* 2013: Article ID 397401; Khurana et al. (2013) *PLoS One* 8: e54418; Tao et al. (2015) *Plant Mol Biol Rep* 33: 200-208, and the like.

Cell-preferred promoters may be desirable for the expression of a polynucleotide encoding an ERF transcription factor protein. Such promoters may preferentially drive the expression of a downstream gene in a particular cell type such as a mesophyll or a bundle sheath cell. Such cell-preferred promoters have been described in the art, e.g., Viret et al. (1994) *Proc Natl Acad USA* 91: 8577-8581; U.S. Pat. Nos. 8,455,718; 7,642,347; Sattarzadeh et al. (2010) *Plant Biotechnol J* 8: 112-125; Engelmann et al. (2008) *Plant Physiol* 146: 1773-1785; Matsuoka et al. (1994) *Plant J* 6: 311-319, and the like.

It is recognized that a specific, non-constitutive expression profile may provide an improved plant phenotype relative to constitutive expression of a gene or genes of interest. For instance, many plant genes are regulated by light conditions, the application of particular stresses, the circadian cycle, or the stage of a plant's development. These expression profiles may be important for the function of the gene or gene product in planta. One strategy that may be used to provide a desired expression profile is the use of synthetic promoters containing cis-regulatory elements that drive the desired expression levels at the desired time and place in the plant. Cis-regulatory elements that can be used to alter gene expression in planta have been described in the scientific literature (Vandepoele et al. (2009) *Plant Physiol* 150: 535-546; Rushton et al. (2002) *Plant Cell* 14: 749-762). Cis-regulatory elements may also be used to alter promoter expression profiles, as described in Venter (2007) *Trends Plant Sci* 12: 118-124.

It is recognized that novel promoters may be identified through the analysis of large-scale biological data (Wang et al. (2016) *Front Plant Sci* 7:766; Alexandrov et al. (2009) *Plant Mol Biol* 69:179-194; Rai et al. (2013) *Plant Biotechnol J* 11:953-963; Batut and Gingeras (2013) *Curr Protoc Mol Biol* 104:Unit-25B.11; Yin et al. (2014) *Gene* 546:177-186). Large-scale biological data suitable for promoter identification may include microarray data, RNA-Seq data, or other large-scale datasets including transcriptomic data. Promoters with a desired expression profile (e.g., promoters that drive cell-specific, stress-responsive, tissue-specific, or other desired expression profile) may be derived by identifying genes or gene sets whose expression matches the desired expression profile; promoters are located upstream of these transcripts and may be isolated using standard molecular biology approaches.

Plant terminators are known in the art and include those available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

As indicated, the nucleotides encoding ERF transcription factor proteins of the present invention can be used in expression cassettes to transform plants of interest. Transformation protocols as well as protocols for introducing polypeptides or polynucleotide sequences into plants may vary depending on the type of plant or plant cell, i.e., monocot or dicot, targeted for transformation. The term "transform" or "transformation" refers to any method used to introduce polypeptides or polynucleotides into plant cells. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, U.S. Pat. Nos. 4,945,050; 5,879,918; 5,886,244; and, 5,932,782; Tomes et al. (1995) in Plant Cell, Tissue, and Organ Culture: Fundamental Methods, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783; and, 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in The Experimental Manipulation of Ovule Tissues, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference. "Stable transformation" is intended to mean that the nucleotide construct introduced into a plant integrates into the genome of the plant and is capable of being inherited by the progeny thereof.

The cells that have been transformed may be grown into plants in accordance with conventional ways. See, for example, McCormick et al. (1986) *Plant Cell Reports* 5:81-84. In this manner, the present invention provides transformed seed (also referred to as "transgenic seed") having a polynucleotide of the invention, for example, an expression cassette of the invention, stably incorporated into their genome.

The present invention may be used for transformation of any plant species, including, but not limited to, monocots and dicots. Examples of plant species of interest include, but are not limited to, corn (*Zea mays*), Brassica sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oil palm (*Elaeis guineensis*), poplar (*Populus* spp.), eucalyptus (*Eucalyptus* spp.), oats (*Avena sativa*), barley (*Hordeum vulgare*), vegetables, ornamentals, and conifers.

In one embodiment, a construct comprising a promoter that is operable in a plant cell, operably linked to a coding sequence encoding an ERF transcription factor protein of the present invention is used to transform a plant cell or cells. The transformed plant cell or cells are regenerated to produce transformed plants. These plants transformed with a construct comprising a functional promoter driving expression of an ERF transcription factor protein-encoding polynucleotide of the invention demonstrated increased plant yield, i.e., increased above-ground biomass and/or increased seed yield relative to control plants.

In one embodiment, a construct comprising a promoter that is operable in a plant cell, operably linked to a coding sequence encoding an ERF transcription factor protein of the present invention and further comprising at least one additional promoter that is operable in a plant cell, operably linked to at least one additional coding sequence, is used to transform a plant cell or cells. The additional coding sequence may encode, for instance, proteins involved in photosynthesis, cell wall biosynthesis, regulation of hydraulic conductivity, starch biosynthesis, starch degradation, sucrose biosynthesis, sucrose transport, nitrogen fixation, or other metabolic pathways of interest. The coding sequence encoding an ERF transcription factor and the additional coding sequence or additional coding sequences are both present in the genome of the transformed plant cell or cells. The transformed plant cell or cells are regenerated to produce transformed plants. These plants transformed with a construct comprising a functional promoter driving expression of an ERF transcription factor protein-encoding polynucleotide of the invention and further comprising at least one additional promoter that is operable in a plant cell, operably linked to at least one additional coding sequence demonstrated increased plant yield, i.e., increased aboveground biomass and/or increased seed yield relative to control plants.

Now that it has been demonstrated that upregulation of an ERF transcription factor gene increases plant yield, other methods for increasing expression of an endogenous ERF transcription factor sequence in a plant of interest can be used. The expression of an ERF transcription factor gene present in a plant's genome can be altered by inserting a transcriptional enhancer upstream of the ERF transcription factor gene present in the plant's genome. This strategy will allow the ERF transcription factor gene's expression to retain its normal developmental profile, while showing elevated transcript levels. This strategy will occur through the insertion of an enhancer element upstream of an ERF transcription factor gene of interest using a meganuclease designed against the genomic sequence of interest. Alternatively, a Cas9 endonuclease coupled with a guide RNA (gRNA) designed against the genomic sequence of interest, or a Cpf1 endonuclease coupled with a gRNA designed against the genomic sequence of interest, is used to effect the insertion of an enhancer element upstream of an ERF transcription factor gene of interest. Alternatively, a deactivated Cas9 endonuclease, or a deactivated Cpf1 endonuclease, C2c1 endonuclease, C2c2 endonuclease, or C2c3 endonuclease, fused to a transcriptional enhancer element is targeted to a genomic location near the transcription start site for an ERF transcription factor gene of interest, thereby modulating the expression of said ERF transcription factor gene of interest (Piatek et al. (2015) *Plant Biotechnol J* 13:578-589).

Modulation of the expression of an ERF transcription factor protein-encoding gene may be achieved through the use of precise genome-editing technologies to modulate the expression of the endogenous sequence. In this manner, a nucleic acid sequence will be inserted proximal to a native plant sequence encoding the ERF transcription factor through the use of methods available in the art. Such methods include, but are not limited to, meganucleases designed against the plant genomic sequence of interest (D'Halluin et al (2013) *Plant Biotechnol J* 11: 933-941); CRISPR-Cas9, CRISPR-Cpf1, TALENs, and other technologies for precise editing of genomes (Feng et al. (2013) *Cell Research* 23:1229-1232, Podevin et al. (2013) *Trends Biotechnology* 31: 375-383, Wei et al. (2013) *J Gen Genomics* 40: 281-289, Zhang et al (2013) WO 2013/026740, Zetsche et al. (2015) *Cell* 163:759-771, U.S. Provisional Patent Application 62/295,325); N. gregoryi Argonaute-mediated DNA insertion (Gao et al. (2016) *Nat Biotechnol* doi:10.1038/nbt.3547); Cre-lox site-specific recombination (Dale et al. (1995) *Plant J* 7:649-659; Lyznik, et al. (2007) *Transgenic Plant J* 1:1-9; FLP-FRT recombination (Li et al. (2009) *Plant Physiol* 151:1087-1095); Bxb1-mediated integration (Yau et al. (2011) *Plant J* 701:147-166); zinc-finger mediated integration (Wright et al. (2005) *Plant J* 44:693-705); Cai et al. (2009) *Plant Mol Biol* 69:699-709); and homologous recombination (Lieberman-Lazarovich and Levy (2011) *Methods Mol Biol* 701: 51-65; Puchta (2002) *Plant Mol Biol* 48:173-182). The insertion of said nucleic acid sequences will be used to achieve the desired result of overexpression, decreased expression, and/or altered expression profile of an ERF transcription factor gene.

Enhancers include any molecule capable of enhancing gene expression when inserted into the genome of a plant. Thus, an enhancer can be inserted in a region of the genome upstream or downstream of an ERF transcription factor sequence of interest to enhance expression. Enhancers may be cis-acting, and can be located anywhere within the genome relative to a gene for which expression will be enhanced. For example, an enhancer may be positioned within about 1 Mbp, within about 100 kbp, within about 50 kbp, about 30 kbp, about 20 kbp, about 10 kbp, about 5 kbp, about 3 kbp, or about 1 kbp of a coding sequence for which it enhances expression. An enhancer may also be located within about 1500 bp of a gene for which it enhances expression, or may be directly proximal to or located within an intron of a gene for which it enhances expression. Enhancers for use in modulating the expression of an endogenous gene encoding an ERF transcription factor protein or homolog according to the present invention include classical enhancer elements such as the CaMV 35S enhancer element, cytomegalovirus (CMV) early promoter enhancer element, and the SV40 enhancer element, and also intron-mediated enhancer elements that enhance gene expression such as the maize shrunken-1 enhancer element (Clancy and Hannah (2002) *Plant Physiol.* 130(2):918-29). Further examples of enhancers which may be introduced into a plant genome to modulate expression include a PetE enhancer (Chua et al. (2003) *Plant Cell* 15:11468-1479), or a rice α-amylase enhancer (Chen et al. (2002) *J. Biol. Chem.* 277:13641-13649), or any enhancer known in the art (Chudalayandi (2011) *Methods Mol. Biol.* 701:285-300). In some embodiments, the present invention comprises a subdomain, fragment, or duplicated enhancer element (Benfrey et al. (1990) *EMBO J* 9:1677-1684).

Alteration of ERF transcription factor gene expression may also be achieved through the modification of DNA in a way that does not alter the sequence of the DNA. Such changes could include modifying the chromatin content or structure of the ERF transcription factor gene of interest and/or of the DNA surrounding the ERF transcription factor gene. It is well known that such changes in chromatin content or structure can affect gene transcription (Hirschhorn et al. (1992) *Genes and Dev* 6:2288-2298; Narlikar et al. (2002) *Cell* 108: 475-487). Such changes could also include altering the methylation status of the ERF transcription factor gene of interest and/or of the DNA surrounding the ERF transcription factor gene of interest. It is well known that such changes in DNA methylation can alter transcription (Hsieh (1994) *Mol Cell Biol* 14: 5487-5494). Targeted epigenome editing has been shown to affect the transcription of a gene in a predictable manner (Hilton et al. (2015) 33: 510-517). It will be obvious to those skilled in the art that other similar alterations (collectively termed "epigenetic alterations") to the DNA that regulates transcription of the ERF transcription factor gene of interest may be applied in order to achieve the desired result of an altered ERF transcription factor gene expression profile.

Alteration of ERF transcription factor gene expression may also be achieved through the use of transposable element technologies to alter gene expression. It is well understood that transposable elements can alter the expression of nearby DNA (McGinnis et al. (1983) *Cell* 34:75-84). Alteration of the expression of a gene encoding an ERF transcription factor may be achieved by inserting a transposable element upstream of the ERF transcription factor gene of interest, causing the expression of said gene to be altered.

Alteration of ERF transcription factor gene expression may also be achieved through the insertion of a promoter upstream of the open reading frame encoding a native ERF transcription factor in the plant species of interest. This will occur through the insertion of a promoter of interest upstream of an ERF transcription factor protein-encoding open reading frame using a meganuclease designed against the genomic sequence of interest. This strategy is well-understood and has been demonstrated previously to insert a transgene at a predefined location in the cotton genome (D'Halluin et al. (2013) *Plant Biotechnol J* 11: 933-941). It will be obvious to those skilled in the art that other technologies can be used to achieve a similar result of insertion of genetic elements at a predefined genomic locus by causing a double-strand break at said predefined genomic locus and providing an appropriate DNA template for insertion (e.g., CRISPR-Cas9, CRISPR-Cpf1, TALENs, and other technologies for precise editing of genomes).

The following examples are offered by way of illustration and not by way of limitation. All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

EXPERIMENTAL

Example 1—Construction of ERF Transcription Factor Plant Transformation Vectors

Open reading frames encoding ERF transcription factors BRADI3G31600.1 (SEQ ID NO:1, encoding the protein sequence of SEQ ID NO:2), BRADI5G18850.1 (SEQ ID NO:56, encoding the protein sequence of SEQ ID NO:57), BRADI3G51610.1 (SEQ ID NO:58, encoding the protein sequence of SEQ ID NO:59), BRADI3G08790.1 (SEQ ID NO:60, encoding the protein sequence of SEQ ID NO:61), BRADI4G21265.1 (SEQ ID NO:62, encoding the protein sequence of SEQ ID NO:63), and BRADI3G45997.1 (SEQ ID NO:64, encoding the protein sequence of SEQ ID NO:65) were synthesized. Appropriate restriction sites were included at the 5' and 3' ends of the coding sequences to allow this DNA to be cloned into plant transformation vectors that contained genetic elements suitable for controlling gene expression. In each plant transformation construct, the ERF transcription factor open reading frame was located downstream of a plant promoter and 5' untranslated region (5'UTR) and upstream of a 3'UTR. Table 2 summarizes the plant transformation constructs that were built containing an ERF transcription factor open reading frame.

TABLE 2

ERF transcription factor plant transformation constructs

| Construct | Promoter + 5'UTR | ORF (DNA/Protein) | 3'UTR |
|---|---|---|---|
| 130297 | ZmUbi (SEQ ID NO: 3) | BRADI3G31600.1 (SEQ ID NO: 1/SEQ ID NO: 2) | ZmUbi (SEQ ID NO: 4) |
| 130299 | BRADI1G37410 (SEQ ID NO: 5) | BRADI3G31600.1 (SEQ ID NO: 1/SEQ ID NO: 2) | BRADI1G37410 (SEQ ID NO: 6) |
| 130794 | ZmUbi (SEQ ID NO: 3) | BRADI3G31600.1 (SEQ ID NO: 1/SEQ ID NO: 2) | ZmUbi (SEQ ID NO: 4) |
| 130795 | BRADI1G37410 (SEQ ID NO: 5) | BRADI3G31600.1 (SEQ ID NO: 1/SEQ ID NO: 2) | BRADI1G37410 (SEQ ID NO: 6) |
| 130806 | ZmUbi (SEQ ID NO: 7) | BRADI3G31600.1 (SEQ ID NO: 1/SEQ ID NO: 2) | ZmUbi (SEQ ID NO: 4) |
| 130900 | BRADI1G37410 (SEQ ID NO: 5) | BRADI3G31600.1 (SEQ ID NO: 1/SEQ ID NO: 2) | BRADI1G37410 (SEQ ID NO: 6) |
| 130920 | 2x35S (SEQ ID NO: 8) | BRADI3G31600.1 (SEQ ID NO: 1/SEQ ID NO: 2) | 35S polyA (SEQ ID NO: 9) |
| 130929 | 2x35S (SEQ ID NO: 8) | BRADI3G31600.1 (SEQ ID NO: 1/SEQ ID NO: 2) | 35S polyA (SEQ ID NO: 9) |
| 130977 | BRADI1G37410 (SEQ ID NO: 5) | BRADI3G31600.1 (SEQ ID NO: 1/SEQ ID NO: 2) | BRADI1G37410 (SEQ ID NO: 6) |
| 130119 | ZmUbi (SEQ ID NO: 3) | BRADI5G18850.1 (SEQ ID NO: 56/SEQ ID NO: 57) | ZmUbi (SEQ ID NO: 4) |
| 130130 | BRADI1G37410 (SEQ ID NO: 5) | BRADI5G18850.1 (SEQ ID NO: 56/SEQ ID NO: 57) | BRADI1G37410 (SEQ ID NO: 6) |
| 130930 | 2x35S (SEQ ID NO: 8) | BRADI5G18850.1 (SEQ ID NO: 56/SEQ ID NO: 57) | 35S polyA (SEQ ID NO: 9) |
| 131048 | BRADI1G37410 (SEQ ID NO: 5) | BRADI5G18850.1 (SEQ ID NO: 56/SEQ ID NO: 57) | BRADI1G37410 (SEQ ID NO: 6) |
| 130123 | ZmUbi (SEQ ID NO: 3) | BRADI3G08790.1 (SEQ ID NO: 60/SEQ ID NO: 61) | ZmUbi (SEQ ID NO: 4) |
| 130132 | BRADI1G37410 (SEQ ID NO: 5) | BRADI3G08790.1 (SEQ ID NO: 60/SEQ ID NO: 61) | BRADI1G37410 (SEQ ID NO: 6) |
| 130932 | 2x35S (SEQ ID NO: 8) | BRADI3G08790.1 (SEQ ID NO: 60/SEQ ID NO: 61) | 35S polyA (SEQ ID NO: 9) |
| 131050 | BRADI1G37410 (SEQ ID NO: 5) | BRADI3G08790.1 (SEQ ID NO: 60/SEQ ID NO: 61) | BRADI1G37410 (SEQ ID NO: 6) |
| 130125 | ZmUbi (SEQ ID NO: 3) | BRADI4G21265.1 (SEQ ID NO: 62/SEQ ID NO: 63) | ZmUbi (SEQ ID NO: 4) |
| 130133 | BRADI1G37410 (SEQ ID NO: 5) | BRADI4G21265.1 (SEQ ID NO: 62/SEQ ID NO: 63) | BRADI1G37410 (SEQ ID NO: 6) |
| 130933 | 2x35S (SEQ ID NO: 8) | BRADI4G21265.1 (SEQ ID NO: 62/SEQ ID NO: 63) | 35S polyA (SEQ ID NO: 9) |
| 131051 | BRADI1G37410 (SEQ ID NO: 5) | BRADI4G21265.1 (SEQ ID NO: 62/SEQ ID NO: 63) | BRADI1G37410 (SEQ ID NO: 6) |
| 130127 | ZmUbi (SEQ ID NO: 3) | BRADI3G45997.1 (SEQ ID NO: 64/SEQ ID NO: 65) | ZmUbi (SEQ ID NO: 4) |

TABLE 2-continued

ERF transcription factor plant transformation constructs

| Construct | Promoter + 5'UTR | ORF (DNA/Protein) | 3'UTR |
|---|---|---|---|
| 130134 | BRADI1G37410 (SEQ ID NO: 5) | BRADI3G45997.1 (SEQ ID NO: 64/SEQ ID NO: 65) | BRADI1G37410 (SEQ ID NO: 6) |
| 130934 | 2x35S (SEQ ID NO: 8) | BRADI3G45997.1 (SEQ ID NO: 64/SEQ ID NO: 65) | 35S polyA (SEQ ID NO: 9) |
| 131052 | BRADI1G37410 (SEQ ID NO: 5) | BRADI3G45997.1 (SEQ ID NO: 64/SEQ ID NO: 65) | BRADI1G37410 (SEQ ID NO: 6) |
| 130121 | ZmUbi (SEQ ID NO: 3) | BRADI3G51610.1 (SEQ ID NO: 58/SEQ ID NO: 59) | ZmUbi (SEQ ID NO: 4) |
| 130131 | BRADI1G37410 (SEQ ID NO: 5) | BRADI3G51610.1 (SEQ ID NO: 58/SEQ ID NO: 59) | BRADI1G37410 (SEQ ID NO: 6) |
| 130931 | 2x35S (SEQ ID NO: 8) | BRADI3G51610.1 (SEQ ID NO: 58/SEQ ID NO: 59) | 35S polyA (SEQ ID NO: 9) |
| 131049 | BRADI1G37410 (SEQ ID NO: 5) | BRADI3G51610.1 (SEQ ID NO: 58/SEQ ID NO: 59) | BRADI1G37410 (SEQ ID NO: 6) |
| 132138 | BRADI1G37410 (SEQ ID NO: 5) | BRADI3G51610.1 (SEQ ID NO: 58/SEQ ID NO: 59) | BRADI1G37410 (SEQ ID NO: 6) |
| 132142 | 2x35S (SEQ ID NO: 8) | BRADI3G51610.1 (SEQ ID NO: 58/SEQ ID NO: 59) | 35S polyA (SEQ ID NO: 9) |

In addition to the single-genic ERF transcription factor plant transformation constructs listed in Table 2, multigenic plant transformation constructs containing a ERF transcription factor gene cassette and a second linked cassette were also built. Table 3 summarizes the multigenic ERF transcription factor plant transformation constructs.

TABLE 3

ERF transcription factor multigenic plant transformation constructs

| Construct | Promoter + 5'UTR | ORF (DNA/Protein) | 3'UTR | Promoter + 5'UTR2 | ORF2 (DNA/Protein) | 3'UTR2 |
|---|---|---|---|---|---|---|
| 130234 | BRADI1G37410 (SEQ ID NO: 5) | BRADI3G31600.1 (SEQ ID NO: 1/ SEQ ID NO: 2) | BRADI1G37410 (SEQ ID NO: 6) | ZmRbcS (SEQ ID NO: 10) | RbcS-ictB (SEQ ID NO: 14/ SEQ ID NO: 15) | ZmRbcS (SEQ ID NO: 11) |
| 130622 | ZmUbi (SEQ ID NO: 7) | BRADI3G31600.1 (SEQ ID NO: 1/ SEQ ID NO: 2) | ZmUbi (SEQ ID NO: 4) | ZmRbcS (SEQ ID NO: 10) | RbcS-ictB (SEQ ID NO: 14/ SEQ ID NO: 15) | ZmRbcS (SEQ ID NO: 11) |
| 130623 | BRADI1G37410 (SEQ ID NO: 5) | BRADI3G31600.1 (SEQ ID NO: 1/ SEQ ID NO: 2) | BRADI1G37410 (SEQ ID NO: 6) | ZmRbcS (SEQ ID NO: 10) | RbcS-ictB (SEQ ID NO: 14/ SEQ ID NO: 15) | ZmRbcS (SEQ ID NO: 11) |
| 130797 | BRADI1G37410 (SEQ ID NO: 5) | BRADI3G31600.1 (SEQ ID NO: 1/ SEQ ID NO: 2) | BRADI1G37410 (SEQ ID NO: 6) | ZmRbcS (SEQ ID NO: 10) | RbcS-ictB (SEQ ID NO: 14/ SEQ ID NO: 15) | ZmRbcS (SEQ ID NO: 11) |
| 130855 | BRADI1G37410 (SEQ ID NO: 5) | BRADI3G31600.1 (SEQ ID NO: 1/ SEQ ID NO: 2) | BRADI1G37410 (SEQ ID NO: 6) | GluB-2 (SEQ ID NO: 12) | ism-2 (SEQ ID NO: 16/ SEQ ID NO: 17) | ZmUbi (SEQ ID NO: 4) |
| 130863 | BRADI1G37410 (SEQ ID NO: 5) | BRADI3G31600.1 (SEQ ID NO: 1/ SEQ ID NO: 2) | BRADI1G37410 (SEQ ID NO: 6) | 2x35S (SEQ ID NO: 8) | Poplar HC1 (SEQ ID NO: 18/ SEQ ID NO: 19) | 35S polyA (SEQ ID NO: 9) |
| 130864 | BRADI1G37410 (SEQ ID NO: 5) | BRADI3G31600.1 (SEQ ID NO: 1/ SEQ ID NO: 2) | BRADI1G37410 (SEQ ID NO: 6) | 2x35S (SEQ ID NO: 8) | Sorghum HC1 (SEQ ID NO: 20/ SEQ ID NO: 21) | 35S polyA (SEQ ID NO: 9) |
| 130871 | BRADI1G37410 (SEQ ID NO: 5) | BRADI3G31600.1 (SEQ ID NO: 1/ SEQ ID NO: 2) | BRADI1G37410 (SEQ ID NO: 6) | 2x35S (SEQ ID NO: 8) | Poplar HC1 (SEQ ID NO: 18/ SEQ ID NO: 19) | 35S polyA (SEQ ID NO: 9) |
| 130872 | BRADI1G37410 (SEQ ID NO: 5) | BRADI3G31600.1 (SEQ ID NO: 1/ SEQ ID NO: 2) | BRADI1G37410 (SEQ ID NO: 6) | 2x35S (SEQ ID NO: 8) | Sorghum HC1 (SEQ ID NO: 20/ SEQ ID NO: 21) | 35S polyA (SEQ ID NO: 9) |
| 130887 | BRADI1G37410 (SEQ ID NO: 5) | BRADI3G31600.1 (SEQ ID NO: 1/ SEQ ID NO: 2) | BRADI1G37410 (SEQ ID NO: 6) | ZmUbi (SEQ ID NO: 7) | RbcS-ictB (SEQ ID NO: 14/ SEQ ID NO: 15) | ZmRbcS (SEQ ID NO: 11) |
| 130888 | BRADI1G37410 (SEQ ID NO: 5) | BRADI3G31600.1 (SEQ ID NO: 1/ SEQ ID NO: 2) | BRADI1G37410 (SEQ ID NO: 6) | ZmRbcS (SEQ ID NO: 13) | ictB (SEQ ID NO: 54/ SEQ ID NO: 55) | ZmRbcS (SEQ ID NO: 11) |
| 130889 | BRADI1G37410 (SEQ ID NO: 5) | BRADI3G31600.1 (SEQ ID NO: 1/ SEQ ID NO: 2) | BRADI1G37410 (SEQ ID NO: 6) | ZmUbi (SEQ ID NO: 7) | RbcS-ictB (SEQ ID NO: 14/ SEQ ID NO: 15) | ZmUbi (SEQ ID NO: 4) |
| 130891 | BRADI1G37410 (SEQ ID NO: 5) | BRADI3G31600.1 (SEQ ID NO: 1/ SEQ ID NO: 2) | BRADI1G37410 (SEQ ID NO: 6) | ZmRbcS (SEQ ID NO: 13) | ictB (SEQ ID NO: 54/ SEQ ID NO: 55) | ZmRbcS (SEQ ID NO: 11) |
| 130892 | BRADI1G37410 (SEQ ID NO: 5) | BRADI3G31600.1 (SEQ ID NO: 1/ SEQ ID NO: 2) | BRADI1G37410 (SEQ ID NO: 6) | ZmRbcS (SEQ ID NO: 13) | RbcS-ictB (SEQ ID NO: 14/ SEQ ID NO: 15) | ZmRbcS (SEQ ID NO: 11) |

TABLE 3-continued

ERF transcription factor multigenic plant transformation constructs

| Construct | Promoter + 5'UTR | ORF (DNA/Protein) | 3'UTR | Promoter + 5'UTR2 | ORF2 (DNA/Protein) | 3'UTR2 |
|---|---|---|---|---|---|---|
| 130893 | BRADI1G37410 (SEQ ID NO: 5) | BRADI3G31600.1 (SEQ ID NO: 1/ SEQ ID NO: 2) | BRADI1G37410 (SEQ ID NO: 6) | ZmUbi (SEQ ID NO: 7) | RbcS-ictB (SEQ ID NO: 14/ SEQ ID NO: 15) | ZmUbi (SEQ ID NO: 4) |
| 132189 | BRADI1G37410 (SEQ ID NO: 5) | BRADI3G51610.1 (SEQ ID NO: 58/ SEQ ID NO: 59) | BRADI1G37410 (SEQ ID NO: 6) | ZmRbcS (SEQ ID NO: 10) | ictB (SEQ ID NO: 54/ SEQ ID NO: 55) | ZmRbcS (SEQ ID NO: 11) |

Three different promoters were used to drive expression of the ERF transcription factor gene in the constructs listed in Tables 2 and 3. While the ZmUbi promoter (SEQ ID NOs:3 and 7) and 2X355 promoter (SEQ ID NO:8) are well-characterized constitutive promoters, the BRADI1G37410 promoter (SEQ ID NO:5) is a novel promoter derived from analysis of B. distachyon gene expression following the application of various stresses (Priest et al. (2014) PLoS One 9:e87499). The BRADI1G37410 gene was found to be upregulated under drought and salt stress.

In addition to the gene cassettes described in Tables 2 and 3, each plant transformation construct listed in Tables 2 and 3 also contained a selectable marker cassette suitable for the selection of transformed plant cells and regeneration of plants following the introduction of the plant transformation vector, as described below. Each transformation vector was built in a plasmid that contained sequences suitable for plasmid maintenance in *E. coli* and in *Agrobacterium tumefaciens*. Following verification that the plant transformation constructs listed in Tables 2 and 3 contained the desired sequences, they were transformed into *A. tumefaciens* cells for plant transformation.

Example 2—Transformation of *Setaria viridis*

*A. tumefaciens* cells harboring ERF transcription factor plant transformation vectors were used to transform *S. viridis* cells according to a previously described method (PCT/US2015/43989, herein incorporated by reference). Following transformation of the *S. viridis* cells with the relevant plant transformation vectors and regeneration of *S. viridis* plants, PCR analyses were performed to confirm the presence of the gene(s) of interest in the *S. viridis* genome. Table 4 summarizes the transformation constructs used to transform *S. viridis*, along with the number of PCR-verified transgenic plants that resulted from transformation with each construct.

TABLE 4

Summary of *S. viridis* transformation with ERF transcription factor plant transformation vectors

| Construct | # Plants to Soil | selectable marker PCR (#) |
|---|---|---|
| 130299 | 11 | 7 |
| 130794 | 20 | 18 |
| 130871 | 21 | 19 |
| 130872 | 3 | 3 |
| 130929 | 19 | 18 |
| 130931 | 3 | 3 |
| 131049 | 18 | 18 |
| 130930 | 2 | 0 |
| 131048 | 17 | 17 |
| 130932 | 2 | 1 |

TABLE 4-continued

Summary of *S. viridis* transformation with ERF transcription factor plant transformation vectors

| Construct | # Plants to Soil | selectable marker PCR (#) |
|---|---|---|
| 131050 | 29 | 27 |
| 131051 | 6 | 6 |
| 131052 | 9 | 9 |

Example 3—Transformation of Maize (*Zea mays*)

*A. tumefaciens* cells harboring ERF transcription factor plant transformation vectors were used to transform maize (*Zea mays* cv. B104) cells suitable for regeneration on tissue culture medium. Following transformation of the maize cells with the relevant plant transformation vectors and regeneration of maize plants, PCR analyses were performed to confirm the presence of the gene(s) of interest in the maize genome. Table 5 summarizes the transformation constructs used to transform maize, along with the number of PCR-verified transgenic plants that resulted from transformation with each construct.

TABLE 5

Summary of maize transformation with ERF transcription factor plant transformation vectors

| Construct | # Transferred to Soil | Selectable Marker PCR+ |
|---|---|---|
| 130234 | 68 | 26 |
| 130299 | 51 | 42 |
| 130889 | 2 | 1 |

Example 4—Transformation of Rice (*Oryza sativa*)

*A. tumefaciens* cells harboring ERF transcription factor plant transformation vectors are used to transform rice (*Oryza sativa* cv. Kitaake) cells suitable for regeneration on tissue culture medium. Following transformation of the rice cells with the relevant plant transformation vectors and regeneration of rice plants, PCR analyses are performed to confirm the presence of the gene(s) of interest in the rice genome.

Example 5—Characterization of Transgenic *S. viridis*

Following the transformation and regeneration of *S. viridis* plants transformed with an ERF transcription factor plant transformation vector, the T0-generation plants were cultivated to maturity to produce T1-generation seeds. T1-generation *S. viridis* plants harboring the ERF transcription factor gene cassette of interest were grown in a greenhouse setting to assess the effects of ERF transcription factor gene expression on plant growth and terminal above-ground biomass and seed yield. A randomized block design was used with a wild-type *S. viridis* border row to eliminate edge effects from the analysis. Null segregant plants were grown alongside the transgenic *S. viridis* plants in identical environmental conditions. Table 6 summarizes the results of the biomass and seed yield determinations made from experiments with T1-generation *S. viridis* plants harboring a ERF transcription factor gene cassette as a result of transformation. This table indicates the construct used for transformation, as described in Tables 2 and 3, followed by the T0 event number from which the T1 seed was harvested.

TABLE 6

Summary of *S. viridis* greenhouse observations with T1-generation plants

| Event | DW | Seed Yield |
| --- | --- | --- |
| 131048-5A | −13.4% | −16.1% |
| 131048-6A | −12.9% | −19.3% |
| 131048-8A | −3.6% | −7.6% |
| 131048-9A | 9.0% | 9.4% |
| 131048-null | 0.0% | 0.0% |
| 131049-2B | −8.1% | −14.8% |
| 131049-3A | −0.5% | −5.5% |
| 131049-5A | 10.9% | 6.9% |
| 131049-6 | 12.0% | −3.8% |
| 131049-null | 0.0% | 0.0% |
| 130929-10 | 40.7% | 75.0% |
| 130929-12B | 11.7% | 17.2% |
| 130929-2 | 39.1% | 54.8% |
| 130929-9 | 44.9% | 58.5% |
| 130929-null | 0.0% | 0.0% |
| 130871-10A | 14.5% | 9.6% |
| 130871-4 | 22.9% | −2.6% |
| 130871-5A | 9.9% | 13.9% |
| 130871-5C | 25.1% | 21.7% |
| 130871-7 | 6.7% | 3.5% |
| 130871-null | 0.0% | 0.0% |

In Table 6, the dry weight (DW) and seed yield (measured by dry weight) are shown as percent change relative to null segregant plants derived from the same transformation construct used to generate the transgenic *S. viridis* plants harboring the ERF transcription factor gene cassette and other gene-of-interest cassettes. As this table shows, one out of four 131048 events showed increased dry weight accumulation and increased seed yield relative to null controls in the T1 generation. Two out of four 131049 events showed increased dry weight accumulation and one out of four 131049 events showed increased seed yield relative to null controls in the T1 generation. All four of the 130929 events showed increased biomass accumulation and seed yield relative to null controls in the T1 generation, and five out of five 130871 events showed increased biomass accumulation and seed yield relative to null controls.

Example 6—Characterization of Transgenic Maize

T0-generation maize plants transformed with the ERF transcription factor plant transformation vector of interest and confirmed to contain the gene(s) of interest are grown to maturity in a greenhouse. When the T0 plants reach reproductive stages, they are pollinated by an appropriate inbred maize line to produce hybrid maize seeds. Alternatively, or in addition to pollination of the T0 transgenic maize plant, the pollen from the T0 is used to pollinate one or more inbred maize lines to produce hybrid maize seeds. The F1-generation hybrid seed resulting from these pollinations are planted in a field setting in two- or four-row plots and cultivated using standard agronomic practices. Plants are genotyped to determine which plants do and which do not contain the ERF transcription factor gene cassette and any other relevant gene cassettes (e.g., a selectable marker gene cassette or expression cassettes for one or more additional genes of interest) that were included in the ERF transcription factor plant transformation vector. Following the maturation of the maize plants, the seed is harvested. Seeds from the plants containing the ERF transcription factor gene cassette are pooled, as are seeds from the null segregant plants lacking the ERF transcription factor gene cassette. The seeds are weighed, and seed yields are calculated for the plants containing the ERF transcription factor gene cassette as well as for the null segregant plants lacking the ERF transcription factor gene cassette. Appropriate statistical analyses are performed to determine whether plants containing a ERF transcription factor gene cassette produce higher yields than those plants that lack a ERF transcription factor gene cassette.

Alternatively, T0-generation maize plants transformed with the ERF transcription factor plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. Pollen from homozygous T1 plants is used to pollinate one or more inbred maize lines to produce hybrid maize seeds. Pollen from null segregant plants is also used to pollinate one or more inbred maize lines to produce hybrid maize seeds. The resulting hybrid seeds are planted in a field setting in two- or four-row plots and cultivated using standard agronomic practices. Following the maturation of the maize plants, the seed is harvested. Seeds from the plants containing the ERF transcription factor gene cassette are pooled, as are seeds from the null segregant plants lacking the ERF transcription factor gene cassette. The seeds are weighed, and seed yields are calculated for the plants containing the ERF transcription factor gene cassette as well as for the null segregant plants lacking the ERF transcription factor gene cassette. Appropriate statistical analyses are performed to determine whether plants containing a ERF transcription factor gene cassette produce higher yields than those plants that lack a ERF transcription factor gene cassette.

Example 7—Characterization of Transgenic Rice

T0-generation rice plants transformed with the ERF transcription factor plant transformation vector of interest and confirmed to contain the gene(s) of interest are grown to maturity in a greenhouse, then self-pollinated. The resulting T1 seeds are planted in a greenhouse and the T1 plants are cultivated. T1 plants are genotyped to identify homozygous, heterozygous, and null segregant plants. The plants from each group are grown to maturity and allowed to self-pollinate to produce T2 seed. The T2 seed resulting from this self-pollination is harvested and weighed, and seed yields from homozygous, heterozygous, and null segregant plants are calculated. Appropriate statistical analyses are performed to determine whether plants containing an ERF transcription factor gene cassette produce higher yields than those plants that lack an ERF transcription factor gene cassette.

T1-generation plants grown from seed that resulted from self-pollination of T0-generation plants, or T2-generation plants grown from seed that resulted from self-pollination of homozygous T1-generation plants, are grown in a field setting. In the case of T2-generation plants, null-segregant T1-generation plants are also self-pollinated to produce T2-generation null plants as negative controls. The plants are cultivated using standard agronomic practices and allowed to reach maturity. Upon reaching maturity, the plants are allowed to self-pollinate. The seed resulting from these self-pollinations is harvested and weighed, and seed yields from homozygous, heterozygous, and null segregant plants are calculated. Appropriate statistical analyses are performed to determine whether plants containing an ERF transcription factor gene cassette produce higher yields than those plants that lack an ERF transcription factor gene cassette.

I claim:

1. A transgenic plant cell having stably incorporated into its genome a promoter that drives expression in a plant cell operably linked to an ethylene response factor (ERF) transcription factor protein encoding-sequence, wherein said promoter is heterologous to said ERF transcription factor protein-encoding sequence, wherein said ERF transcription factor protein-encoding sequence encodes a protein having 95% amino acid sequence identity to the amino acid sequence as set forth in SEQ ID NO: 2, and wherein over-expression of said protein in a plant increases seed yield as compared to a control plant of the same species lacking said over-expression.

2. A transgenic plant regenerated from the transgenic plant cell of claim 1.

3. A transformed seed of the transgenic plant of claim 2.

4. The transgenic plant cell of claim 1, wherein said transgenic plant cell is from a monocot plant species.

5. The transgenic plant cell of claim 1, wherein said transgenic plant cell is from a dicot plant species.

6. The transgenic plant cell of claim 1, wherein said promoter that drives expression in a plant cell is selected from the group consisting of SEQ ID NO:5 and SEQ ID NO: 8.

7. A transgenic plant cell having stably incorporated into its genome a promoter that drives expression in a plant cell operably linked to an ethylene response factor (ERF) transcription factor protein encoding sequence, wherein said promoter is heterologous to said ERF transcription factor protein-encoding sequence, wherein said ERF transcription factor protein-encoding sequence encodes a protein having the amino acid sequence as set forth in SEQ ID NO: 2, and wherein over-expression of said protein in a plant increases seed yield as compared to a control plant of the same species lacking said over-expression.

8. A transgenic plant regenerated from the transgenic plant cell of claim 7.

9. A transformed seed of the transgenic plant of claim 8.

10. The transgenic plant cell of claim 7, wherein said transgenic plant cell is from a monocot plant species.

11. The transgenic plant cell of claim 7, wherein said transgenic plant cell is from a dicot plant species.

12. The transgenic plant cell of claim 7, wherein said promoter that drives expression in a plant cell is selected from the group consisting of SEQ ID NO:5 and SEQ ID NO: 8.

13. A transgenic plant having stably incorporated into its genome a promoter that drives expression in a plant cell operably linked to an ethylene response factor (ERF) transcription factor protein-encoding sequence, wherein said promoter is heterologous to said ERF transcription factor protein-encoding sequence, wherein said ERF transcription factor protein-encoding sequence encodes a protein having 95% amino acid sequence identity to the amino acid sequence as set forth in SEQ ID NO: 2 and wherein over-expression of said protein in the transgenic plant increases seed yield as compared to a control plant of the same species lacking said over-expression.

14. A transformed seed of the transgenic plant of claim 13.

15. The transgenic plant of claim 13, wherein said transgenic plant is from a monocot plant species.

16. The transgenic plant of claim 13, wherein said transgenic plant is from a dicot plant species.

17. The transgenic plant of claim 13, wherein said promoter that drives expression in a plant cell is selected from the group consisting of SEQ ID NO:5 and SEQ ID NO: 8.

18. The transgenic plant cell of claim 1, wherein said ERF transcription factor protein-encoding sequence comprises a nucleotide sequence having at least 95% nucleotide sequence identity to SEQ ID NO: 1.

19. The transgenic plant cell of claim 7, wherein said ERF transcription factor protein-encoding sequence comprises the nucleotide sequence as set forth in SEQ ID NO: 1.

20. The transgenic plant of claim 13, wherein said ERF transcription factor protein-encoding sequence comprises a nucleotide sequence having at least 95% nucleotide sequence identity to SEQ ID NO: 1.

* * * * *

SEQUENCE LISTING

```
<160> NUMBER OF SEQ ID NOS: 65

<210> SEQ ID NO 1
<211> LENGTH: 609
<212> TYPE: DNA
<213> ORGANISM: Brachypodium distachyon
<220> FEATURE:
<221> NAME/KEY: ERF_Transcription_Factor
<222> LOCATION: (1)..(609)

<400> SEQUENCE: 1
atggagcagc agggcaggga gatttctggc atgatgtctc tctgcggcag gagggctagg      60
gctgagacaa ggcatcctgt gtacaggggc gtgaggctca gggctggcaa gtgggtgtct     120
gagattaggg agctcaggaa gcctaatagg atttggctcg gcacataccc tacacctgag     180
atggctgctg ctgcttacga tgctgctgct ctcgctctca ggggcgctgg cacagctctc     240
aatttccctg atgctgctag gtctaggcct gctcctaggt ctgtgtctgc tgatgatgtg     300
agggctgctg ctgctgaggc tgctgcttct ttcgctgctg tggctacatc tgcttggaca     360
acaacaacag agaggtcttc tgatgatcag taccataggc ctcattgcaa tcagctcagg     420
ggcggcggcg atgtgatggg cgtggtggat gaggatgatg tgttcgagat gcctaggctc     480
atggcttcta tggctgaggg cctcatgatt tctcctcctg atggcggcgc tgtggctcct     540
tactacgatg tgctccaggt ggaggatgag ggcgatgctg ctgctgtgtc tctctgggat     600
catgcttga                                                              609

<210> SEQ ID NO 2
<211> LENGTH: 202
<212> TYPE: PRT
<213> ORGANISM: Brachypodium distachyon
<220> FEATURE:
<221> NAME/KEY: ERF_Transcription_Factor
<222> LOCATION: (1)..(202)

<400> SEQUENCE: 2

Met Glu Gln Gln Gly Arg Glu Ile Ser Gly Met Met Ser Leu Cys Gly
1               5                   10                  15

Arg Arg Ala Arg Ala Glu Thr Arg His Pro Val Tyr Arg Gly Val Arg
            20                  25                  30

Leu Arg Ala Gly Lys Trp Val Ser Glu Ile Arg Glu Leu Arg Lys Pro
        35                  40                  45

Asn Arg Ile Trp Leu Gly Thr Tyr Pro Thr Pro Glu Met Ala Ala Ala
    50                  55                  60

Ala Tyr Asp Ala Ala Ala Leu Ala Leu Arg Gly Ala Gly Thr Ala Leu
65                  70                  75                  80

Asn Phe Pro Asp Ala Ala Arg Ser Arg Pro Ala Pro Arg Ser Val Ser
                85                  90                  95

Ala Asp Asp Val Arg Ala Ala Ala Ala Glu Ala Ala Ala Ser Phe Ala
            100                 105                 110
```

```
Ala Val Ala Thr Ser Ala Trp Thr Thr Thr Glu Arg Ser Ser Asp
            115                 120                 125

Asp Gln Tyr His Arg Pro His Cys Asn Gln Leu Arg Gly Gly Asp
130                 135                 140

Val Met Gly Val Val Asp Glu Asp Asp Val Phe Glu Met Pro Arg Leu
145                 150                 155                 160

Met Ala Ser Met Ala Glu Gly Leu Met Ile Ser Pro Pro Asp Gly Gly
                165                 170                 175

Ala Val Ala Pro Tyr Tyr Asp Val Leu Gln Val Glu Asp Glu Gly Asp
                180                 185                 190

Ala Ala Ala Val Ser Leu Trp Asp His Ala
            195                 200

<210> SEQ ID NO 3
<211> LENGTH: 2161
<212> TYPE: DNA
<213> ORGANISM: Zea mays
<220> FEATURE:
<221> NAME/KEY: ZmUbi_promoter1
<222> LOCATION: (1)..(2161)

<400> SEQUENCE: 3
actatgaaga agcacaaaga atacgaggga tggtgcagag ccgaagctat gcgcaaaaga      60
gcttcggcgt gataacagaa aaggaaaccg acttaaaggg gaaagagacta tttagacccc    120
gatgggttac tatagagtta ttagcaaatg taaagggcat aggtgtaatt ttacatgggc    180
tgcgtctcgt gcctataaat agatgaacag tgctcccgta ctgttcacac ggactggaca    240
tttgcttttg cgtcacgctt gtacttttgg ctttttttcaa gccgaaggta catttgtaat    300
ttgttatcat ttctattttt ccataataat aaaatagaaa tgagttaacg ataatatttg    360
aggatttatg ttattcatac tttgcatgaa tcctttttca ttatttgtgg tattgatgaa    420
ggtatgccct tcataacctt tgtccaagac tcattatatc ccgagggaga taatgtttca    480
aaggacgaaa gactttaacg tttaacaatt tctgtgttgc cttgttctta attcatagca    540
tttaaggaca agttcccaac acatataaca tggtgaatag acgcatgcca caactctggt    600
tttgcaagaa cattaaaaca atggttttag agaggatggt ataccatagt actcaatgat    660
aaaggttttt tagttagttg agctccagaa ttcatagtta acagttaaca cttaacaata    720
atactacgcc tgtaccacatt gttcatcatc agaattcaga aggaaggtg agcggggaac    780
ccttttgtga cttctttttg tgatcagcta gccggtgatg gtggtaccat cagtggccag    840
cttttgttct agttcaacgg tcccggcctt ccggccacct aatgcaccaa ctattagtat    900
tgcagctagc cttcaaaaga aatgcatttg cagccgcctg tccctgtccc cgaccaatct    960
gctagcagac tcgcattatc gatggaggac actaataaat tcagccttcg atgtggatgc   1020
aacagcttca caggattcca ttaaatcgta gccgttgtgt caaagtttgc tttgccaacg   1080
ttatttattt atttatttag aaaaccagct ttgaccagcc gccctcttta cgtttggcac   1140
aatttagctg aatccggcgg catggcaagg tagactgcag tgcagcgtga cccggtcgtg   1200
cccctctcta gagataatga gcattgcatg tctaagttat aaaaaattac cacatatttt   1260
ttttgtcaca cttgtttgaa gtgcagttta tctatcttta tacatatatt taaactttac   1320
tctacgaata atataatcta tagtactaca ataatatcag tgttttagag aatcatataa   1380
atgaacagtt agacatggtc taaaggacaa ttgagtattt tgacaacagg actctacagt   1440
tttatctttt tagtgtgcat gtgttctcct ttttttttgc aaatagcttc acctatataa   1500
```

```
tacttcatcc attttattag tacatccatt tagggtttag ggttaatggt ttttatagac    1560
taattttttt agtacatcta ttttattcta ttttagcctc taaattaaga aaactaaaac    1620
tctattttag ttttttttatt taataattta gatataaaat agaataaaat aaagtgacta   1680
aaaattaaac aaatacccctt taagaaatta aaaaaactaa ggaaacattt ttcttgtttc   1740
gagtagataa tgccagcctg ttaaacgccg tcgacgagtc taacggacac caaccagcga   1800
accagcagcg tcgcgtcggg ccaagcgaag cagacggcac ggcatctctg tcgctgcctc   1860
tggacccctc tcgagagttc cgctccaccg ttggacttgc tccgctgtcg gcatccagaa   1920
attgcgtggc ggagcggcag acgtgagccg cacggcagg cggcctcctc ctcctctcac    1980
ggcaccggca gctacggggg gacaattcct ttcccaccgc tccttcgctt tcccttcctc   2040
gcccgccgta ataaatagac ccccctccca caccctcttt ccccaacctc gtgttgttcg   2100
gagcgcacac acacacaacc agatctcccc caaatccacc cgtcggcacc tccgcttcaa   2160
g                                                                  2161

<210> SEQ ID NO 4
<211> LENGTH: 623
<212> TYPE: DNA
<213> ORGANISM: Zea mays
<220> FEATURE:
<221> NAME/KEY: ZmUbi_3_UTR
<222> LOCATION: (1)..(623)

<400> SEQUENCE: 4
gtcatgggtc gtttaagctg ccgatgtgcc tgcgtcgtct ggtgccctct ctccatatgg     60
aggttgtcaa agtatctgct gttcgtgtca tgagtcgtgt cagtgttggt ttaataatgg    120
accggttgtg ttgtgtgtgc gtactaccca gaactatgac aaatcatgaa taagtttgat    180
gtttgaaatt aaagcctgtg ctcattatgt tctgtctttc agttgtctcc taatatttgc    240
ctgcaggtac tggctatcta ccgtttctta cttaggaggt gtttgaatgc actaaaacta    300
atagttagtg gctaaaatta gttaaaacat ccaaacacca tagctaatag ttgaactatt    360 agctatttttt ggaaaattag ttaatagtga ggtagttatt tgttagctag ctaattcaac   420
taacaatttt tagccaacta acaattagtt tcagtgcatt caaacacccc cttaatgtta    480
acgtggttct atctaccgtc tcctaatata tggttgattg ttcggttttgt tgctatgcta   540 ttgggttctg attgctgcta gttcttgctg aatccagaag ttctcgtagt atagctcaga    600
ttcatattat ttattttgagt gat                                          623

<210> SEQ ID NO 5
<211> LENGTH: 1054
<212> TYPE: DNA
<213> ORGANISM: Brachypodium distachyon
<220> FEATURE:
<221> NAME/KEY: BRADI1G37410_promoter
<222> LOCATION: (1)..(1054)

<400> SEQUENCE: 5
gcgacctgcc aatctgggat tgacagatgt tccttttttt taggggaggg ccttttcctt     60
cttcgagaaa cgagggttgg gggtaggatg atagttacc tgctttaggt cgcagacgaa     120
ttgcacaggg ccacaggccc gcccggccca cgtgatccgg tggaacaagc cgatttgcac    180
gcgcggtgcc ggagtcccga tttgccgccc aagcggaccc gatttgcccc agtgactcaa    240
tttctgggct gtgccccgtc agaactgctt tctgggctgg tctagtaggc tttactccgt    300
tcaacggggt gatattcctt atgatttact ctcccgtacc atgttcgaaa tattacatgt    360
```

| | |
|---|---:|
| acctagagat attttaatat ataaatacgt ctatatttaa tcatgagtca cttaatacga | 420 |
| gatggatgga gtatgatttt tgagtaaata gttttcaaa aaaataaaat aaagttttta | 480 |
| gcgcaaacga agtacctcat ggccgatcta accccatttc ctttgttcac ccaccttcat | 540 |
| gtcgtatcgt accatggaac ttgacaactc ttatgcgatc tattgaacaa actcaatttt | 600 |
| aatttctttt tttcttttcc tgtttcaaat gggaattcag atgtcgtggg ccattttcca | 660 |
| ttttgcgagc gaacgatagt tgtcatcctc cccaaatgtg tcatcgagca tgttccaga | 720 |
| ataagctgag acgtggcgac tccgacgcgt ctagtgcctg cacacgtctg gctagtcacc | 780 |
| agttcctgcc tgccggccca ctcctgtgac cacacgtagc tgcctaccgt ggcgctcgaa | 840 |
| tccctatccc ctccgcctcg aactgcttat aaatcggggc cccggcttca cttccctcca | 900 |
| ccagtccaca gacacagcca cgaatttgca gtgtacgcag ttctagtaaa caagaaccac | 960 |
| atttcctgag ggtgtacgat cagtgaagcg tttgtgcaag gacacaagaa ccacatttcc | 1020 |
| tgagggtgta cgatcagtga agcgtttgtg caag | 1054 |

```
<210> SEQ ID NO 6
<211> LENGTH: 258
<212> TYPE: DNA
<213> ORGANISM: Brachypodium distachyon
<220> FEATURE:
<221> NAME/KEY: BRADI1G37410_3_UTR
<222> LOCATION: (1)..(258)

<400> SEQUENCE: 6
```

| | |
|---|---:|
| gcgcctcgca gtcgcaggtt gcctagctcg acttgtgaga gttgagctac gtatagtacc | 60 |
| agctggccac cctctgagaa taatatactg taataagatg aagaagaata aaattcccac | 120 |
| gatcacatgt actgttatac tgagagtaga gtctgtaccg tgggatttat accggacgtc | 180 |
| gttgtgtaaa tttcctttta atttgtttga atcgtgaatc gtatatgtat gttcacatgt | 240 |
| acactgtgtt cttctgtt | 258 |

```
<210> SEQ ID NO 7
<211> LENGTH: 1992
<212> TYPE: DNA
<213> ORGANISM: Zea mays
<220> FEATURE:
<221> NAME/KEY: ZmUbi_promoter2
<222> LOCATION: (1)..(1992)

<400> SEQUENCE: 7
```

| | |
|---|---:|
| ctgcagtgca gcgtgacccg gtcgtgcccc tctctagaga taatgagcat tgcatgtcta | 60 |
| agttataaaa aattaccaca tatttttttt gtcacacttg tttgaagtgc agtttatcta | 120 |
| tctttataca tatatttaaa ctttactcta cgaataatat aatctatact actacaataa | 180 |
| tatcagtgtt ttagagaatc atataaatga acagttagac atggtctaaa ggacaattga | 240 |
| gtattttgac aacaggactc tacagtttta tcttttagt gtgcatgtgt tctccttttt | 300 |
| ttttgcaaat agcttcacct atataatact tcatccattt tattagtaca tccatttagg | 360 |
| gtttagggtt aatggttttt atagactaat tttttagta catctatttt attctatttt | 420 |
| agcctctaaa ttaagaaaac taaaactcta ttttagtttt tttatttaat aatttagata | 480 |
| taaatagaa taaataaag tgactaaaaa ttaaacaaat acccttaag aaattaaaaa | 540 |
| aactaaggaa acattttct tgtttcgagt agataatgcc agcctgttaa acgccgtcga | 600 |
| cgagtctaac ggacaccaac cagcgaacca gcagcgtcgc gtcgggccaa gcgaagcaga | 660 |
| cggcacggca tctctgtcgc tgcctctgga cccctctcga gagttccgct ccaccgttgg | 720 |

| acttgctccg ctgtcggcat ccagaaattg cgtggcggag cggcagacgt gagccggcac | 780 |
| ggcaggcggc ctcctcctcc tctcacggca cggcagctac gggggattcc tttcccaccg | 840 |
| ctccttcgct ttcccttcct cgcccgccgt aataaataga caccccctcc acaccctctt | 900 |
| tccccaacct cgtgttgttc ggagcgcaca cacacacaac cagatctccc ccaaatccac | 960 |
| ccgtcggcac ctccgcttca aggtacgccg ctcgtcctcc cccccccccc ctctctacct | 1020 |
| tctctagatc ggcgttccgg tccatggtta gggcccggta gttctacttc tgttcatgtt | 1080 |
| tgtgttagat ccgtgtttgt gttagatccg tgctgctagc gttcgtacac ggatgcgacc | 1140 |
| tgtacgtcag acacgttctg attgctaact tgccagtgtt tctctttggg aatcctggg | 1200 |
| atggctctag ccgttccgca gacgggatcg atttcatgat ttttttttgtt tcgttgcata | 1260 |
| gggtttggtt tgcccttttc ctttatttca atatatgccg tgcacttgtt tgtcgggtca | 1320 |
| tcttttcatg ctttttttttg tcttggttgt gatgatgtgg tctggttggg cggtcgttct | 1380 |
| agatcggagt agaattctgt ttcaaactac ctggtggatt tattaatttt ggatctgtat | 1440 |
| gtgtgtgcca tacatattca tagttacgaa ttgaagatga tggatggaaa tatcgatcta | 1500 |
| ggataggtat acatgttgat gcgggtttta ctgatgcata tacagagatg cttttttgttc | 1560 |
| gcttggttgt gatgatgtgg tgtggttggg cggtcgttca ttcgttctag atcggagtag | 1620 |
| aatactgttt caaactacct ggtgtattta ttaattttgg aactgtatgt gtgtgtcata | 1680 |
| catcttcata gttacgagtt taagatggat ggaaatatcg atctaggata ggtatacatg | 1740 |
| ttgatgtggg ttttactgat gcatatacat gatggcatat gcagcatcta ttcatatgct | 1800 |
| ctaaccttga gtacctatct attataataa acaagtatgt tttataatta ttttgatctt | 1860 |
| gatatacttg gatgatggca tatgcagcag ctatatgtgg attttttttag ccctgccttc | 1920 |
| atacgctatt tatttgcttg gtactgtttc ttttgtcgat gctcaccctg ttgtttggtg | 1980 |
| ttacttctgc ag | 1992 |

<210> SEQ ID NO 8
<211> LENGTH: 807
<212> TYPE: DNA
<213> ORGANISM: Cauliflower mosaic virus
<220> FEATURE:
<221> NAME/KEY: 2X35S_promoter
<222> LOCATION: (1)..(807)

<400> SEQUENCE: 8

| gcgtattggc tagagcagct tgccaacatg gtggagcacg acactctcgt ctactccaag | 60 |
| aatatcaaag atacagtctc agaagaccaa agggctattg agacttttca acaaagggta | 120 |
| atatcgggaa acctcctcgg attccattgc ccagctatct gtcacttcat caaaaggaca | 180 |
| gtagaaaagg aaggtggcac ctacaaatgc catcattgcg ataaaggaaa ggctatcgtt | 240 |
| caagatgcct ctgccgacag tggtcccaaa gatggacccc cacccacgag gagcatcgtg | 300 |
| gaaaaagaag acgttccaac cacgtcttca agcaagtgg attgatgtga acatggtgga | 360 |
| gcacgacact ctcgtctact ccaagaatat caaagataca gtctcagaag accaaagggc | 420 |
| tattgagact tttcaacaaa gggtaatatc gggaaacctc ctcggattcc attgcccagc | 480 |
| tatctgtcac ttcatcaaaa ggacagtaga aaggaaggt ggcacctaca aatgccatca | 540 |
| ttgcgataaa ggaaaggcta tcgttcaaga tgcctctgcc gacagtggtc ccaaagatgg | 600 |
| acccccaccc acgaggagca tcgtggaaaa agaagacgtt ccaaccacgt cttcaaagca | 660 |
| agtggattga tgtgatatct ccactgacgt aagggatgac gcacaatccc actatccttc | 720 |

```
gcaagaccct tcctctatat aaggaagttc atttcatttg gagaggacac gctgaaatca    780
ccagtctctc tctacaaatc tatctct                                        807
```

<210> SEQ ID NO 9
<211> LENGTH: 209
<212> TYPE: DNA
<213> ORGANISM: Cauliflower mosaic virus
<220> FEATURE:
<221> NAME/KEY: 35S_polyA
<222> LOCATION: (1)..(209)

<400> SEQUENCE: 9

```
gatctgtcga tcgacaagct cgagtttctc cataataatg tgtgagtagt tcccagataa     60
gggaattagg gttcctatag ggtttcgctc atgtgttgag catataagaa acccttagta    120
tgtatttgta tttgtaaaat acttctatca ataaaatttc taattcctaa aaccaaaatc    180
cagtactaaa atccagatcc cccgaatta                                      209
```

<210> SEQ ID NO 10
<211> LENGTH: 912
<212> TYPE: DNA
<213> ORGANISM: Zea mays
<220> FEATURE:
<221> NAME/KEY: ZmRbcS_promoter1
<222> LOCATION: (1)..(912)

<400> SEQUENCE: 10

```
gagctccctt taatctggcg ctagatctgc atccgcggct tgcaaagata aatggcacat     60
ttagtgtgtt attttgcaat acctttcata gtagatatcc ttaaatgcag ttttaggcat    120
gtttgggtaa ttaaataaca tttttaggag gagtttttaga tttacctttc tttcgtgatg    180
actgatgaca gacgtgggga attcaaatgc aactctagcg aaagttcata tatttttcat    240
aaatagctga ggctggggta attatttttt ttgtagaaaa atagaatagg tggaatggtt    300
ggggaaggcg taggcgctcg tggacgacgc ccgataaaag acaagaggcg gaattgccat    360
gaattcgagg tagctaagta aggcgcatat atatgccaaa aaattctact gtcactttcc    420
aatttcaatg cgctgccaaa caagccatcc tggaaactga cttgaattca gcccaattct    480
gtagatccaa acagggccgg cgtcagtgcc tcaggtgaga gagcagcaga cgatgcaaag    540
agccaaaact gcaagcagac gcagccgaag ccgaagccga agcccaagcc caaaactgtt    600
ttgtctttgc ccagaaccgc gacgagccta aactgcgctt cctcctatct acaagtccct    660
ggcacatcac gcatagtcca accatggcgc gcaggcgata aggcgcgcca cggggacgcg    720
acatgtggtg gcggacgcga tcaggatagg gccaggctgg ccgggcgcgg ccacgggaga    780
acggtggcca ctcgtcccac atccgcttcg tcctgtcctg tactgcgtcc tgcccccaac    840
gagagccgga gccggccatc ccgtcgcaca ctctccccct ctatatatgc cgtcggtgtg    900
ggggagccta ct                                                        912
```

<210> SEQ ID NO 11
<211> LENGTH: 435
<212> TYPE: DNA
<213> ORGANISM: Zea mays
<220> FEATURE:
<221> NAME/KEY: ZmRbcS_3_UTR
<222> LOCATION: (1)..(435)

<400> SEQUENCE: 11

```
cgcccgccgg ccgcccccg cggctagct agctagctag ctcctgcgtg agctagtagc      60
tagtgccatg cgtcgtctct gtcgttcggt tttgcttcgg gtcaccgtgt acccttttgct   120
tgcttggttt cttcttcct tttttcttt tttttcttc ttttccccgg ccatggttcc      180
tttgctttcc agcagttctc tgctggatgt gatgtatcca ttgttgcaat catggccttg   240
cattggctac ctctatacct gctacaaaac tactgcaacg cctatatata cttggggtga   300
ggaacatgtg aatgcaagct ccggctatca tatacatgta atatggatac aaactatata   360
tataaatccg ccgaggcgcc gacaatacta tacgacaccg tgttaagtta atatataact   420
ggtgcttttt attta                                                    435
```

<210> SEQ ID NO 12
<211> LENGTH: 2300
<212> TYPE: DNA
<213> ORGANISM: Oryza sativa
<220> FEATURE:
<221> NAME/KEY: OsGluB-2_promoter
<222> LOCATION: (1)..(2300)

<400> SEQUENCE: 12

```
agaaggagag gaataaataa ggagaggaat agagataagg ttgaggagag gagttaaagg     60
agagaggaga taaggttgag gagaggagga gatggcctcg atccgatcgc gcacgcctct   120
ccgatctccg cgtcgatctt ttttcccggt tggtaacacc aaccggtact aaagattgaa   180
aagtaccctg gagcttttaa accgggacaa gatgttaata caactgggac tattgtgaaa   240
tctggtcgac cgatcaaaga tggtttctcc accagtgtat gtattttact cattggatta   300
acattttaca agagaccaat acttttagga tgggataaga caaagtattt catgataatc   360
tagccggtca tattttagaa tgatggacat ataccatagt ttcaggtctt ttgctctatc   420
attcgatgac aatgctgcta gttattaata ctaaacattt atattactac atatatgtta   480
ttttttact caaaagaaaa actattaatc attcatggaa gcagcagcaa aaaccacaag   540
ggtagtattg tccatctctc tctctctccc ccccccctc tcccctctat cctctctttc   600
aggatttcgg cagccggcaa aactagccaa acacttttag ggccactttc aactcctact   660
agagttagag tttagagcta ggattcgaga gttagagctc tacctaatag gcctgaaata   720
tggatatcca atttcacatg tagtatctat ttcaaaattg gattggatta tgttataccca  780
aaaaagggat atggatattt agtggacagg agaagacatg tatggcccca caagttgtat   840
aaagtttccc ttctatataa taaatcatct caagccaaat ttggtaactt tttataaagc   900
gaatgtgaat ttataaatat tagatatgga ttttgcttat atcgaatggg tatggatgaa   960
aagaatatta ccatccccat accagaaact caaataacta ttttatgagt gaaatgcata  1020
ggtacttgtg cggatgtgtc atgtaggtta ctaaactctt aaaatgcatt ttttacatcc  1080
caaactctca aaataggc tccaactcac tccatgcgct gatatgacat gccatggtgg  1140
cgccttcatg tgagtgggac ctacgtgtta gtcactagaa aaaaaataaa attaatacac  1200
atttttctc ctctctacat taatactatt ttttattt ttttatcttt tctcctctct   1260
tcctaagagg ggaaagacg ttttatttt tttctatgtg gctaacatgt gggttacatt   1320
gaaatacat tttaagaatt tagggatcta gatgacacac ccgcataagt tgtgagtgtg  1380
tacttcactc ataatctatc tttaccatat cctaccacaa tagtctaagt atgtataata  1440
gtccgagtat gagtaatgga tacctagtag caagctagct taaacaaatc taaatttta  1500
```

```
atatacccaa tgtcatgata attgacttat gacaatgtga ttatttcatc aagtctttaa   1560
atcattaatt ctagttgaag gtttatgttt tcttatgcta aagggttatg tttatataag   1620
aatattaaag agcaaattgc aatagatcaa cacaacaaat ttgaatgttt ccagatgtgt   1680
aaaatatcca aattaattgt tttaaaatag ttttaagaag gatctgatat gcaagtttga   1740
tagttagtaa actgcaaaag ggcttattac atggaaaatt ccttattgaa tatgtttcat   1800
tgactggttt attttacatg acaacaaagt tactagtatg tcaataaaaa aatacaaggt   1860
tacttgtcaa ttgtattgtg ccaagtaaag atgacaacaa acatacaaat ttatttgttc   1920 tttttatagaa acacctaact tatcaaggat agttggccac gcaaaaatga caacatactt   1980
tacaattgta tcatcataaa gatcttatca agtataagaa ctttatggtg acataaaaaa   2040
taatcacaag ggcaagacac atactaaaag tatggacaga aatttcttaa caaactccat   2100
ttgttttgta tccaaaagca taagaaatga gtcatggctg agtcatgata tgtagttcaa   2160
tcttgcaaaa ttgcctttttt gttaagtatt gttttaacac tacaagtcac atattgtcta   2220
tacttgcaac aaacactatt accgtgtatc ccaagtggcc ttttcattgc tatataaact   2280
agcttgatcg gtctttcaac                                               2300
```

<210> SEQ ID NO 13  
<211> LENGTH: 974  
<212> TYPE: DNA  
<213> ORGANISM: Zea mays  
<220> FEATURE:  
<221> NAME/KEY: ZmRbcS_promoter2  
<222> LOCATION: (1)..(974)

<400> SEQUENCE: 13

```
gagctcccctt taatctggcg ctagatctgc atccgcggct tgcaaagata aatggcacat     60
ttagtgtgtt attttgcaat acctttcata gtagatatcc ttaaatgcag ttttaggcat    120
gtttgggtaa ttaaataaca ttttaggag gagtttagga tttacctttc tttcgtgatg    180
actgatgaca gacgtgggga attcaaatgc aactctagcg aaagttcata tattttcat    240 aaatagctga ggctgggta attatttttt ttgtagaaaa atagaatagg tggaatggtt    300
ggggaaggcg taggcgctcg tggacgacgc ccgataaaag acaagaggcg gaattgccat    360
gaattcgagg tagctaagta aggcgcatat atatgccaaa aaattctact gtcactttcc    420
aatttcaatg cgctgccaaa caagccatcc tggaaactga cttgaattca gcccaattct    480
gtagatccaa acagggccgg cgtcagtgcc tcaggtgaga gagcagcaga cgatgcaaag    540
agccaaaact gcaagcagac gcagccgaag ccgaagccga agcccaagcc caaaactgtt    600
ttgtctttgc ccagaaccgc gacgagccta aactgcgctt cctcctatct acaagtccct    660
ggcacatcac gcatagtcca accatggcgc gcaggcgata aggcgcgcca cggggacgcg    720
acatgtggtg gcggacgcga tcaggatagg gccaggctgg ccgggcgcgg ccacgggaga    780
acggtggcca ctcgtcccac atccgcttcg tcctgtcctg tactgcgtcc tgccccaac     840 gagagccgga gccggccatc ccgtcgcaca ctctccccct ctatatatgc cgtcggtgtg    900
ggggagccta ctacaggacg acccaagcaa gcaagcaagc agcgagtaca tacatactag    960
gcagccaggc agcc                                                       974
```

<210> SEQ ID NO 14  
<211> LENGTH: 1692  
<212> TYPE: DNA  
<213> ORGANISM: Synechococcus elongatus  
<220> FEATURE:

<220> FEATURE:
<221> NAME/KEY: RbcS-ictB
<222> LOCATION: (1)..(1692)
<220> FEATURE:
<221> NAME/KEY: RbcS_signal_peptide
<222> LOCATION: (1)..(288)
<220> FEATURE:
<221> NAME/KEY: ictB
<222> LOCATION: (289)..(1692)

<400> SEQUENCE: 14

```
atgccgtcgg tgtgggggag cctactgttt aaacatgagc agctgatggc ttctatgatt      60
tcttcttctg ctgtgacaac agtgtctagg gcttctaggg ccagtctgc tgctgtggct      120
cctttcggcg gcctcaagtc tatgacaggc ttccctgtga agaaggtgaa tacagatatt      180
acatctatta catctaatgg cggcaggtg aagtgcatgc aggtgtggcc tcctattggc      240
aagaagaagt tcgagacact ctcttacctc cctcctctca caaggatat acagtgtgg      300
cagacactca cattcgctca ttaccagcct cagcagtggg gccattcttc tttcctccat      360
aggctcttcg gctctctcag ggcttggagg gcttcttctc agctcctcgt gtggtctgag      420
gctctcggcg gcttcctcct cgctgtggtg tacggctctg ctcctttcgt gccttcttct      480
gctctcggcc tcggcctcgc tgctattgct gcttactggg ctctcctctc tctcacagat      540
attgatctca ggcaggctac acctattcat ggctcgtgc tcctctactg ggcgtggat      600
gctctcgcta caggcctctc tcctgtgagg gctgctgctc tcgtgggcct cgctaagctc      660
acactctacc tctcgtgtt cgctctcgct gctagggtgc tcaggaatcc taggctcagg      720
tctctcctct tctctgtggt ggtgattaca tctctcttcg tgtctgtgta cggcctcaat      780
cagtggattt acggcgtgga ggagctcgct acatgggtgg ataggaattc tgtggctgat      840
ttcacatcta gggtgtactc ttacctcggc aatcctaatc tcctcgctgc ttacctcgtg      900
cctacaacag ctttctctgc tgctgctatt ggcgtgtgga ggggctggct ccctaagctc      960
ctcgctattg ctgctacagg cgcttcttct ctctgcctca ttctcacata tctaggggc     1020
ggctggctcg gcttcgtggc tatgattttc gtgtgggctc tcctcggcct ctactggttc     1080
cagcctaggc tccctgctcc ttggaggagg tggctcttcc ctgtggtgct cggcggcctc     1140
gtggctgtgc tcctcgtggc tgtgctcggc ctcgagcctc tcagggtgag ggtgctctct     1200
attttcgtgg gcagggagga ttcttctaat aatttcagga ttaatgtgtg gctcgctgtg     1260
ctccagatga ttcaggatag gccttggctc ggcattggcc ctggcaatac agcttttcaat     1320
ctcgtgtacc ctctctacca gcaggctagg ttcacagctc tctctgctta ctctgtgcct     1380
ctcgaggtgg ctgtggaggg cggcctcctc ggcctcacag ctttcgcttg gctcctcctc     1440
gtgacagctg tgacagctgt gcgccaggtg tctaggctca ggagggatag gaatcctcag     1500
gctttctggc tcatggcttc tctcgctggc ctcgctggca tgctcggcca tggcctcttc     1560
gatacagtgc tctacaggcc tgaggcttct acactctggt ggctctgcat tggcgctatt     1620
gcttctttct ggcagcctca gccttctaag cagctccctc tgaggctga gcattctgat     1680
gagaagatgt ga                                                         1692
```

<210> SEQ ID NO 15
<211> LENGTH: 563
<212> TYPE: PRT
<213> ORGANISM: Synechococcus elongatus
<220> FEATURE:
<221> NAME/KEY: RbcS-ictB
<222> LOCATION: (1)..(563)
<220> FEATURE:
<221> NAME/KEY: RbcS_sig_peptide
<222> LOCATION: (1)..(96)
<220> FEATURE:
<221> NAME/KEY: ictB
<222> LOCATION: (97)..(563)

<400> SEQUENCE: 15

```
Met Pro Ser Val Trp Gly Ser Leu Leu Phe Lys His Glu Gln Leu Met
1               5                   10                  15

Ala Ser Met Ile Ser Ser Ala Val Thr Thr Val Ser Arg Ala Ser
            20                  25                  30

Arg Gly Gln Ser Ala Ala Val Ala Pro Phe Gly Gly Leu Lys Ser Met
                35                  40                  45

Thr Gly Phe Pro Val Lys Lys Val Asn Thr Asp Ile Thr Ser Ile Thr
    50                  55                  60

Ser Asn Gly Gly Arg Val Lys Cys Met Gln Val Trp Pro Pro Ile Gly
65                  70                  75                  80

Lys Lys Lys Phe Glu Thr Leu Ser Tyr Leu Pro Pro Leu Thr Arg Asp
                85                  90                  95

Met Thr Val Trp Gln Thr Leu Thr Phe Ala His Tyr Gln Pro Gln Gln
            100                 105                 110

Trp Gly His Ser Ser Phe Leu His Arg Leu Phe Gly Ser Leu Arg Ala
        115                 120                 125

Trp Arg Ala Ser Ser Gln Leu Leu Val Trp Ser Glu Ala Leu Gly Gly
130                 135                 140

Phe Leu Leu Ala Val Val Tyr Gly Ser Ala Pro Phe Val Pro Ser Ser
145                 150                 155                 160

Ala Leu Gly Leu Gly Leu Ala Ala Ile Ala Ala Tyr Trp Ala Leu Leu
                165                 170                 175

Ser Leu Thr Asp Ile Asp Leu Arg Gln Ala Thr Pro Ile His Trp Leu
            180                 185                 190

Val Leu Leu Tyr Trp Gly Val Asp Ala Leu Ala Thr Gly Leu Ser Pro
        195                 200                 205

Val Arg Ala Ala Ala Leu Val Gly Leu Ala Lys Leu Thr Leu Tyr Leu
    210                 215                 220

Leu Val Phe Ala Leu Ala Ala Arg Val Leu Arg Asn Pro Arg Leu Arg
225                 230                 235                 240

Ser Leu Leu Phe Ser Val Val Ile Thr Ser Leu Phe Val Ser Val
                245                 250                 255

Tyr Gly Leu Asn Gln Trp Ile Tyr Gly Val Glu Glu Leu Ala Thr Trp
            260                 265                 270

Val Asp Arg Asn Ser Val Ala Asp Phe Thr Ser Arg Val Tyr Ser Tyr
        275                 280                 285

Leu Gly Asn Pro Asn Leu Leu Ala Ala Tyr Leu Val Pro Thr Thr Ala
    290                 295                 300

Phe Ser Ala Ala Ala Ile Gly Val Trp Arg Gly Trp Leu Pro Lys Leu
305                 310                 315                 320

Leu Ala Ile Ala Ala Thr Gly Ala Ser Ser Leu Cys Leu Ile Leu Thr
                325                 330                 335

Tyr Ser Arg Gly Gly Trp Leu Gly Phe Val Ala Met Ile Phe Val Trp
            340                 345                 350

Ala Leu Leu Gly Leu Tyr Trp Phe Gln Pro Arg Leu Pro Ala Pro Trp
        355                 360                 365

Arg Arg Trp Leu Phe Pro Val Val Leu Gly Gly Leu Val Ala Val Leu
    370                 375                 380
```

```
Leu Val Ala Val Leu Gly Leu Glu Pro Leu Arg Val Arg Val Leu Ser
385                 390                 395                 400

Ile Phe Val Gly Arg Glu Asp Ser Ser Asn Asn Phe Arg Ile Asn Val
            405                 410                 415

Trp Leu Ala Val Leu Gln Met Ile Gln Asp Arg Pro Trp Leu Gly Ile
        420                 425                 430

Gly Pro Gly Asn Thr Ala Phe Asn Leu Val Tyr Pro Leu Tyr Gln Gln
            435                 440                 445

Ala Arg Phe Thr Ala Leu Ser Ala Tyr Ser Val Pro Leu Glu Val Ala
    450                 455                 460

Val Glu Gly Gly Leu Leu Gly Leu Thr Ala Phe Ala Trp Leu Leu
465                 470                 475                 480

Val Thr Ala Val Thr Ala Val Arg Gln Val Ser Arg Leu Arg Arg Asp
            485                 490                 495

Arg Asn Pro Gln Ala Phe Trp Leu Met Ala Ser Leu Ala Gly Leu Ala
            500                 505                 510

Gly Met Leu Gly His Gly Leu Phe Asp Thr Val Leu Tyr Arg Pro Glu
            515                 520                 525

Ala Ser Thr Leu Trp Trp Leu Cys Ile Gly Ala Ile Ala Ser Phe Trp
    530                 535                 540

Gln Pro Gln Pro Ser Lys Gln Leu Pro Pro Glu Ala Glu His Ser Asp
545                 550                 555                 560

Glu Lys Met

<210> SEQ ID NO 16
<211> LENGTH: 1551
<212> TYPE: DNA
<213> ORGANISM: Zea mays
<220> FEATURE:
<221> NAME/KEY: ism2
<222> LOCATION: (1)..(1551)

<400> SEQUENCE: 16
atgcagttcg ctctcgctct cgatacaaat tctggccctc atcagattag gtcttgcgag      60
ggcgatggca ttgataggct cgagaagctc tctattggcg gcaggaagca ggagaaggct     120
ctcaggaata ggtgcttcgg cggcagggtg gctgctacaa cacagtgcat tctcacatct     180
gatgcttgcc ctgagacact ccattctcag acacagtctt ctaggaagaa ttacgctgat     240
gctaataggg tgtctgctat tattctcggc ggcggcacag gctctggcct cttccctctc     300
acatctacaa gggctacacc tgctgtgcct gtgggcggct gctacaggct cattgatatt     360
cctatgtcta attgcttcaa ttctggcatt aataagattt tcgtgatgtc tcagttcaat     420
tctacatctc tcaataggca tattcatagg acatacctcg agggcggcat taatttcgct     480
ggcggctctg tgcaggtgct cgctgctaca cagatgcctg aggagcctgc tggctggttc     540
cagggcacag ctgattctat taggaagttc atttgggtgc tcgaggatta ctactctcat     600
aagtctattg ataatattgt gattctctct ggcgatcagc tctacaggat gaattacatg     660
gagctcgtgc agaagcatgt ggaggatgat gctgatatta caatttcttg cgctcctgtg     720
gatgagtcta gggcttctaa gaatggcctc gtgaagattg atcatacagg cagggtgctc     780
cagttcttcg agaagcctaa gggcgctgat ctcaattcta tgagggtgga gacaaatttc     840
ctctcttacg ctattgatga tgctcagaag tacccttacc tcgcttctat gggcatttac     900
gtgttcaaga aggatgctct cctcgatctc tcaagtcta agtacacaca gctccatgat     960
ttcggctctg agattctccc tagggctgtg ctcgatcatt ctgtgcaggc ttgcattttc    1020
```

```
acaggctact gggaggatgt gggcacaatt aagtctttct tcgatgctaa tctcgctctc   1080
acagagcagc cttctaagtt cgatttctac gatcctaaga cacctttctt cacagctcct   1140
aggtgcctcc ctcctacaca gctcgataag tgcaagatga agtacgcttt catttctgat   1200
ggctgcctcc tcagggagtg caatattgag cattctgtga ttggcgtgtg ctctagggtg   1260
tcttctggct gcgagctcaa ggattctgtg atgatgggcg ctgatacata cgagacagag   1320
gaggagaggt ctaagctcct cctcgctggc aagtgcctg tgggcattgg caggaataca   1380
aagattagga attgcattat tgatatgaat gctaggattg caagaatgt ggtgattaca   1440 aattctaagg gcattcagga ggctgatcat cctgaggagg gctactacat taggtctggc   1500
attgtggtga ttctcaagaa tgctacaatt aatgatggct ctgtgatttg a           1551
```

<210> SEQ ID NO 17
<211> LENGTH: 516
<212> TYPE: PRT
<213> ORGANISM: Zea mays
<220> FEATURE:
<221> NAME/KEY: ism2
<222> LOCATION: (1)..(516)

<400> SEQUENCE: 17

```
Met Gln Phe Ala Leu Ala Leu Asp Thr Asn Ser Gly Pro His Gln Ile
  1               5                  10                  15

Arg Ser Cys Glu Gly Asp Gly Ile Asp Arg Leu Glu Lys Leu Ser Ile
             20                  25                  30

Gly Gly Arg Lys Gln Glu Lys Ala Leu Arg Asn Arg Cys Phe Gly Gly
         35                  40                  45

Arg Val Ala Ala Thr Thr Gln Cys Ile Leu Thr Ser Asp Ala Cys Pro
     50                  55                  60

Glu Thr Leu His Ser Gln Thr Gln Ser Ser Arg Lys Asn Tyr Ala Asp
 65                  70                  75                  80

Ala Asn Arg Val Ser Ala Ile Ile Leu Gly Gly Gly Thr Gly Ser Gly
                 85                  90                  95

Leu Phe Pro Leu Thr Ser Thr Arg Ala Thr Pro Ala Val Pro Val Gly
            100                 105                 110

Gly Cys Tyr Arg Leu Ile Asp Ile Pro Met Ser Asn Cys Phe Asn Ser
        115                 120                 125

Gly Ile Asn Lys Ile Phe Val Met Ser Gln Phe Asn Ser Thr Ser Leu
    130                 135                 140

Asn Arg His Ile His Arg Thr Tyr Leu Glu Gly Ile Asn Phe Ala
145                 150                 155                 160

Gly Gly Ser Val Gln Val Leu Ala Ala Thr Gln Met Pro Glu Glu Pro
                165                 170                 175

Ala Gly Trp Phe Gln Gly Thr Ala Asp Ser Ile Arg Lys Phe Ile Trp
            180                 185                 190

Val Leu Glu Asp Tyr Tyr Ser His Lys Ser Ile Asp Asn Ile Val Ile
        195                 200                 205

Leu Ser Gly Asp Gln Leu Tyr Arg Met Asn Tyr Met Glu Leu Val Gln
    210                 215                 220

Lys His Val Glu Asp Ala Asp Ile Thr Ile Ser Cys Ala Pro Val
225                 230                 235                 240

Asp Glu Ser Arg Ala Ser Lys Asn Gly Leu Val Lys Ile Asp His Thr
                245                 250                 255

Gly Arg Val Leu Gln Phe Phe Glu Lys Pro Lys Gly Ala Asp Leu Asn
```

```
                260             265             270
    Ser Met Arg Val Glu Thr Asn Phe Leu Ser Tyr Ala Ile Asp Asp Ala
            275                 280                 285

Gln Lys Tyr Pro Tyr Leu Ala Ser Met Gly Ile Tyr Val Phe Lys Lys
            290                 295                 300

Asp Ala Leu Leu Asp Leu Leu Lys Ser Lys Tyr Thr Gln Leu His Asp
    305                 310                 315                 320

Phe Gly Ser Glu Ile Leu Pro Arg Ala Val Leu Asp His Ser Val Gln
                    325                 330                 335

Ala Cys Ile Phe Thr Gly Tyr Trp Glu Asp Val Gly Thr Ile Lys Ser
                340                 345                 350

Phe Phe Asp Ala Asn Leu Ala Leu Thr Glu Gln Pro Ser Lys Phe Asp
                355                 360                 365

Phe Tyr Asp Pro Lys Thr Pro Phe Phe Thr Ala Pro Arg Cys Leu Pro
                    370                 375                 380

Pro Thr Gln Leu Asp Lys Cys Lys Met Lys Tyr Ala Phe Ile Ser Asp
    385                 390                 395                 400

Gly Cys Leu Leu Arg Glu Cys Asn Ile Glu His Ser Val Ile Gly Val
                    405                 410                 415

Cys Ser Arg Val Ser Ser Gly Cys Glu Leu Lys Asp Ser Val Met Met
                420                 425                 430

Gly Ala Asp Thr Tyr Glu Thr Glu Glu Arg Ser Lys Leu Leu Leu
                435                 440                 445

Ala Gly Lys Val Pro Val Gly Ile Gly Arg Asn Thr Lys Ile Arg Asn
                    450                 455                 460

Cys Ile Ile Asp Met Asn Ala Arg Ile Gly Lys Asn Val Val Ile Thr
    465                 470                 475                 480

Asn Ser Lys Gly Ile Gln Glu Ala Asp His Pro Glu Glu Gly Tyr Tyr
                    485                 490                 495

Ile Arg Ser Gly Ile Val Val Ile Leu Lys Asn Ala Thr Ile Asn Asp
                500                 505                 510

Gly Ser Val Ile
            515

<210> SEQ ID NO 18
<211> LENGTH: 231
<212> TYPE: DNA
<213> ORGANISM: Populus tremuloides
<220> FEATURE:
<221> NAME/KEY: hc1
<222> LOCATION: (1)..(231)

<400> SEQUENCE: 18
atgtctgatt ggggccctgt gttcgtggct gtggtgctct tcattctcct cacacctggc      60
ctcctcattc agattcctgg caggcagagg ctcgtggagt tcggcaattt ccagacatct     120
ggcgtgtcta ttctcgtgca ttctattctc tacttcgctc tcatttgcat tttcctcctc     180
gctgtgggcg tgcatgtgtg ctctctctgc acaccttcta tgctcgattg a              231

<210> SEQ ID NO 19
<211> LENGTH: 76
<212> TYPE: PRT
<213> ORGANISM: Populus tremuloides
<220> FEATURE:
<221> NAME/KEY: hc1
<222> LOCATION: (1)..(76)

<400> SEQUENCE: 19
```

-continued

```
Met Ser Asp Trp Gly Pro Val Phe Val Ala Val Val Leu Phe Ile Leu
1               5                   10                  15

Leu Thr Pro Gly Leu Leu Ile Gln Ile Pro Gly Arg Gln Arg Leu Val
                20                  25                  30

Glu Phe Gly Asn Phe Gln Thr Ser Gly Val Ser Ile Leu Val His Ser
            35                  40                  45

Ile Leu Tyr Phe Ala Leu Ile Cys Ile Phe Leu Leu Ala Val Gly Val
        50                  55                  60

His Val Cys Ser Leu Cys Thr Pro Ser Met Leu Asp
65                  70                  75
```

<210> SEQ ID NO 20
<211> LENGTH: 210
<212> TYPE: DNA
<213> ORGANISM: Sorghum bicolor
<220> FEATURE:
<221> NAME/KEY: hc1
<222> LOCATION: (1)..(210)

<400> SEQUENCE: 20

```
atggctgatt ggggccctgt gctcattggc ctcgtgctct tcattctcct ctctcctggc      60
ctcctcttcc agattcctgg caagggcagg attattgagt tcggcaattt ccagacatct     120
ggcctctcta ttctcattca tgctgtgatt tacttcgctc tcctcgctat tttcctcctc     180
gctgtgggcg tgcatattta cctcggctga                                      210
```

<210> SEQ ID NO 21
<211> LENGTH: 69
<212> TYPE: PRT
<213> ORGANISM: Sorghum bicolor
<220> FEATURE:
<221> NAME/KEY: hc1
<222> LOCATION: (1)..(69)

<400> SEQUENCE: 21

```
Met Ala Asp Trp Gly Pro Val Leu Ile Gly Leu Val Leu Phe Ile Leu
1               5                   10                  15

Leu Ser Pro Gly Leu Leu Phe Gln Ile Pro Gly Lys Gly Arg Ile Ile
                20                  25                  30

Glu Phe Gly Asn Phe Gln Thr Ser Gly Leu Ser Ile Leu Ile His Ala
            35                  40                  45

Val Ile Tyr Phe Ala Leu Leu Ala Ile Phe Leu Leu Ala Val Gly Val
        50                  55                  60

His Ile Tyr Leu Gly
65
```

<210> SEQ ID NO 22
<211> LENGTH: 179
<212> TYPE: PRT
<213> ORGANISM: Setaria italica
<220> FEATURE:
<221> NAME/KEY: ERF_transcription_factor
<222> LOCATION: (1)..(179)

<400> SEQUENCE: 22

```
Met Glu Gln Arg Arg Leu Glu Glu Gln Arg Ala Cys Gly Arg Arg Ala
1               5                   10                  15

Arg Ala Glu Thr Arg His Pro Val Tyr Arg Gly Val Arg Leu Arg Ala
                20                  25                  30

Gly Lys Trp Val Ser Glu Ile Arg Glu Leu Arg Lys Pro Ser Arg Ile
```

```
              35                  40                  45
Trp Leu Gly Thr Tyr Pro Thr Pro Glu Met Ala Ala Ala Tyr Asp
 50                  55                  60

Ala Ala Ala Leu Ala Leu Arg Gly Ala Gly Thr Ala Leu Asn Phe Pro
 65                  70                  75                  80

Asp Ala Ala Arg Ser Arg Pro Ala Pro Ala Ser Ala Ser Ala Glu Asp
                 85                  90                  95

Val Arg Ala Ala Ala Ala Ala Ala Ala Ala Met Asp Gly Arg Arg
                100                 105                 110

His His His His Glu Leu Arg Gly Asp Ser Gly Asp Ala Met Ala Ala
                115                 120                 125

Gly Gly Val Val Asp Glu Asp Asp Leu Phe Glu Met Pro Arg Leu Met
            130                 135                 140

Met Ser Met Ala Glu Gly Leu Met Met Ser Pro Pro Ala Leu Gly Pro
145                 150                 155                 160

Ala Ala Ala Pro Met Met Glu Ala Asp Glu Glu Gly Val Ser Leu Trp
                165                 170                 175

Asp His Ser
```

```
<210> SEQ ID NO 23
<211> LENGTH: 184
<212> TYPE: PRT
<213> ORGANISM: Dichanthelium oligosanthes
<220> FEATURE:
<221> NAME/KEY: ERF_transcription_factor
<222> LOCATION: (1)..(184)

<400> SEQUENCE: 23

Met Glu Arg Arg Arg Gln Glu Glu Gln Arg Thr Gly Pro Cys Gly Arg
 1               5                  10                  15

Arg Ala Arg Ala Glu Thr Arg His Pro Val Tyr Arg Gly Val Arg Leu
                20                  25                  30

Arg Ala Gly Lys Trp Val Ser Glu Ile Arg Glu Leu Arg Lys Pro Ser
            35                  40                  45

Arg Ile Trp Leu Gly Thr Tyr Pro Thr Pro Glu Met Ala Ala Ala Ala
 50                  55                  60

Tyr Asp Ala Ala Ala Leu Ala Leu Arg Gly Ala Gly Thr Ala Leu Asn
 65                  70                  75                  80

Phe Pro Asp Ala Ala Arg Ser His Pro Ala Pro Ala Ser Ala Cys Pro
                85                  90                  95

Glu Asp Val Arg Ala Ala Ala Ala Ala Ala Ala Met Met Asp
                100                 105                 110

Ser Cys Arg Gly Ile Gly Arg His His Glu Leu Arg Gly Asp Asp Gly
            115                 120                 125

Gly Gly Ala Asp Ala Met Ala Gly Val Val Asp Glu Asp Asp Leu Phe
            130                 135                 140

Glu Met Pro Arg Leu Met Met Ser Met Ala Glu Gly Leu Met Met Ser
145                 150                 155                 160

Pro Pro Val Leu Gly Pro Ala Ala Ala Ser Leu Glu Ala Glu Glu Glu
                165                 170                 175

Gly Val Ser Leu Trp Asp His Ser
            180
```

```
<210> SEQ ID NO 24
<211> LENGTH: 199
<212> TYPE: PRT
```

```
<213> ORGANISM: Oryza sativa
<220> FEATURE:
<221> NAME/KEY: ERF_transcription_factor
<222> LOCATION: (1)..(199)

<400> SEQUENCE: 24
```

| Met<br>1 | Asp | Arg | Asp | Glu<br>5 | Ser | Leu | Gly | Thr | Gln<br>10 | Pro | Leu | Thr | Gly | Arg<br>15 | Arg |
|---|---|---|---|---|---|---|---|---|---|---|---|---|---|---|---|
| Val | Arg | Ala | Asp<br>20 | Thr | Arg | His | Pro | Val<br>25 | Tyr | Arg | Gly | Ile | Arg<br>30 | Leu | Arg |
| Ser | Gly | Lys<br>35 | Trp | Val | Ser | Glu | Ile<br>40 | Arg | Glu | Pro | Gly | Lys<br>45 | Ser | Ser | Arg |
| Ile | Trp<br>50 | Leu | Gly | Thr | Tyr | Pro<br>55 | Thr | Pro | Glu | Met | Ala<br>60 | Ala | Ala | Ala | Tyr |
| Asp<br>65 | Ala | Ala | Ala | Leu | Ala<br>70 | Leu | Arg | Gly | Ala | Asp<br>75 | Ala | Ala | Leu | Asn | Phe<br>80 |
| Pro | Gly | Thr | Ala | Thr<br>85 | Ser | Arg | Pro | Ala | Pro<br>90 | Ala | Ser | Gly | Ser | Pro<br>95 | Asp |
| Asp | Ile | Arg | Ala<br>100 | Ala | Ala | Ala | Ala | Ala<br>105 | Ala | Ala | Met | Ile | Gly<br>110 | Ser | Gly |
| His | Arg | Gly<br>115 | Asn | Gln | Arg | Ala | Ala<br>120 | Asp | Ala | Ser | Thr | Ser<br>125 | Arg | Ala | Ala |
| Pro | Ala<br>130 | Pro | Glu | Val | Ala | Val<br>135 | Ala | Ala | Gly | Ala | Gly<br>140 | Asp | Gln | Lys | Arg |
| Val<br>145 | Val | Asp | Glu | Asp | Val<br>150 | Phe | Glu | Met | Pro | Arg<br>155 | Leu | Leu | Val | Ser<br>160 | |
| Met | Ala | Glu | Gly | Leu<br>165 | Met | Met | Asn | Pro | Pro<br>170 | Arg | Leu | Ser | Pro | Ser<br>175 | Thr |
| Asp | Gly | Val | Gly<br>180 | Gly | Val | Ser | Pro<br>185 | Glu | Asp | Asp | Glu | Asp<br>190 | Glu | Asp | Gly |
| Met | Ser | Leu<br>195 | Trp | Asn | His | Ser | | | | | | | | | |

```
<210> SEQ ID NO 25
<211> LENGTH: 200
<212> TYPE: PRT
<213> ORGANISM: Oryza sativa
<220> FEATURE:
<221> NAME/KEY: ERF_transcription_factor
<222> LOCATION: (1)..(200)

<400> SEQUENCE: 25
```

| Met<br>1 | Asp | Arg | Asp | Glu<br>5 | Ser | Leu | Gly | Thr | Gln<br>10 | Pro | Leu | Thr | Gly | Arg<br>15 | Arg |
|---|---|---|---|---|---|---|---|---|---|---|---|---|---|---|---|
| Val | Arg | Ala | Asp<br>20 | Thr | Arg | His | Pro | Val<br>25 | Tyr | Arg | Gly | Ile | Arg<br>30 | Leu | Arg |
| Ser | Gly | Lys<br>35 | Trp | Val | Ser | Glu | Ile<br>40 | Arg | Glu | Pro | Gly | Lys<br>45 | Ser | Ser | Arg |
| Ile | Trp<br>50 | Leu | Gly | Thr | Tyr | Pro<br>55 | Thr | Pro | Glu | Met | Ala<br>60 | Ala | Ala | Ala | Tyr |
| Asp<br>65 | Ala | Ala | Ala | Leu | Ala<br>70 | Leu | Arg | Gly | Ala | Asp<br>75 | Ala | Ala | Leu | Asn | Phe<br>80 |
| Pro | Gly | Thr | Ala | Thr<br>85 | Ser | Arg | Pro | Ala | Pro<br>90 | Ala | Ser | Gly | Ser | Pro<br>95 | Asp |
| Asp | Ile | Arg | Ala<br>100 | Ala | Ala | Ala | Ala | Ala<br>105 | Ala | Ala | Met | Ile | Gly<br>110 | Ser | Gly |
| His | Arg | Gly<br>115 | Asn | Gln | Arg | Ala | Ala<br>120 | Asp | Ala | Ser | Thr | Ser<br>125 | Arg | Ala | Ala |

```
              115                 120                 125
Thr Ala Ala Pro Glu Ala Ala Val Ala Ala Gly Ala Gly Asp Gln Lys
        130                 135                 140

Arg Val Val Asp Glu Asp Asp Val Phe Glu Met Pro Arg Leu Leu Val
145                 150                 155                 160

Ser Met Ala Glu Gly Leu Met Met Ser Pro Pro Arg Leu Ser Pro Ser
                165                 170                 175

Thr Asp Gly Val Gly Gly Val Ser Pro Glu Asp Asp Glu Asp Glu Asp
            180                 185                 190

Gly Met Ser Leu Trp Asn His Ser
        195                 200
```

<210> SEQ ID NO 26
<211> LENGTH: 209
<212> TYPE: PRT
<213> ORGANISM: Zea mays
<220> FEATURE:
<221> NAME/KEY: ERF_transcription_factor
<222> LOCATION: (1)..(209)

<400> SEQUENCE: 26

```
Met Glu Gln Arg Gln Gln Glu Arg Arg Thr Val Pro Thr Thr Thr Thr
1               5                   10                  15

Cys Gly Gly Arg Arg Ala Arg Ala Glu Thr Arg His Pro Val Tyr Arg
            20                  25                  30

Gly Val Arg Leu Arg Ala Gly Lys Trp Val Ser Glu Ile Arg Glu Leu
        35                  40                  45

Arg Lys Pro Ser Arg Ile Trp Leu Gly Thr Tyr Pro Thr Pro Glu Met
50                  55                  60

Ala Ala Ala Ala Tyr Asp Ala Ala Ala Leu Ala Leu Arg Gly Ala Gly
65                  70                  75                  80

Ala Ala Leu Asn Phe Pro Asp Ala Ala Thr Ala Arg Pro Pro Pro Ala
                85                  90                  95

Ser Ala Ser Ala Glu His Val Arg Ala Ala Ala Ala Ala Ala Ala Ala
            100                 105                 110

Ala Ala Ala Val Gly Leu Gly Asp Ser Arg His Phe His Gly Arg Ser
        115                 120                 125

Asp Arg Arg Glu Val Arg Gly His Ser His Ser Ser Gly Ala Asp Glu
130                 135                 140

Tyr Glu Arg Cys His Gly Gly Gly Ala Gly Ser Met Glu Gly Val
145                 150                 155                 160

Val Asp Glu Asp Asp Leu Phe Glu Met Pro Arg Leu Met Leu Ser Met
                165                 170                 175

Ala Glu Gly Leu Met Met Thr Pro Pro Val Leu Gly Pro Ala Pro Ala
            180                 185                 190

Ala Ala Ala Leu Asp Gly Asp Glu Glu Gly Val Ser Leu Trp Asp His
        195                 200                 205

Ser
```

<210> SEQ ID NO 27
<211> LENGTH: 210
<212> TYPE: PRT
<213> ORGANISM: Sorghum bicolor
<220> FEATURE:
<221> NAME/KEY: ERF_transcription_factor
<222> LOCATION: (1)..(210)

<400> SEQUENCE: 27

Met Glu Arg Glu Gln Glu Gln Glu Ala Gly Thr Ala Gln Gln Leu Leu
1               5                   10                  15

Gly Arg Arg Val Arg Ala Asp Thr Arg His Pro Val Tyr Arg Gly Ile
            20                  25                  30

Arg Tyr Arg Gly Gly Lys Trp Val Ser Glu Ile Arg Glu Pro Arg Lys
        35                  40                  45

Ser Asn Arg Ile Trp Leu Gly Thr Tyr Pro Ala Pro Glu Met Ala Ala
50                  55                  60

Ala Ala Tyr Asp Ala Ala Ala Leu Ala Leu Arg Gly Ala Glu Ala Ala
65                  70                  75                  80

Leu Asn Phe Pro Gly Ala Ala Met Ser Arg Pro Ala Pro Ala Ser Cys
                85                  90                  95

Ser Pro Asp Asp Ile Arg Ala Ala Ala Ala Ala Ala Ala Ala Ala Val
            100                 105                 110

Ile Gly Arg Ser His Ser Pro Gln Val Gly Gly Glu Ala Ala Ala Gly
        115                 120                 125

Gly Gly Cys Gly Ala Ser Thr Trp Ser Ser Gly Ala Gly Ala Gln Gly
130                 135                 140

Gln Val Pro Glu His Arg Ala Gly Asp Arg Arg Ile Val Asp Glu Asp
145                 150                 155                 160

Asp Val Phe Gln Val Pro Arg Leu Leu Ala Gly Met Ala Glu Gly Leu
                165                 170                 175

Met Met Ser Pro Pro Arg Leu Val Gly Pro Ala Thr Asp Gly Ala Val
                180                 185                 190

Leu Leu Glu Glu Asp Gly Ser Glu Asp Gly Val Val Ser Leu Trp Asp
            195                 200                 205

His Ser
    210

<210> SEQ ID NO 28
<211> LENGTH: 257
<212> TYPE: PRT
<213> ORGANISM: Sorghum bicolor
<220> FEATURE:
<221> NAME/KEY: ERF_transcription_factor
<222> LOCATION: (1)..(257)

<400> SEQUENCE: 28

Met Ala Val Ala Val Ala Val Val Ser Gly Thr Gly Ile Ala His Leu
1               5                   10                  15

His Phe Leu His Val Leu Leu Pro Glu Ile Pro Gly Phe Ser Gly Glu
            20                  25                  30

Glu Gln Arg Gly Ser Val Pro Val Cys Pro Glu Cys Pro Gly Gln Met
        35                  40                  45

Glu Arg Glu Gln Glu Gln Ala Gly Thr Ala Gln Gln Leu Leu Gly
50                  55                  60

Arg Arg Val Arg Ala Asp Thr Arg His Pro Val Tyr Arg Gly Ile Arg
65                  70                  75                  80

Tyr Arg Gly Gly Lys Trp Val Ser Glu Ile Arg Glu Pro Arg Lys Ser
                85                  90                  95

Asn Arg Ile Trp Leu Gly Thr Tyr Pro Ala Pro Glu Met Ala Ala Ala
            100                 105                 110

Ala Tyr Asp Ala Ala Ala Leu Ala Leu Arg Gly Ala Glu Ala Ala Leu
        115                 120                 125

Asn Phe Pro Gly Ala Ala Met Ser Arg Pro Ala Pro Ala Ser Cys Ser

```
            130                 135                 140
Pro Asp Asp Ile Arg Ala Ala Ala Ala Ala Ala Ala Val Ile
145                 150                 155                 160

Gly Arg Ser His Ser Pro Gln Val Gly Gly Glu Ala Ala Gly Gly
                165                 170                 175

Gly Cys Gly Ala Ser Thr Trp Ser Ser Gly Ala Gly Ala Gln Gly Gln
            180                 185                 190

Val Pro Glu His Arg Ala Gly Asp Arg Arg Ile Val Asp Glu Asp
                195                 200                 205

Val Phe Gln Val Pro Arg Leu Leu Ala Gly Met Ala Glu Gly Leu Met
    210                 215                 220

Met Ser Pro Pro Arg Leu Val Gly Pro Ala Thr Asp Gly Ala Val Leu
225                 230                 235                 240

Leu Glu Glu Asp Gly Ser Glu Asp Gly Val Val Ser Leu Trp Asp His
                    245                 250                 255

Ser

<210> SEQ ID NO 29
<211> LENGTH: 204
<212> TYPE: PRT
<213> ORGANISM: Gossypium hirsutum
<220> FEATURE:
<221> NAME/KEY: ERF_transcription_factor
<222> LOCATION: (1)..(204)

<400> SEQUENCE: 29

Met Val Gln Ser Ser Lys Ser His Glu Ile Ser Ser Ser Ser Gln
1               5                   10                  15

Ser Glu Ala Gly Ser Thr Ser Leu Gly Gln Ser Gln Lys Arg Arg Ala
            20                  25                  30

Gly Arg Lys Lys Phe Lys Glu Thr Arg His Pro Ile Phe Lys Gly Val
        35                  40                  45

Arg Thr Arg Lys Gly Lys Trp Val Ser Glu Val Arg Glu Pro Asn Lys
    50                  55                  60

Lys Ser Arg Ile Trp Leu Gly Thr Phe Ser Tyr Pro Gly Met Ala Ala
65                  70                  75                  80

Lys Ala Tyr Asp Val Ala Ala Leu Ala Leu Arg Gly Asp Ala Ala Ser
                85                  90                  95

Leu Asn Phe Pro Glu Ser Ala Arg Thr Leu Pro Arg Pro Lys Ser Leu
            100                 105                 110

Ser Val Lys Asp Ile Gln Ile Ala Ala Met Glu Ala Ala Glu Thr Phe
        115                 120                 125

Ile Glu Asp Lys Thr Ser Pro Asp Ser Val Ser Ser Ala Val Pro Ala
    130                 135                 140

Phe Pro Glu Asn Met Val Phe Glu Val Glu Asp Glu Asp Glu Val Phe
145                 150                 155                 160

Asn Met Pro Gly Ile Leu Glu Ser Met Ala Glu Gly Leu Met Ile Thr
                165                 170                 175

Pro Pro Ser Met Gln Lys Gly Tyr Tyr Pro Asp Asp Asp Asp Asp
            180                 185                 190

Gly Asn Asp Tyr Val Glu Val Asn Leu Trp Gly Asp
        195                 200

<210> SEQ ID NO 30
<211> LENGTH: 181
<212> TYPE: PRT
```

```
<213> ORGANISM: Zea mays
<220> FEATURE:
<221> NAME/KEY: ERF_transcription_factor
<222> LOCATION: (1)..(181)

<400> SEQUENCE: 30

Met Glu Arg Glu Glu Gln Glu Ala Gly Thr Gly Thr Gly Thr Ala
1               5                   10                  15

Gln Ala Leu Leu Gly Arg Arg Val Arg Ala Asp Thr Arg His Pro Val
            20                  25                  30

Tyr Arg Gly Ile Arg Tyr Arg Gly Gly Lys Trp Val Ser Glu Ile Arg
                35                  40                  45

Glu Pro Arg Lys Ser Ser Arg Ile Trp Leu Gly Thr Tyr Pro Ala Pro
        50                  55                  60

Glu Met Ala Ala Ala Tyr Asp Thr Ala Ala Leu Ala Leu Arg Gly
65                  70                  75                  80

Ala Glu Ala Ala Leu Asn Phe Pro Gly Ala Ala Leu Ser Arg Pro Val
                85                  90                  95

Pro Ala Ser Arg Ser Pro Asp Asp Ile Arg Ala Ala Ala Ser Ala
            100                 105                 110

Ala Arg Ser Gln Ser Pro Gln Val Gly Glu Gly Pro Ala Pro Glu
        115                 120                 125

Arg Arg Ala Gly Asp Arg Ser Ile Val Asp Glu Asp Val Phe Gln
130                 135                 140

Val Pro Arg Leu Leu Ala Gly Met Ala Glu Gly Leu Met Met Ser Pro
145                 150                 155                 160

Pro Arg Leu Ala Gly Ala Ala Leu Leu Glu Glu Asp Val Val Ser
                165                 170                 175

Leu Trp Asp His Ser
            180

<210> SEQ ID NO 31
<211> LENGTH: 202
<212> TYPE: PRT
<213> ORGANISM: Gossypium raimondii
<220> FEATURE:
<221> NAME/KEY: ERF_transcription_factor
<222> LOCATION: (1)..(202)

<400> SEQUENCE: 31

Met Val Gln Ser Ser Lys Ser His Glu Ile Ser Ser Ser Ser Gln
1               5                   10                  15

Ser Glu Ala Gly Ser Thr Ser Leu Gly Gln Ser Gln Lys Arg Lys Ala
            20                  25                  30

Gly Arg Lys Lys Phe Lys Glu Thr Arg His Pro Ile Phe Lys Gly Val
                35                  40                  45

Arg Thr Arg Lys Gly Lys Trp Val Ser Glu Val Arg Glu Pro Asn Lys
        50                  55                  60

Lys Ser Arg Ile Trp Leu Gly Thr Phe Ser Cys Pro Gly Met Ala Ala
65                  70                  75                  80

Lys Ala Tyr Asp Val Ala Ala Leu Ala Leu Arg Gly Asp Ala Ala Ser
                85                  90                  95

Leu Asn Phe Pro Glu Ser Ala His Thr Leu Pro His Pro Lys Ser Leu
            100                 105                 110

Ser Val Lys Asp Ile Gln Ile Ala Ala Met Glu Ala Ala Ala Thr Leu
        115                 120                 125

Ile Asp Asp Lys Thr Leu Pro Asp Ser Val Ser Ser Ala Val Pro Ala
```

```
                130                 135                 140
Phe Pro Glu Asn Met Val Phe Glu Asp Glu Asp Val Phe Asn Met
145                 150                 155                 160

Pro Gly Ile Leu Glu Ser Met Ala Glu Gly Leu Met Ile Thr Pro Pro
                165                 170                 175

Ser Met Gln Lys Gly Tyr Tyr Pro Asp Asp Asp Asp Asp Gly Asn
                180                 185                 190

Asp Tyr Val Glu Val Asn Leu Trp Asp Asp
            195                 200
```

<210> SEQ ID NO 32
<211> LENGTH: 206
<212> TYPE: PRT
<213> ORGANISM: Gossypium arboreum
<220> FEATURE:
<221> NAME/KEY: ERF_transcription_factor
<222> LOCATION: (1)..(206)

<400> SEQUENCE: 32

```
Met Val Gln Ser Ser Lys Ser His Glu Ile Ser Ser Ser Ser Gln
1               5                   10                  15

Ser Glu Ala Gly Ser Thr Ser Leu Gly Gln Ser Gln Lys Arg Arg Ala
                20                  25                  30

Gly Arg Lys Lys Phe Lys Glu Thr Arg His Pro Ile Phe Lys Gly Val
            35                  40                  45

Arg Thr Arg Lys Gly Lys Trp Val Ser Glu Val Arg Glu Pro Asn Lys
    50                  55                  60

Lys Ser Arg Ile Trp Leu Gly Thr Phe Ser Cys Pro Gly Met Ala Ala
65                  70                  75                  80

Lys Ala Tyr Asp Val Ala Ala Leu Ala Leu Arg Gly Asp Ala Ala Ser
                85                  90                  95

Leu Asn Phe Pro Glu Ser Ala Arg Thr Leu Pro Arg Pro Lys Ser Leu
            100                 105                 110

Ser Val Lys Asp Ile Gln Ile Ala Ala Met Glu Ala Ala Glu Thr Phe
    115                 120                 125

Ile Asp Asp Lys Thr Ser Pro Asp Ser Val Ser Ser Ala Val Pro Ala
130                 135                 140

Phe Pro Glu Asn Met Val Phe Glu Asp Glu Asp Glu Val Phe Asn Met
145                 150                 155                 160

Pro Gly Ile Leu Glu Ser Met Ala Glu Gly Leu Met Ile Thr Pro Pro
                165                 170                 175

Ser Met Gln Lys Gly Tyr Tyr Pro Asp Asp Asp Asp Asp Asp Asp
                180                 185                 190

Asp Asp Gly Asn Asp Tyr Val Glu Val Asn Leu Trp Gly Asp
            195                 200                 205
```

<210> SEQ ID NO 33
<211> LENGTH: 197
<212> TYPE: PRT
<213> ORGANISM: Solanum tuberosum
<220> FEATURE:
<221> NAME/KEY: ERF_transcription_factor
<222> LOCATION: (1)..(197)

<400> SEQUENCE: 33

```
Met Asp Gln Leu Asn Lys Asn Ser Ser Leu Ile Leu Ala Ser Asn Asn
1               5                   10                  15

Pro Lys Lys Pro Ala Gly Arg Lys Lys Phe Arg Glu Thr Arg His Pro
```

```
                    20                  25                  30
Val Tyr Arg Gly Val Arg Met Arg Asn Ser Gly Lys Trp Val Cys Glu
            35                  40                  45

Val Arg Glu Pro Asn Lys Lys Ser Arg Ile Trp Leu Gly Thr Phe Pro
        50                  55                  60

Thr Ala Glu Met Ala Ala Arg Ala His Asp Val Ala Ala Leu Ala Leu
65                  70                  75                  80

Arg Gly Arg Ser Ala Cys Leu Asn Phe Ala Asp Ser Ala Trp Arg Leu
                85                  90                  95

Pro Ile Pro Ala Ser Ser Asn Ser Lys Asp Ile Gln Lys Ala Ala Ala
            100                 105                 110

Glu Ala Ala Glu Ile Phe Arg Pro Ser Glu Glu Ser Glu Arg Val Ala
        115                 120                 125

Ser Ser Glu Met His Glu Ser Ile Phe Phe Met Asn Asp Glu Gly Arg
130                 135                 140

Glu Ser Ser Phe Phe Met Asp Glu Glu Ala Leu Phe Asp Met Pro Gly
145                 150                 155                 160

Leu Ile Ala Asn Met Ala Glu Gly Leu Met Leu Pro Pro Pro Gln Cys
                165                 170                 175

Ala Glu Val Glu Asp His Tyr Tyr Met Glu Ala Asp Asp Ala Tyr Met
            180                 185                 190

Pro Leu Trp Asn Tyr
        195

<210> SEQ ID NO 34
<211> LENGTH: 171
<212> TYPE: PRT
<213> ORGANISM: Cicer arietinum
<220> FEATURE:
<221> NAME/KEY: ERF_transcription_factor
<222> LOCATION: (1)..(171)

<400> SEQUENCE: 34

Met Ser Ser Ser Ser Ser Lys Arg His Pro Thr Tyr His Gly Ile
1               5                   10                  15

Arg Ser Arg Gly Gly Lys Trp Val Thr Glu Ile Arg Glu Pro Arg Lys
            20                  25                  30

Thr Asn Arg Ile Trp Leu Gly Thr Phe Ser Thr Pro Glu Met Ala Ala
        35                  40                  45

Ala Ala Tyr Asp Val Ala Thr Leu Ala Leu Lys Gly Gly Glu Ala Ile
    50                  55                  60

Leu Asn Phe Pro Asp Leu Ala Arg Arg Tyr Pro Val Pro Ala Ser Asn
65                  70                  75                  80

Ser Ala Glu Asp Ile Arg Ser Ala Thr Ser Ala Ala Glu Leu Met
            85                  90                  95

Thr Gly Gly Ser Thr Phe Asn Glu Pro Tyr Asn Asn Ala Phe Tyr Asp
        100                 105                 110

Ala Pro His Ser Tyr Asn Tyr Glu Ser Glu Phe Ile Asp Glu Glu Ala
    115                 120                 125

Ile Phe Ser Met Pro Arg Leu Leu Val Asp Met Ala Glu Gly Met Leu
130                 135                 140

Leu Ser Pro Pro Arg Met Asn Leu Pro Pro Ser Asp Tyr Ser Thr Glu
145                 150                 155                 160

Tyr Gln Thr Phe Gly Glu Ser Leu Trp Asn Phe
            165                 170
```

<210> SEQ ID NO 35
<211> LENGTH: 220
<212> TYPE: PRT
<213> ORGANISM: Solanum pennellii
<220> FEATURE:
<221> NAME/KEY: ERF_transcription_factor
<222> LOCATION: (1)..(220)

<400> SEQUENCE: 35

Met Asn Ile Phe Glu Thr Tyr Asn Ser Asp Ser Leu Ile Ser Thr Glu
1               5                   10                  15

Ser Ser Ser Ser Ser Ser Ser Ser Ser Phe Ser Glu Glu Glu Ile
            20                  25                  30

Ile Leu Ala Ser Asn Asn Pro Lys Arg Pro Ala Gly Arg Lys Lys Phe
        35                  40                  45

Arg Glu Thr Arg His Pro Ile Tyr Arg Gly Ile Arg Lys Arg Asn Ser
    50                  55                  60

Gly Lys Trp Val Cys Glu Val Arg Glu Pro Asn Lys Lys Thr Arg Ile
65                  70                  75                  80

Trp Leu Gly Thr Phe Pro Thr Ala Glu Met Ala Ala Arg Ala His Asp
                85                  90                  95

Val Ala Ala Leu Ala Leu Arg Gly Arg Ser Ala Cys Leu Asn Phe Ser
            100                 105                 110

Asp Ser Ala Trp Arg Leu Pro Ile Pro Ala Ser Ser Asn Ser Lys Asp
        115                 120                 125

Ile Gln Lys Ala Ala Ala Glu Ala Ala Glu Ile Phe Arg Pro Leu Lys
    130                 135                 140

Glu Ser Glu Glu Val Ser Arg Glu Ser Asp Asn Ser Thr Ser Pro Glu
145                 150                 155                 160

Thr Ser Glu Asn Val Gln Glu Ser Ser Asp Phe Val Asp Glu Glu Ala
                165                 170                 175

Leu Phe Phe Met Pro Gly Leu Leu Ala Asn Met Ala Glu Gly Leu Met
            180                 185                 190

Leu Pro Pro Pro Gln Cys Ala Glu Met Ala Asp His Tyr Val Glu Thr
        195                 200                 205

Asp Ala Tyr Met Leu Thr Leu Trp Asn Tyr Ser Ile
    210                 215                 220

<210> SEQ ID NO 36
<211> LENGTH: 204
<212> TYPE: PRT
<213> ORGANISM: Trifolium subterraneum
<220> FEATURE:
<221> NAME/KEY: ERF_transcription_factor
<222> LOCATION: (1)..(204)

<400> SEQUENCE: 36

Met Ser Glu Asn Thr Thr Thr Thr Tyr Ala Ser Ser Ser Ser Ser Gly
1               5                   10                  15

Lys Val Leu Ser Gly Arg His Pro Val Tyr Arg Gly Val Arg Arg Arg
            20                  25                  30

Asn Asn Gly Lys Trp Val Ser Glu Ile Arg Glu Pro Lys Lys Pro Asn
        35                  40                  45

Arg Ile Trp Leu Gly Thr Tyr Pro Thr Pro Glu Met Ala Ala Ile Ala
    50                  55                  60

Tyr Asp Val Ala Ala Leu Ala Leu Lys Gly Lys Asn Ala Ile Leu Asn
65                  70                  75                  80

```
Phe Pro Asn Ser Ser Ser Ser Leu Pro Val Pro Glu Ser Ser Ser Ala
                    85                  90                  95

Arg Asp Ile Gln Thr Ala Ala Ala Ser Ala Ala Ala Val Gly Ala
            100                 105                 110

Ala Glu Asp Ala Leu Ala Ser Asn Ile Asn Val Gly Asn Asn Asn His
            115                 120                 125

Ala Ala Met Ser Pro His Glu Phe Leu Ala Ser Ala Asn Glu Asn Asn
        130                 135                 140

Asn Val Asn His Glu Phe Val Asp Glu Asp Leu Ile Phe Asp Met Pro
145                 150                 155                 160

Asn Val Leu Ala Asn Met Ala Glu Gly Met Leu Leu Ser Pro Pro Arg
                165                 170                 175

Phe Asp Phe Ala Ser Asn Glu Tyr Asp Ala Gln Glu Asn Asp Met Cys
                180                 185                 190

Asp Asp Ser Asn Leu Trp Ser Tyr Pro Tyr Phe Pro
            195                 200

<210> SEQ ID NO 37
<211> LENGTH: 199
<212> TYPE: PRT
<213> ORGANISM: Manihot esculenta
<220> FEATURE:
<221> NAME/KEY: ERF_transcription_factor
<222> LOCATION: (1)..(199)

<400> SEQUENCE: 37

Met His Tyr Ser Gln Ser Ser Asn Ser Gly Asn Ser Ala Ala Ala Asn
1               5                   10                  15

Gln Leu Arg Ala Thr Ala Pro Ser Ala Val Ser Gly Arg His Pro Val
            20                  25                  30

Tyr Arg Gly Val Arg Arg Arg Ser Gly Lys Trp Val Ser Glu Ile
        35                  40                  45

Arg Glu Pro Arg Lys Pro Asn Arg Ile Trp Leu Gly Thr Phe Pro Thr
    50                  55                  60

Pro Glu Met Ala Ala Val Ala Tyr Asp Val Ala Ala Leu Ala Leu Lys
65                  70                  75                  80

Gly Arg Asp Ala Glu Leu Asn Phe Pro Asn Ser Ala Ser Ser Leu Pro
                85                  90                  95

Val Pro Val Ser Thr Ser Pro Arg Asp Ile Gln Ala Ala Ala Ala Ser
            100                 105                 110

Ala Ala Ala Ala Val Gly Ala Ser Arg Asp Ala Leu Gly Ile Gly Ser
            115                 120                 125

Tyr Arg Gln Glu Ser Thr Asn Gln Thr Val Val Gln Glu Arg Pro Met
        130                 135                 140

Phe Asn Glu Phe Val Asp Glu Asp Leu Ile Phe Asp Met Pro Asn Val
145                 150                 155                 160

Leu Met Asn Met Ala Glu Gly Met Leu Leu Ser Pro Pro Arg Leu Asp
                165                 170                 175

Ile Ala Gly Asp Glu Tyr Ala Asp Asp Pro Tyr Ser Gly Leu Met Asp
                180                 185                 190

Gln Asn Leu Trp Arg Phe Pro
            195

<210> SEQ ID NO 38
<211> LENGTH: 179
<212> TYPE: PRT
<213> ORGANISM: Elaeis guineensis
```

```
<220> FEATURE:
<221> NAME/KEY: ERF_transcription_factor
<222> LOCATION: (1)..(179)

<400> SEQUENCE: 38

Met Ala Ala Asn Pro Pro Ala Thr Gly Lys His Gln Ser Tyr Arg Gly
1               5                   10                  15

Val Arg Ser Arg Tyr Gly Lys Trp Val Ser Glu Ile Arg Glu Pro Gly
            20                  25                  30

Lys Asp Ser Arg Ile Trp Leu Gly Thr Tyr Pro Thr Pro Glu Met Ala
        35                  40                  45

Ala Met Ala Tyr Asp Val Ala Ala Leu Ala Leu Arg Gly Ser Gly Ala
    50                  55                  60

Val Leu Asn Phe Pro Asp Ala Val Gly Arg His Pro Ala Leu Ala Ser
65                  70                  75                  80

Thr Ser Arg Thr Asp Ile Arg Ala Ala Ala Ser Ala Ala Ala Ala Ala
                85                  90                  95

Met Thr Val Pro Ala Thr Gln Arg Pro Gly Thr Ser Ser Asp Ala Thr
            100                 105                 110

Asp Arg Gln Cys Trp Phe Asp Gly Thr Ser Ser Gly Gly Asp Gly Ala
        115                 120                 125

Lys Phe Leu Asp Glu Asp Glu Ile Phe Asp Met Pro Gln Leu Leu Arg
    130                 135                 140

Ser Met Ala Glu Gly Met Leu Met Thr Pro Pro Ser Trp Leu Ser Pro
145                 150                 155                 160

Ser Gln Ser Glu Asp Thr Pro Glu Thr Ser Gly Glu Glu Ser Leu Trp
                165                 170                 175

Ser Tyr Pro

<210> SEQ ID NO 39
<211> LENGTH: 187
<212> TYPE: PRT
<213> ORGANISM: Brassica napus
<220> FEATURE:
<221> NAME/KEY: ERF_transcription_factor
<222> LOCATION: (1)..(187)

<400> SEQUENCE: 39

Met Pro Gly Thr Ser Lys Glu Asn Gly Gly Arg His Pro Leu Tyr Lys
1               5                   10                  15

Gly Val Arg Gln Arg Lys Asn Ser Asp Lys Trp Val Ser Glu Ile Arg
            20                  25                  30

Glu Pro Arg Thr Pro Asn Arg Ile Trp Leu Gly Thr Phe Ser Thr Pro
        35                  40                  45

Glu Met Ala Ala Ile Ala Tyr Asp Val Ala Ala Leu Ala Leu Lys Gly
    50                  55                  60

Thr Gln Thr Glu Leu Asn Phe Pro Asn Ser Ala Ser Ser Phe Pro Val
65                  70                  75                  80

Pro Ala Ser Met Ser Pro Gly Asp Ile Gln Ala Ala Ala Ala Ser Ala
                85                  90                  95

Ala Ala Ala Phe Gly Ala Ala Arg Asp Ala Ile Val Met Thr Asn Asn
            100                 105                 110

Asn Ser Ala Thr Ser Ser Val Glu Arg Ser Asn Val Met Met Met Asn
        115                 120                 125

Gly Ser Tyr Glu Asp Thr Tyr Gly Phe Met Asp Glu Asp Phe Ile Phe
    130                 135                 140
```

Asp Met Pro Asn Met Leu Met Asn Met Ala Glu Gly Met Leu Leu Ser
145                 150                 155                 160

Pro Pro Arg Gln Pro Thr Phe Asp Ala Ala Ser Asp Gly Tyr Gly Tyr
                165                 170                 175

Thr Gly Ala Asp Asp Tyr Leu Trp Ser Phe Pro
            180                 185

<210> SEQ ID NO 40
<211> LENGTH: 186
<212> TYPE: PRT
<213> ORGANISM: Ricinus communis
<220> FEATURE:
<221> NAME/KEY: ERF_transcription_factor
<222> LOCATION: (1)..(186)

<400> SEQUENCE: 40

Met His Cys Ser Gln Pro Ser Asn Thr Ser Thr Asn Ser Ser Val Ser
1               5                   10                  15

Gly Arg His Pro Val Tyr Arg Gly Val Arg Arg Arg Ser Ser Gly Lys
                20                  25                  30

Trp Val Ser Glu Ile Arg Glu Pro Lys Lys Pro Asn Arg Ile Trp Leu
            35                  40                  45

Gly Thr Phe Pro Thr Pro Glu Met Ala Ala Val Ala Tyr Asp Val Ala
        50                  55                  60

Ala Leu Ala Leu Lys Gly Arg Asp Ala Glu Leu Asn Phe Pro Asn Ser
65                  70                  75                  80

Ala Ala Ser Leu Pro Val Pro Ala Ser Ala Ser Pro Arg Asp Ile Gln
                85                  90                  95

Ala Ala Ala Ala Ser Ala Ala Ala Ile Gly Ala Ala Arg Asp Ala
                100                 105                 110

Leu Gly Ile Gly Ser Ser Ser His Gln Thr Val Ile Met Gln Glu Ser
            115                 120                 125

Asn Tyr Arg Pro Met Val His Glu Phe Val Asp Glu Asp Leu Ile Phe
        130                 135                 140

Asp Met Pro Asn Leu Leu Val Asn Met Ala Glu Gly Met Leu Leu Ser
145                 150                 155                 160

Pro Pro Arg Leu Asp Ile Ala Pro Asp Ala Ala Phe Asp Asp Glu Asn
                165                 170                 175

Pro Gly Asp Gln Asn Leu Trp Lys Phe Thr
            180                 185

<210> SEQ ID NO 41
<211> LENGTH: 190
<212> TYPE: PRT
<213> ORGANISM: Eutrema salsugineum
<220> FEATURE:
<221> NAME/KEY: ERF_transcription_factor
<222> LOCATION: (1)..(190)

<400> SEQUENCE: 41

Met Pro Gly Thr Ser Lys Asp Asn Gly Gly Arg His Pro Leu Tyr Arg
1               5                   10                  15

Gly Val Arg Gln Arg Arg Asn Ser Asn Lys Trp Val Ser Glu Ile Arg
                20                  25                  30

Glu Pro Arg Lys Pro Asn Arg Ile Trp Leu Gly Thr Phe Ser Thr Pro
            35                  40                  45

Glu Met Ala Ala Ile Ala Tyr Asp Val Ala Ala Leu Ala Leu Lys Gly
        50                  55                  60

Thr Gln Thr Glu Leu Asn Phe Pro Asn Ser Ala Ser Ser Leu Pro Val
65                  70                  75                  80

Pro Ala Ser Met Ser Pro Gly Asp Ile Gln Ala Ala Ala Ser Ala
            85                  90                  95

Ala Ala Ala Phe Gly Ala Ala Arg Asp Ala Ile Val Leu Ala Asn Asn
                100                 105                 110

Asn Ser Glu Thr Ser Gly Ala Ser His Ser Asn Met Met Met Met Asn
            115                 120                 125

Gly Ser Tyr Asn Glu Asn Thr Asn Met Asn Gly Phe Ile Asp Glu Asp
130                 135                 140

Leu Ile Phe Asp Met Pro Asn Val Leu Met Asn Met Ala Glu Gly Met
145                 150                 155                 160

Leu Leu Ser Pro Pro Arg Ala Pro Ala Phe Asp Ala Ala Ser Asp Ala
                165                 170                 175

Asp Cys Tyr Thr Gly Ala Asp Asp Tyr Leu Trp Asn Phe Pro
            180                 185                 190

<210> SEQ ID NO 42
<211> LENGTH: 193
<212> TYPE: PRT
<213> ORGANISM: Vigna radiata
<220> FEATURE:
<221> NAME/KEY: ERF_transcription_factor
<222> LOCATION: (1)..(193)

<400> SEQUENCE: 42

Met Arg Ser Thr Asn Ser Thr Thr Cys Ala Ala Ser Ser Thr Gly Ala
1               5                   10                  15

Ser Asn Gly Asn Thr Gly Arg His Pro Val Tyr Arg Gly Val Arg Arg
            20                  25                  30

Arg Ser Ser Gly Lys Trp Val Ser Glu Ile Arg Glu Pro Arg Lys Pro
            35                  40                  45

Asn Arg Ile Trp Leu Gly Thr Phe Ala Thr Pro Glu Met Ala Ala Ile
        50                  55                  60

Ala Tyr Asp Val Ala Ala Leu Ala Leu Lys Gly Lys Asp Ala Glu Leu
65                  70                  75                  80

Asn Phe Pro Asp Ser Ala Ser Ser Leu Pro Val Pro Ala Ser Ser Ala
                85                  90                  95

Ala Arg Asp Ile Gln Met Ala Ala Ser Ala Ala Ala Val Gly
            100                 105                 110

Ala Ala Asn Asp Ala Leu Ser Glu Gly Ser Arg Gly Gly Asn Val Ser
            115                 120                 125

Val Ser Met Ala Gln Glu Glu Phe Ser Gly Gly Ser Leu Asn His Phe
130                 135                 140

Val Asp Glu Asp Leu Ile Phe Asp Met Pro Asn Ile Leu Val Asn Met
145                 150                 155                 160

Ala Glu Gly Met Leu Leu Ser Pro Pro Arg Phe Asp Asn Phe Ser Ala
                165                 170                 175

Thr Asp Tyr Asp Tyr Met Asp Glu Asn Pro Asn Leu Trp Gly Phe Pro
            180                 185                 190

Tyr

<210> SEQ ID NO 43
<211> LENGTH: 184
<212> TYPE: PRT
<213> ORGANISM: Brassica oleracea
<220> FEATURE:

<221> NAME/KEY: ERF_transcription_factor
<222> LOCATION: (1)..(184)

<400> SEQUENCE: 43

Met Asn Ile Pro Gly Thr Ser Lys Glu Asn Ser Gly Arg His Pro Leu
1               5                   10                  15

Tyr Lys Gly Val Arg Gln Arg Lys Asn Ser Asp Lys Trp Val Ser Glu
            20                  25                  30

Ile Arg Glu Pro Arg Lys Pro Asn Arg Ile Trp Leu Gly Thr Phe Ser
        35                  40                  45

Thr Pro Glu Met Ala Ala Ile Ala Tyr Asp Val Ala Ala Leu Ala Leu
    50                  55                  60

Lys Gly Thr Gln Thr Gly Leu Asn Phe Pro Asn Ser Ala Ser Ser Leu
65                  70                  75                  80

Pro Val Pro Ala Ser Met Ser Pro Gly Asp Ile Gln Ala Ala Ala Ala
                85                  90                  95

Ser Ala Ala Ala Phe Gly Ala Ala Arg Asp Ala Ile Val Val Ala
            100                 105                 110

Asn Asn Ser Ser Val Glu Arg Ser Asn Val Met Met Asn Gly Ser Tyr
        115                 120                 125

Glu Asn Thr Asn Gly Phe Met Asp Glu Asp Leu Ile Phe Asp Met Pro
    130                 135                 140

Asn Val Leu Met Asn Met Ala Glu Gly Met Leu Leu Ser Pro Pro Cys
145                 150                 155                 160

Gln Phe Thr Phe Asp Ala Ala Ser Glu Ala Asp Asp Tyr Ala Gly Glu
                165                 170                 175

Asp Asp Tyr Leu Trp Asn Phe Thr
            180

<210> SEQ ID NO 44
<211> LENGTH: 237
<212> TYPE: PRT
<213> ORGANISM: Vitis vinifera
<220> FEATURE:
<221> NAME/KEY: ERF_transcription_factor
<222> LOCATION: (1)..(237)

<400> SEQUENCE: 44

Met Glu Glu Pro Arg Ala Asn Val Arg Pro Ser Asp Gln Pro Pro Pro
1               5                   10                  15

Thr Pro Lys Ile Glu Val Pro Asp Ser Ser Leu Ser Ile Val Pro Pro
            20                  25                  30

Gln Asp Leu Ser Ser Pro Pro Ser His Ser Ser Ser Thr Pro Thr Ser
        35                  40                  45

Ala His Pro Ser Pro Lys Asn Leu Pro Ser Pro Thr Pro Phe Ser Gly
    50                  55                  60

Gln Thr Ala Gly Arg His Pro Phe Tyr Arg Gly Ile Arg Cys Arg Gly
65                  70                  75                  80

Asn Lys Trp Val Ser Glu Ile Arg Glu Pro Arg Lys Thr Thr Arg Ile
                85                  90                  95

Trp Leu Gly Thr Tyr Pro Thr Pro Glu Met Ala Ala Thr Ala Tyr Asp
            100                 105                 110

Val Ala Ala Leu Ala Leu Lys Gly Thr Asp Ala Thr Leu Asn Phe Pro
        115                 120                 125

Asn Ser Val Leu Ser Tyr Pro Ile Pro Lys Ser Thr Ser Ala Ser Asp
    130                 135                 140

```
Ile Arg Ala Ala Ala Arg Ala Glu Ala Gln Gln Ala Lys Pro
145                 150                 155                 160

Glu Ser Ser Glu Ser Pro Asn Thr Thr Gln Pro Lys Lys Glu Glu Thr
                165                 170                 175

Thr Glu Ser Ser Ser Leu Ala Ala Gly Glu Asp Gln Phe Ile Asp Glu
            180                 185                 190

Glu Glu Leu Leu Asn Met Pro Asn Leu Leu Val Asp Met Ala Glu Gly
        195                 200                 205

Met Leu Val Ser Pro Pro Arg Leu Lys Ser Gln Pro Ser Asp Asp Ser
    210                 215                 220

Pro Glu Asn Ser Asp Ser Asp Ser Leu Trp Ser Tyr Thr
225                 230                 235

<210> SEQ ID NO 45
<211> LENGTH: 220
<212> TYPE: PRT
<213> ORGANISM: Eucalyptus gunnii
<220> FEATURE:
<221> NAME/KEY: ERF_transcription_factor
<222> LOCATION: (1)..(220)

<400> SEQUENCE: 45

Met Asn Pro Phe Ser Ser His Ser His Pro Asn Ser Cys Arg Phe Asn
1               5                   10                  15

Phe Ala Glu Pro Pro Ser Asp Ser Arg Ser Ala Thr Ala Leu Gly Asn
            20                  25                  30

Phe Ser His Lys Glu Val Leu Leu Ala Ser His His Pro Lys Lys Arg
        35                  40                  45

Ala Gly Arg Lys Lys Phe Arg Glu Thr Arg His Pro Val Tyr Arg Gly
    50                  55                  60

Val Arg Leu Arg Asp Ser Gly Lys Trp Val Cys Glu Val Arg Glu Pro
65                  70                  75                  80

Ile Lys Lys Ser Arg Ile Trp Leu Gly Thr Phe Pro Thr Val Glu Met
                85                  90                  95

Ala Ala Arg Ala His Asp Val Ala Ala Leu Ala Leu Arg Gly Arg Ser
            100                 105                 110

Ala Cys Leu Asn Phe Ala Asp Ser Ala Trp Arg Leu Pro Val Pro Ala
        115                 120                 125

Ser Ala Asp Thr Lys Glu Ile Gln Lys Ala Ala Arg Ala Ala Glu
    130                 135                 140

Ala Phe Gln Ser Val Glu Ser Glu Asp Val Met Ser Gly Asp Glu Lys
145                 150                 155                 160

Lys Leu Arg Ser Glu Glu Gly Val Phe Tyr Asp Glu Asp Ile Phe
                165                 170                 175

Gly Met Pro Gly Leu Leu Ala Asp Met Ala Glu Gly Met Leu Leu Ser
            180                 185                 190

Pro Pro Lys Trp Gly Gly Asp Ile Tyr Gly Gly Glu Asp Glu Gly Asn
        195                 200                 205

Leu Gly Ala His Thr Ser Leu Trp Ser Tyr Ser Ile
    210                 215                 220

<210> SEQ ID NO 46
<211> LENGTH: 187
<212> TYPE: PRT
<213> ORGANISM: Brassica rapa
<220> FEATURE:
<221> NAME/KEY: ERF_transcription_factor
<222> LOCATION: (1)..(187)
```

<400> SEQUENCE: 46

| Met | Pro | Gly | Thr | Ser | Lys | Glu | Asn | Gly | Gly | Arg | His | Pro | Leu | Tyr | Lys |
|---|---|---|---|---|---|---|---|---|---|---|---|---|---|---|---|
| 1 | | | | 5 | | | | | 10 | | | | | 15 | |

Gly Val Arg Gln Arg Lys Asn Ser Asp Lys Trp Val Ser Glu Ile Arg
            20              25              30

Glu Pro Arg Thr Pro Asn Arg Ile Trp Leu Gly Thr Phe Ser Thr Pro
            35              40              45

Glu Met Ala Ala Ile Ala Tyr Asp Val Ala Ala Leu Ala Leu Lys Gly
50                55              60

Thr Gln Thr Glu Leu Asn Phe Pro Asn Ser Ala Ser Ser Phe Pro Val
65              70              75              80

Pro Ala Thr Met Ser Pro Arg Asp Ile Gln Ala Ala Ala Ser Ala
            85              90              95

Ala Ala Ala Phe Gly Ala Ala Arg Asp Ala Ile Val Met Thr Asn Asn
            100           105           110

Asn Ser Ala Thr Ser Ser Val Glu Arg Ser Asn Val Met Met Met Asn
         115            120              125

Gly Ser Tyr Glu Asp Thr Tyr Gly Phe Met Asp Glu Asp Phe Ile Phe
    130              135            140

Asp Met Pro Asn Met Leu Met Asn Met Ala Glu Gly Met Leu Leu Ser
145              150           155           160

Pro Pro Arg Gln Pro Thr Phe Asp Ala Ala Ser Asp Gly Tyr Gly Tyr
            165         170             175

Thr Gly Ala Asp Asp Tyr Leu Trp Ser Phe Pro
           180            185

<210> SEQ ID NO 47
<211> LENGTH: 293
<212> TYPE: PRT
<213> ORGANISM: Ricinus communis
<220> FEATURE:
<221> NAME/KEY: ERF_transcription_factor
<222> LOCATION: (1)..(293)

<400> SEQUENCE: 47

Met Ala Ser Glu Val Glu Ser Leu Lys Val Ser Lys Leu Lys Arg Tyr
1               5              10              15

Pro Arg Tyr Arg Ile Leu Gly Pro Phe Met Ser Leu Ser Lys Ser Asn
            20              25              30

Pro Asp Val Gln Gln Arg Ala Val Leu His Pro Lys Ser Leu Lys Asp
            35              40              45

Arg Gln Cys Ser Ser Ser Thr Thr Gly Leu His Phe His Asp Leu Leu
    50              55              60

Leu Leu Ile Ser Asp Ser Ser Val Phe Asp Leu His Ile Asn Gly Phe
65              70              75              80

Ser His Leu Ser Ala Ser Leu Gln Thr His His Leu Pro Ala Ile Ser
            85              90              95

Leu Asn Ser Leu Ser Tyr His Tyr Gln Asn Thr Met His Cys Ser Gln
            100           105           110

Pro Ser Asn Thr Ser Thr Asn Ser Ser Val Ser Gly Arg His Pro Val
         115            120              125

Tyr Arg Gly Val Arg Arg Ser Ser Gly Lys Trp Val Ser Glu Ile
    130              135            140

Arg Glu Pro Lys Lys Pro Asn Arg Ile Trp Leu Gly Thr Phe Pro Thr
145              150           155           160

```
Pro Glu Met Ala Ala Val Ala Tyr Asp Val Ala Ala Leu Ala Leu Lys
            165                 170                 175

Gly Arg Asp Ala Glu Leu Asn Phe Pro Asn Ser Ala Ala Ser Leu Pro
        180                 185                 190

Val Pro Ala Ser Ala Ser Pro Arg Asp Ile Gln Ala Ala Ala Ala Ser
    195                 200                 205

Ala Ala Ala Ala Ile Gly Ala Ala Arg Asp Ala Leu Gly Ile Gly Ser
210                 215                 220

Ser Ser His Gln Thr Val Ile Met Gln Glu Ser Asn Tyr Arg Pro Met
225                 230                 235                 240

Val His Glu Phe Val Asp Glu Asp Leu Ile Phe Asp Met Pro Asn Leu
            245                 250                 255

Leu Val Asn Met Ala Glu Gly Met Leu Leu Ser Pro Pro Arg Leu Asp
            260                 265                 270

Ile Ala Pro Asp Ala Ala Phe Asp Asp Glu Asn Pro Gly Asp Gln Asn
            275                 280                 285

Leu Trp Lys Phe Thr
            290

<210> SEQ ID NO 48
<211> LENGTH: 224
<212> TYPE: PRT
<213> ORGANISM: Eucalyptus grandis
<220> FEATURE:
<221> NAME/KEY: ERF_transcription_factor
<222> LOCATION: (1)..(224)

<400> SEQUENCE: 48

Met Asn Ser Ser Ser Tyr Ile Ser His Pro Asn Ser Phe Ser Phe Asp
1               5                   10                  15

Phe Ala Glu Pro Pro Phe Ser Leu Leu Leu Ser His Asp Arg Ser Ala
            20                  25                  30

Ala Pro Gly Asn Phe Ser Gly Glu Glu Val Arg Leu Ala Ser Asp His
        35                  40                  45

Pro Lys Lys Pro Ala Gly Arg Lys Lys Phe Arg Glu Thr Arg His Pro
    50                  55                  60

Val Tyr Arg Gly Val Arg Leu Arg Asp Ser Gly Lys Trp Val Cys Glu
65                  70                  75                  80

Val Arg Glu Pro Arg Lys Lys Ser Arg Ile Trp Leu Gly Thr Phe Pro
            85                  90                  95

Thr Ala Asp Met Ala Ala Arg Ala His Asp Val Ala Ala Leu Ala Leu
            100                 105                 110

Arg Gly Gln Ser Ala Cys Leu Asn Phe Ala Asp Ser Ala Trp Arg Leu
        115                 120                 125

Pro Val Pro Ala Ser Pro Asn Thr Lys Asp Ile Gln Lys Ala Ala Ala
130                 135                 140

Lys Ala Ala Glu Ala Phe Gln Leu Val Glu Ser Glu Asp Val Met Ser
145                 150                 155                 160

Gly Asn Glu Lys Lys Leu His Ser Glu Glu Gly Val Leu Tyr Asp Glu
            165                 170                 175

Glu Asp Ile Phe Gly Met Pro Gly Leu Leu Ala Asn Met Ala Glu Gly
            180                 185                 190

Met Leu Leu Ser Pro Pro Glu Cys Ser Gly Asp Ile Tyr Ala Gly Glu
        195                 200                 205

Asp Asn Gly Asn Leu Asp Ala Tyr Ala Ser Leu Trp Ser Tyr Ser Met
```

<210> SEQ ID NO 49
<211> LENGTH: 199
<212> TYPE: PRT
<213> ORGANISM: Malus domestica
<220> FEATURE:
<221> NAME/KEY: ERF_transcription_factor
<222> LOCATION: (1)..(199)

<400> SEQUENCE: 49

Met His Ala Thr Asn Thr Thr Thr Ser Ser Ser Thr Thr Ser
1               5                   10                  15

Ile Val Pro Gly Arg His Pro Thr Tyr Arg Gly Val Arg Arg Ser
                20                  25                  30

Ser Gly Lys Trp Val Ser Glu Ile Arg Glu Pro Lys Lys Pro Asn Arg
            35                  40                  45

Ile Trp Leu Gly Thr Phe Pro Thr Pro Glu Met Ala Ala Val Ala Tyr
        50                  55                  60

Asp Val Ala Ala Ile Ala Leu Lys Gly Gln Asp Ala Glu Leu Asn Phe
65                  70                  75                  80

Pro Asn Ser Ala Ser Ser Leu Pro Val Pro Ala Ser Thr Ser Ser Arg
                85                  90                  95

Asp Ile Gln Ala Ala Ser Ser Ala Ala Ala Met Gly Val Ala
            100                 105                 110

Ile Asp Arg Cys Ser Tyr Ser Arg Asp Glu Val Gln Gly Gly His His
        115                 120                 125

Asn Val His Gln Ala His Lys Thr Val Asp Glu Asp Arg Phe Val
    130                 135                 140

Leu Asn His Glu Phe Val Asp Glu Asp Leu Ile Phe Asn Met Pro Asn
145                 150                 155                 160

Val Leu Val Asn Met Ala Glu Gly Met Leu Leu Ser Pro Pro Arg Leu
                165                 170                 175

Asp Ile Ala Gly Asp Asp Ala Ile Asp Ala Asp Gln Glu Gln Gly Asp
            180                 185                 190

Gln Asn Leu Trp Lys Xaa Tyr
        195

<210> SEQ ID NO 50
<211> LENGTH: 211
<212> TYPE: PRT
<213> ORGANISM: Genlisea aurea
<220> FEATURE:
<221> NAME/KEY: ERF_transcription_factor
<222> LOCATION: (1)..(211)

<400> SEQUENCE: 50

Met Glu Pro His His Val Ala Lys Asp Lys Thr Asp Ser Pro Arg Val
1               5                   10                  15

Glu Ile Pro Asp Ala Asn Arg Leu Ser Pro Ala Val Ala Ser Pro
                20                  25                  30

Pro Ser Gly Arg His Pro Leu Tyr Arg Gly Ile Arg Thr Arg Ser Gly
            35                  40                  45

Lys Trp Val Ser Glu Ile Arg Glu Pro Arg Lys Thr Thr Arg Ile Trp
        50                  55                  60

Leu Gly Thr Tyr Thr Thr Ala Glu Met Ala Ala Ala Tyr Asp Val
65                  70                  75                  80

Ala Thr Leu Ala Leu Lys Gly Pro Asp Ala Pro Leu Asn Phe Pro His

```
                85                  90                  95
Leu Ala Ser Ser Tyr Pro Val Pro Ala Thr Leu Ser Ala Gly Asp Ile
            100                 105                 110

Arg Ala Ala Ala Ala Ile Ala Thr Ser Gln Gln Pro Lys Asn Pro
        115                 120                 125

Ser Asp Gly Glu Thr Ser Asp Pro Ala Ala Val Pro Leu Thr Asn
    130                 135                 140

Pro Ala Arg Ser Pro Ala Ile Ala Glu Glu Ile Phe Met Asp Glu
145                 150                 155                 160

Glu Asp Ile Phe Glu Met Pro Lys Leu Met Ala Glu Met Ala Glu Gly
                165                 170                 175

Met Leu Leu Ser Pro Pro Arg Ile Asn Leu Pro Ala Asp Glu Asp Glu
            180                 185                 190

Ser Thr Asp Ala Phe Ala Gly Asn Thr Ile Leu Trp Thr Tyr Asn Ser
        195                 200                 205

Asp Cys Lys
    210

<210> SEQ ID NO 51
<211> LENGTH: 178
<212> TYPE: PRT
<213> ORGANISM: Solanum lycopersicum
<220> FEATURE:
<221> NAME/KEY: ERF_transcription_factor
<222> LOCATION: (1)..(178)

<400> SEQUENCE: 51

Met Ala Ala Tyr His Phe Asn Asp Asn Ser Pro Ser Leu Glu Asn Leu
1               5                   10                  15

Ser Pro Thr Gly Gly Gly Ser Ser Thr Arg His Pro Asn Phe Arg Gly
            20                  25                  30

Ile Arg Gln Arg Asn Gly Lys Trp Val Ser Glu Ile Arg Glu Pro Arg
        35                  40                  45

Lys Thr Thr Arg Ile Trp Leu Gly Thr Phe Pro Ile Pro Glu Met Ala
    50                  55                  60

Ala Val Ala Tyr Asp Val Ala Ala Leu Ala Leu Lys Gly Pro Asp Ala
65                  70                  75                  80

Gln Leu Asn Phe Pro Asp Arg Ala Tyr Ser Tyr Pro Val Pro Ala Ser
                85                  90                  95

Leu Ser Ala Ala Asp Ile Arg Thr Ala Ala Ala Asn Ala Ala Ala Ala
            100                 105                 110

Arg Ala Pro Pro Leu Ser Glu Ile Asn Thr Ala Ala Gly Gly Gly Gln
        115                 120                 125

Gly Gln Glu Phe Val Asp Glu Glu Ile Phe Gly Met Pro Lys Leu
    130                 135                 140

Leu Asp Asp Met Ala Glu Ala Met Leu Val Ser Pro Pro Arg Met His
145                 150                 155                 160

Gln Tyr Asp Glu Ser Pro Glu Asn Ser Asp Ala Asp Ser Leu Trp Gly
                165                 170                 175

Tyr Pro

<210> SEQ ID NO 52
<211> LENGTH: 185
<212> TYPE: PRT
<213> ORGANISM: Camelina sativa
<220> FEATURE:
<221> NAME/KEY: ERF_transcription_factor
```

<222> LOCATION: (1)..(185)

<400> SEQUENCE: 52

Met Gln Gly Thr Ser Lys Asp Asn Gly Gly Arg His Pro Met Tyr Arg
1               5                   10                  15

Gly Val Arg Gln Arg Arg Asn Ser Asp Lys Trp Val Ser Glu Ile Arg
            20                  25                  30

Glu Pro Arg Lys Pro Asn Arg Ile Trp Leu Gly Thr Phe Ser Thr Pro
        35                  40                  45

Glu Met Ala Ala Ile Ala Tyr Asp Val Ala Ala Leu Ala Leu Lys Gly
    50                  55                  60

Thr Gln Ala Glu Leu Asn Phe Pro Asn Ser Val Ser Leu Pro Val
65                  70                  75                  80

Pro Ala Ser Met Ser Pro Gly Asp Ile Gln Ala Ala Ala Ser Ala
                85                  90                  95

Ala Ala Ala Phe Gly Ala Ala Arg Asp Ala Ile Val Met Ala Asn Asn
                100                 105                 110

Asn Ser Glu Thr Ser Gly Val Val Ser Met Asn Asp Ser Tyr Glu Asn
            115                 120                 125

Thr Asn Met Asn Glu Phe Met Asp Asp Leu Val Phe Asp Met Pro
130                 135                 140

Asn Val Leu Met Asn Met Ala Glu Gly Met Leu Leu Ser Pro Pro Arg
145                 150                 155                 160

Pro Ser Ala Phe Asp Ala Ala Tyr Tyr Asp Ala Asp Gly Phe Thr Gly
                165                 170                 175

Gly Asp Asp Tyr Leu Trp Asn Phe Pro
            180                 185

<210> SEQ ID NO 53
<211> LENGTH: 188
<212> TYPE: PRT
<213> ORGANISM: Glycine max
<220> FEATURE:
<221> NAME/KEY: ERF_transcription_factor
<222> LOCATION: (1)..(188)

<400> SEQUENCE: 53

Met Arg Ser Ser Asn Gly Ala Ser Ser Arg Ala Ser Asn Ala Asn
1               5                   10                  15

Thr Gly Arg His Pro Val Tyr Arg Gly Val Arg Arg Arg Ser Ser Gly
            20                  25                  30

Lys Trp Val Ser Glu Ile Arg Glu Pro Lys Lys Pro Asn Arg Ile Trp
            35                  40                  45

Leu Gly Thr Phe Ala Thr Pro Glu Met Ala Ala Ile Ala Tyr Asp Val
    50                  55                  60

Ala Ala Leu Ala Leu Lys Gly Lys Asp Ala Glu Leu Asn Phe Pro Asn
65                  70                  75                  80

Ser Ala Ser Ser Leu Pro Val Pro Thr Ser Ser Ala Ala Arg Asp Ile
                85                  90                  95

Gln Met Ala Ala Ala Ser Ala Ala Ala Val Gly Ala Ala Asn Asp
                100                 105                 110

Ala Leu Glu Gly Ser Arg Gly Gly Asn Ala Ser Val Ser Leu Thr Glu
            115                 120                 125

Glu Phe Ser Gly Gly Asn Leu Asn His Phe Val Asp Glu Asp Leu Ile
130                 135                 140

Phe Asp Met Pro Asn Ile Leu Val Asn Met Ala Glu Gly Met Leu Leu

```
                145                 150                 155                 160
            Ser Pro Pro Arg Phe Asp Asn Phe Ala Ala Thr Asp Tyr Glu Tyr Met
                                165                 170                 175

Asp Glu Asp Pro Asn Leu Trp Gly Phe Pro Asn Tyr
                        180                 185
```

<210> SEQ ID NO 54
<211> LENGTH: 1404
<212> TYPE: DNA
<213> ORGANISM: Synechococcus elongatus
<220> FEATURE:
<221> NAME/KEY: ictB
<222> LOCATION: (1)..(1404)

<400> SEQUENCE: 54

```
atgacagtgt ggcagacact cacattcgct cattaccagc ctcagcagtg gggccattct    60
tctttcctcc ataggctctt cggctctctc agggcttgga gggcttcttc tcagctcctc   120
gtgtggtctg aggctctcgg cggcttcctc ctcgctgtgg tgtacggctc tgctcctttc   180
gtgccttctt ctgctctcgg cctcggcctc gctgctattg ctgcttactg gctctcctc   240
tctctcacag atattgatct caggcaggct acacctattc attggctcgt gctcctctac   300
tggggcgtgg atgctctcgc tacaggcctc tctcctgtga gggctgctgc tctcgtgggc   360
ctcgctaagc tcacactcta cctcctcgtg ttcgctctcg ctgctagggt gctcaggaat   420
cctaggctca ggtctctcct cttctctgtg gtggtgatta catctctctt cgtgtctgtg   480
tacggcctca accaatggat ttacggcgtg gaggagctcg ctacatgggt ggataggaat   540
tctgtggctg atttcacatc tagggtgtac tcttacctcg gcaatcctaa tctcctcgct   600
gcttacctcg tgcctacaac agctttctct gctgctgcta ttggcgtgtg gaggggctgg   660
ctccctaagc tcctcgctat gctgctacta ggcgcttctt ctctctgcct cattctcaca   720
tactctaggg gcggctggct cggcttcgtg gctatgattt tcgtgtgggc tctcctcggc   780
ctctactggt tccagcctag gctccctgct ccttggagga ggtggctctt ccctgtggtg   840
ctcggcggcc tcgtggctgt gctcctcgtg gctgtgctcg gctcgagcc tctcagggtg   900
aggtgctct ctatttcgt gggcagggag gattcttcta ataatttcag gattaatgtg   960
tggctcgctg tgctccagat gattcaggat aggccttggc tcggcattgg ccctggcaat  1020
acagctttca atctcgtgta ccctctctac cagcaggcta ggttcacagc tctctctgct  1080
tactctgtgc ctctcgaggt ggctgtggag ggcggcctcc tcggcctcac agctttcgct  1140
tggctcctcc tcgtgacagc tgtgacagct gtgcgccagg tgtctaggct caggagggat  1200
aggaatcctc aggctttctg gctcatggct tctctcgctg gcctcgctgg catgctcggc  1260
catggcctct tcgatacagt gctctacagg cctgaggctt ctacactctg gtggctctgc  1320
attggcgcta ttgcttcttt ctggcagcct cagccttcta gcagctccc tcctgaggct  1380
gagcattctg atgagaagat gtga                                          1404
```

<210> SEQ ID NO 55
<211> LENGTH: 467
<212> TYPE: PRT
<213> ORGANISM: Synechococcus elongatus
<220> FEATURE:
<221> NAME/KEY: ictB
<222> LOCATION: (1)..(467)

<400> SEQUENCE: 55

Met Thr Val Trp Gln Thr Leu Thr Phe Ala His Tyr Gln Pro Gln Gln

```
  1               5                  10                 15
Trp Gly His Ser Ser Phe Leu His Arg Leu Phe Gly Ser Leu Arg Ala
             20                 25                 30
Trp Arg Ala Ser Ser Gln Leu Leu Val Trp Ser Glu Ala Leu Gly Gly
             35                 40                 45
Phe Leu Leu Ala Val Val Tyr Gly Ser Ala Pro Phe Val Pro Ser Ser
             50                 55                 60
Ala Leu Gly Leu Gly Leu Ala Ala Ile Ala Ala Tyr Trp Ala Leu Leu
 65                 70                 75                 80
Ser Leu Thr Asp Ile Asp Leu Arg Gln Ala Thr Pro Ile His Trp Leu
             85                 90                 95
Val Leu Leu Tyr Trp Gly Val Asp Ala Leu Ala Thr Gly Leu Ser Pro
            100                105                110
Val Arg Ala Ala Ala Leu Val Gly Leu Ala Lys Leu Thr Leu Tyr Leu
            115                120                125
Leu Val Phe Ala Leu Ala Ala Arg Val Leu Arg Asn Pro Arg Leu Arg
            130                135                140
Ser Leu Leu Phe Ser Val Val Ile Thr Ser Leu Phe Val Ser Val
145                150                155                160
Tyr Gly Leu Asn Gln Trp Ile Tyr Gly Val Glu Glu Leu Ala Thr Trp
            165                170                175
Val Asp Arg Asn Ser Val Ala Asp Phe Thr Ser Arg Val Tyr Ser Tyr
            180                185                190
Leu Gly Asn Pro Asn Leu Leu Ala Ala Tyr Leu Val Pro Thr Thr Ala
            195                200                205
Phe Ser Ala Ala Ala Ile Gly Val Trp Arg Gly Trp Leu Pro Lys Leu
            210                215                220
Leu Ala Ile Ala Ala Thr Gly Ala Ser Ser Leu Cys Leu Ile Leu Thr
225                230                235                240
Tyr Ser Arg Gly Gly Trp Leu Gly Phe Val Ala Met Ile Phe Val Trp
            245                250                255
Ala Leu Leu Gly Leu Tyr Trp Phe Gln Pro Arg Leu Pro Ala Pro Trp
            260                265                270
Arg Arg Trp Leu Phe Pro Val Val Leu Gly Gly Leu Val Ala Val Leu
            275                280                285
Leu Val Ala Val Leu Gly Leu Glu Pro Leu Arg Val Arg Val Leu Ser
            290                295                300
Ile Phe Val Gly Arg Glu Asp Ser Ser Asn Phe Arg Ile Asn Val
305                310                315                320
Trp Leu Ala Val Leu Gln Met Ile Gln Asp Arg Pro Trp Leu Gly Ile
            325                330                335
Gly Pro Gly Asn Thr Ala Phe Asn Leu Val Tyr Pro Leu Tyr Gln Gln
            340                345                350
Ala Arg Phe Thr Ala Leu Ser Ala Tyr Ser Val Pro Leu Glu Val Ala
            355                360                365
Val Glu Gly Gly Leu Leu Gly Leu Thr Ala Phe Ala Trp Leu Leu Leu
            370                375                380
Val Thr Ala Val Thr Ala Val Arg Gln Val Ser Arg Leu Arg Arg Asp
385                390                395                400
Arg Asn Pro Gln Ala Phe Trp Leu Met Ala Ser Leu Ala Gly Leu Ala
            405                410                415
Gly Met Leu Gly His Gly Leu Phe Asp Thr Val Leu Tyr Arg Pro Glu
            420                425                430
```

Ala Ser Thr Leu Trp Trp Leu Cys Ile Gly Ala Ile Ala Ser Phe Trp
        435                 440                 445

Gln Pro Gln Pro Ser Lys Gln Leu Pro Pro Glu Ala Glu His Ser Asp
    450                 455                 460

Glu Lys Met
465

<210> SEQ ID NO 56
<211> LENGTH: 606
<212> TYPE: DNA
<213> ORGANISM: Brachypodium distachyon
<220> FEATURE:
<221> NAME/KEY: ERF_Transcription_Factor
<222> LOCATION: (1)..(606)

<400> SEQUENCE: 56
atgtctgagc atggcggctc ttctggcaag catcctttct acaggggcat taggtctagg      60
tgcggcaagt gggtgtctga gattagggag cctaggaagg ctaggaggat ttggctcggc     120
acattcccta cacctgagat ggctgctgtg gcttacgatg tggctgctag ggctctcagg     180
ggccctgatg ctgctctcaa tttccctgct attgctgctt ctaggcctgc tcctgcttct     240
acatctgctg atgatattag ggctgctgct gctgctgctg ctgcttctct cgctggcggc     300
ggcggcattg ctcctcctgg cggcgctgct ggctctgctg tgcagcagca gcagcagttc     360
ggcggcggct ctggcacagc tgctggctct gaggaggctg cttctattgg cgctaattac     420
tacaatgtga atcagcagca gcagtacttc ctcgatgagg aggctctctt cgagacacct     480
cagttcctca ggtctatggc tgctggcatg atgatgtctc ctcctaggct ctctcctgat     540
tcttctgatg agtctcctga tccttctgag gctggcgagt ctctctggtc ttacagggat     600
ccttga                                                               606

<210> SEQ ID NO 57
<211> LENGTH: 201
<212> TYPE: PRT
<213> ORGANISM: Brachypodium distachyon
<220> FEATURE:
<221> NAME/KEY: ERF_Transcription_Factor
<222> LOCATION: (1)..(201)

<400> SEQUENCE: 57

Met Ser Glu His Gly Gly Ser Ser Gly Lys His Pro Phe Tyr Arg Gly
1               5                   10                  15

Ile Arg Ser Arg Cys Gly Lys Trp Val Ser Glu Ile Arg Glu Pro Arg
            20                  25                  30

Lys Ala Arg Arg Ile Trp Leu Gly Thr Phe Pro Thr Pro Glu Met Ala
        35                  40                  45

Ala Val Ala Tyr Asp Val Ala Ala Arg Ala Leu Arg Gly Pro Asp Ala
    50                  55                  60

Ala Leu Asn Phe Pro Ala Ile Ala Ala Ser Arg Pro Ala Pro Ala Ser
65                  70                  75                  80

Thr Ser Ala Asp Asp Ile Arg Ala Ala Ala Ala Ala Ala Ala Ala Ser
                85                  90                  95

Leu Ala Gly Gly Gly Gly Ile Ala Pro Pro Gly Ala Ala Gly Ser
            100                 105                 110

Ala Val Gln Gln Gln Gln Gln Phe Gly Gly Gly Ser Gly Thr Ala Ala
        115                 120                 125

Gly Ser Glu Glu Ala Ala Ser Ile Gly Ala Asn Tyr Tyr Asn Val Asn

```
                130              135               140
Gln Gln Gln Gln Tyr Phe Leu Asp Glu Glu Ala Leu Phe Glu Thr Pro
145                 150                 155                 160

Gln Phe Leu Arg Ser Met Ala Ala Gly Met Met Ser Pro Pro Arg
                165                 170                 175

Leu Ser Pro Asp Ser Ser Asp Glu Ser Pro Asp Pro Ser Glu Ala Gly
            180                 185                 190

Glu Ser Leu Trp Ser Tyr Arg Asp Pro
            195                 200

<210> SEQ ID NO 58
<211> LENGTH: 858
<212> TYPE: DNA
<213> ORGANISM: Brachypodium distachyon
<220> FEATURE:
<221> NAME/KEY: ERF_Transcription_Factor
<222> LOCATION: (1)..(858)

<400> SEQUENCE: 58
atggctgagc ctgagcagcc ttctgctcct tcttcttctg ctcctgctcc tcctcagctc     60
caggtggctg ctgataataa tcctacaaca gtggatgagt gctctgatcc tggcggcaat    120
tctgctgctt cttctgctca ttctcctgct cctgctcctc agcagctcgc tagggatgat    180
acagtgggca ttattacaac agctatgggc gctgctgctg ctgctacatc ttcttctggc    240
gagccttctc ctaggtctac aggcaggcat cctttctaca ggggcattag gtgcaggaat    300
ggcaagtggg tgtctgagat tagggagcct aggaaggcta ggaggatttg gctcggcaca    360
taccctacag ctgagatggc tgctgctgct tacgatgtgg ctgctagggc tctcagggc     420 cctgatgctg tgctcaattt ccctggcgct acagctacaa ggcctgctcc tgcttctgct    480
tctcctgagg atattagggc tgctgctgct gctgctgctg ctgctctcca gcctattatt    540
gataagcctg cgctagggc tcctgaggct gatgctgctg ctgctgatcc tgctgctgct     600
gctgagcagg tgcagaggca tcatgatcag acaggctctg ctgctgctgg cggcgatgag    660
cctaggcaga aggagattgg caatgagggc gaggagttca tggatgagga ggctattttc    720
gagatgcctc agatgctcag gaatatggct gctggcatga tgatgtctcc tcctaggctc    780
tctcctacag cttctgatga gtggcctgct gatccttctg cgctggcga gtctctctgg    840 tcttaccatg atccttga                                                  858

<210> SEQ ID NO 59
<211> LENGTH: 285
<212> TYPE: PRT
<213> ORGANISM: Brachypodium distachyon
<220> FEATURE:
<221> NAME/KEY: ERF_Transcription_Factor
<222> LOCATION: (1)..(285)

<400> SEQUENCE: 59

Met Ala Glu Pro Glu Gln Pro Ser Ala Pro Ser Ser Ala Pro Ala
1               5                   10                  15

Pro Pro Gln Leu Gln Val Ala Ala Asp Asn Asn Pro Thr Thr Val Asp
                20                  25                  30

Glu Cys Ser Asp Pro Gly Gly Asn Ser Ala Ala Ser Ala His Ser
            35                  40                  45

Pro Ala Pro Ala Pro Gln Gln Leu Ala Arg Asp Asp Thr Val Gly Ile
        50                  55                  60

Ile Thr Thr Ala Met Gly Ala Ala Ala Ala Ala Thr Ser Ser Ser Gly
```

```
            65                  70                  75                  80
Glu Pro Ser Pro Arg Ser Thr Gly Arg His Pro Phe Tyr Arg Gly Ile
                    85                  90                  95
Arg Cys Arg Asn Gly Lys Trp Val Ser Glu Ile Arg Glu Pro Arg Lys
                100                 105                 110
Ala Arg Arg Ile Trp Leu Gly Thr Tyr Pro Thr Ala Glu Met Ala Ala
            115                 120                 125
Ala Ala Tyr Asp Val Ala Ala Arg Ala Leu Arg Gly Pro Asp Ala Val
        130                 135                 140
Leu Asn Phe Pro Gly Ala Thr Ala Thr Arg Pro Ala Pro Ala Ser Ala
145                 150                 155                 160
Ser Pro Glu Asp Ile Arg Ala Ala Ala Ala Ala Ala Ala Ala Ala Leu
                165                 170                 175
Gln Pro Ile Ile Asp Lys Pro Gly Ala Arg Ala Pro Glu Ala Asp Ala
                180                 185                 190
Ala Ala Ala Asp Pro Ala Ala Ala Ala Glu Gln Val Gln Arg His His
            195                 200                 205
Asp Gln Thr Gly Ser Ala Ala Ala Gly Gly Asp Glu Pro Arg Gln Lys
        210                 215                 220
Glu Ile Gly Asn Glu Gly Glu Glu Phe Met Asp Glu Ala Ile Phe
225                 230                 235                 240
Glu Met Pro Gln Met Leu Arg Asn Met Ala Ala Gly Met Met Met Ser
                245                 250                 255
Pro Pro Arg Leu Ser Pro Thr Ala Ser Asp Glu Trp Pro Ala Asp Pro
            260                 265                 270
Ser Gly Ala Gly Glu Ser Leu Trp Ser Tyr His Asp Pro
        275                 280                 285

<210> SEQ ID NO 60
<211> LENGTH: 750
<212> TYPE: DNA
<213> ORGANISM: Brachypodium distachyon
<220> FEATURE:
<221> NAME/KEY: ERF_Transcription_Factor
<222> LOCATION: (1)..(750)

<400> SEQUENCE: 60
atgcctgagc aggatgtgtg ctctcctgct tcttctggcg ctctggcac aacatcttct      60 tctcctcctg cttctcctgg cttcggctct aataggaggg ctagggatga tggcgtgggc     120
ggcggcaggc atccttctta caggggcgtg aggatgaggg cttggggcaa gtgggtgtct     180
gagattaggg agcctaggaa gaagtctagg atttggctcg gcacattccc tacacctgag     240
atggctgcta gggctcatga tgctgctgct ctcgtggtga agggccctgc tgctgtgctc     300
aatttccctg atctcgcttc taggctccct aggcctgctt cttcttctcc tagggatgtg     360
caggctgctg ctgtgagggc tgctgctatg gatatgggcc atctccatca tcagcagcag     420
cctgctgctg ctgctctctc tccttcttct cctgctcctg ctatgatgct ccagcagcct     480
gtgatttctg ctgctgctga tgtggtggat gatctcgatg ctattttcga gctccctagg     540
ctcgatgatg atgctacagg ccatgtgttc ggcggcctca caatgctga tcatcatcag     600 cagtcttggt gcgatcctgt gtggatggat gatgatggct gctcttacgc tcaggaggat     660
atgttcggct tcggcctcga tgctgctgtg gatcagtacc atggctgggg cgctccttct     720
tctgtgtctg ctctcctctg gaatctctga                                     750
```

<210> SEQ ID NO 61
<211> LENGTH: 249
<212> TYPE: PRT
<213> ORGANISM: Brachypodium distachyon
<220> FEATURE:
<221> NAME/KEY: ERF_Transcription_Factor
<222> LOCATION: (1)..(249)

<400> SEQUENCE: 61

Met Pro Glu Gln Asp Val Cys Ser Pro Ala Ser Ser Gly Gly Ser Gly
1               5                   10                  15

Thr Thr Ser Ser Ser Pro Pro Ala Ser Pro Gly Phe Gly Ser Asn Arg
            20                  25                  30

Arg Ala Arg Asp Asp Gly Val Gly Gly Arg His Pro Ser Tyr Arg
        35                  40                  45

Gly Val Arg Met Arg Ala Trp Gly Lys Trp Val Ser Glu Ile Arg Glu
    50                  55                  60

Pro Arg Lys Lys Ser Arg Ile Trp Leu Gly Thr Phe Pro Thr Pro Glu
65                  70                  75                  80

Met Ala Ala Arg Ala His Asp Ala Ala Ala Leu Val Val Lys Gly Pro
                85                  90                  95

Ala Ala Val Leu Asn Phe Pro Asp Leu Ala Ser Arg Leu Pro Arg Pro
            100                 105                 110

Ala Ser Ser Ser Pro Arg Asp Val Gln Ala Ala Val Arg Ala Ala
        115                 120                 125

Ala Met Asp Met Gly His Leu His His Gln Gln Pro Ala Ala Ala
    130                 135                 140

Ala Leu Ser Pro Ser Ser Pro Ala Pro Ala Met Met Leu Gln Gln Pro
145                 150                 155                 160

Val Ile Ser Ala Ala Ala Asp Val Val Asp Asp Leu Asp Ala Ile Phe
                165                 170                 175

Glu Leu Pro Arg Leu Asp Asp Ala Thr Gly His Val Phe Gly Gly
            180                 185                 190

Leu Thr Met Ala Asp His His Gln Gln Ser Trp Cys Asp Pro Val Trp
        195                 200                 205

Met Asp Asp Asp Gly Cys Ser Tyr Ala Gln Glu Asp Met Phe Gly Phe
    210                 215                 220

Gly Leu Asp Ala Ala Val Asp Gln Tyr His Gly Trp Gly Ala Pro Ser
225                 230                 235                 240

Ser Val Ser Ala Leu Leu Trp Asn Leu
                245

<210> SEQ ID NO 62
<211> LENGTH: 579
<212> TYPE: DNA
<213> ORGANISM: Brachypodium distachyon
<220> FEATURE:
<221> NAME/KEY: ERF_Transcription_Factor
<222> LOCATION: (1)..(579)

<400> SEQUENCE: 62
atggagatgc atgataatgc tgctggcatt gctgctgctg ctgctgctgc tgctgagcag      60
tacaggggcg tgaggaagag gaagtggggc aagtgggtgt ctgagattag ggagcctggc     120
aagaagacaa ggatttggct cggctctttc gagtctcctg agatggctgc tgtggctcat     180
gatgtggctg ctctcaggct caggggcagg gatgctaggc tcaatttccc tggcctcgct     240
catctcttca ggaggcctgc tacagctgag cctgatgatg tgagggctgc tgctctcgag     300

```
gctgctgctc aggtgaggtt caggcctgat ctcgtgatgc agctccctgg ctctcatggc      360
aatggcggcg gcgatggcgg ctctcctgag tacaggctcg atgatgtggc ttgggatgtg      420
gtgctcggcg ctgatgatct cgaggctcag tctcctaata tgtgggctga gctcgctgag      480
gctatgctcc tcgctcctcc tgtgtggggc ggcggcgctg tggataatga tgattgggct      540
cagggctctc tctgggagcc ttcttgctgg tcttactga                             579
```

```
<210> SEQ ID NO 63
<211> LENGTH: 192
<212> TYPE: PRT
<213> ORGANISM: Brachypodium distachyon
<220> FEATURE:
<221> NAME/KEY: ERF_Transcription_Factor
<222> LOCATION: (1)..(192)

<400> SEQUENCE: 63

Met Glu Met His Asp Asn Ala Ala Gly Ile Ala Ala Ala Ala Ala Ala
1               5                   10                  15

Ala Ala Glu Gln Tyr Arg Gly Val Arg Lys Arg Lys Trp Gly Lys Trp
            20                  25                  30

Val Ser Glu Ile Arg Glu Pro Gly Lys Lys Thr Arg Ile Trp Leu Gly
        35                  40                  45

Ser Phe Glu Ser Pro Glu Met Ala Ala Val His Asp Val Ala Ala
    50                  55                  60

Leu Arg Leu Arg Gly Arg Asp Ala Arg Leu Asn Phe Pro Gly Leu Ala
65                  70                  75                  80

His Leu Phe Arg Arg Pro Ala Thr Ala Glu Pro Asp Asp Val Arg Ala
                85                  90                  95

Ala Ala Leu Glu Ala Ala Ala Gln Val Arg Phe Arg Pro Asp Leu Val
            100                 105                 110

Met Gln Leu Pro Gly Ser His Gly Asn Gly Gly Gly Asp Gly Gly Ser
        115                 120                 125

Pro Glu Tyr Arg Leu Asp Asp Val Ala Trp Asp Val Val Leu Gly Ala
    130                 135                 140

Asp Asp Leu Glu Ala Gln Ser Pro Asn Met Trp Ala Glu Leu Ala Glu
145                 150                 155                 160

Ala Met Leu Leu Ala Pro Pro Val Trp Gly Gly Ala Val Asp Asn
                165                 170                 175

Asp Asp Trp Ala Gln Gly Ser Leu Trp Glu Pro Ser Cys Trp Ser Tyr
            180                 185                 190
```

```
<210> SEQ ID NO 64
<211> LENGTH: 516
<212> TYPE: DNA
<213> ORGANISM: Brachypodium distachyon
<220> FEATURE:
<221> NAME/KEY: ERF_Transcription_Factor
<222> LOCATION: (1)..(516)

<400> SEQUENCE: 64
atggataata atttcagggc tgctccttct gctcctcagt acaggggcgt gaggaggagg      60
aagtggggca gtgggtgtc tgagattagg cagcctggca caaagctcag ggtgtggctc      120
ggctctttcg atacagctga gatggctgct gtggctcatg atgtggctgc tctcaggctc      180 agggggcgcta gggatgctca gctcaatttc cctggctctg tggctggct ccctcagcct      240 cctacaacag atcctacaga tattagggct gctgctgctg aggctgctga gagggtgagg      300
agggagcctg ctctcgtgtc tgctgctgct aatacaacaa ttacaattaa tcctggcgag      360
```

```
ttcgatgatg atcagctcga gtctcctaag ctctgggatc agatggctga ggctatgctc    420
ctcgatcctc ctaggtgggg ccaggatggc tctggcggcg atgctgctga gtcttctcat    480
tcttggcctc agggctctct ctgggatggc tgctga                              516

<210> SEQ ID NO 65
<211> LENGTH: 171
<212> TYPE: PRT
<213> ORGANISM: Brachypodium distachyon
<220> FEATURE:
<221> NAME/KEY: ERF_Transcription_Factor
<222> LOCATION: (1)..(171)

<400> SEQUENCE: 65

Met Asp Asn Asn Phe Arg Ala Ala Pro Ser Ala Pro Gln Tyr Arg Gly
1               5                   10                  15

Val Arg Arg Arg Lys Trp Gly Arg Trp Val Ser Glu Ile Arg Gln Pro
            20                  25                  30

Gly Thr Lys Leu Arg Val Trp Leu Gly Ser Phe Asp Thr Ala Glu Met
        35                  40                  45

Ala Ala Val Ala His Asp Val Ala Ala Leu Arg Leu Arg Gly Ala Arg
    50                  55                  60

Asp Ala Gln Leu Asn Phe Pro Gly Ser Val Gly Trp Leu Pro Gln Pro
65                  70                  75                  80

Pro Thr Thr Asp Pro Thr Asp Ile Arg Ala Ala Ala Glu Ala Ala
                85                  90                  95

Glu Arg Val Arg Arg Glu Pro Ala Leu Val Ser Ala Ala Ala Asn Thr
                100                 105                 110

Thr Ile Thr Ile Asn Pro Gly Glu Phe Asp Asp Gln Leu Glu Ser
            115                 120                 125

Pro Lys Leu Trp Asp Gln Met Ala Glu Ala Met Leu Leu Asp Pro Pro
        130                 135                 140

Arg Trp Gly Gln Asp Gly Ser Gly Gly Asp Ala Ala Glu Ser Ser His
145                 150                 155                 160

Ser Trp Pro Gln Gly Ser Leu Trp Asp Gly Cys
                165                 170
```